(12) United States Patent
Feigelson et al.

(10) Patent No.: US 10,894,796 B2
(45) Date of Patent: Jan. 19, 2021

(54) MK2 INHIBITORS, SYNTHESIS THEREOF, AND INTERMEDIATES THERETO

(71) Applicant: Celgene CAR LLC, Pembroke (BM)

(72) Inventors: Gregg Brian Feigelson, Chester, NY (US); Maryll E. Geherty, Pennington, NJ (US); Richard Martin Heid, Jr., Maplewood, NJ (US); Mohit Kothare, Bridgewater, NJ (US); Hon-Wah Man, Princeton, NJ (US); Alexander L. Ruchelman, Cream Ridge, NJ (US); John F. Traverse, Lebanon, NJ (US); Kelvin Hin-Yeong Yong, Westfield, NJ (US); Chengmin Zhang, Florham Park, NJ (US)

(73) Assignee: Celgene CAR LLC, Pembroke (BM)

( * ) Notice: Subject to any disclaimer, the term of this patent is extended or adjusted under 35 U.S.C. 154(b) by 0 days.

(21) Appl. No.: 16/494,701

(22) PCT Filed: Mar. 15, 2018

(86) PCT No.: PCT/US2018/022547
§ 371 (c)(1),
(2) Date: Sep. 16, 2019

(87) PCT Pub. No.: WO2018/170203
PCT Pub. Date: Sep. 20, 2018

(65) Prior Publication Data
US 2020/0102326 A1    Apr. 2, 2020

Related U.S. Application Data

(60) Provisional application No. 62/472,024, filed on Mar. 16, 2017.

(51) Int. Cl.
*C07D 495/14* (2006.01)
*C07D 513/14* (2006.01)

(52) U.S. Cl.
CPC ................... *C07D 495/14* (2013.01)

(58) Field of Classification Search
CPC .......................... C07D 495/14; C07D 513/14
See application file for complete search history.

(56) References Cited

U.S. PATENT DOCUMENTS

| 7,838,674 B2 | 11/2010 | Schlapbach et al. |
| 9,458,175 B2 | 10/2016 | Alexander et al. |
| 9,790,235 B2 | 10/2017 | Alexander et al. |
| 10,138,256 B2 | 11/2018 | Alexander et al. |
| 10,253,040 B1 | 4/2019 | Alexander et al. |
| 10,577,380 B2 | 3/2020 | Alexander et al. |
| 2009/0156557 A1 | 6/2009 | Brown et al. |
| 2012/0022030 A1 | 1/2012 | Schlapbach et al. |
| 2013/0137708 A1 | 5/2013 | Garske et al. |
| 2014/0018343 A1 | 1/2014 | Romero et al. |
| 2019/0375762 A1 | 12/2019 | Alexander et al. |
| 2020/0102325 A1 | 4/2020 | Guo et al. |
| 2020/0102327 A1 | 4/2020 | Malona et al. |
| 2020/0148701 A1 | 5/2020 | Han et al. |

FOREIGN PATENT DOCUMENTS

| WO | WO-2004/058762 A1 | 7/2004 |
| WO | WO-2005/105814 A1 | 11/2005 |
| WO | WO-2009/010488 A1 | 1/2009 |
| WO | WO-2014/149164 A1 | 9/2014 |
| WO | WO-2016/044463 A2 | 3/2016 |
| WO | WO-2018/170199 A1 | 9/2018 |
| WO | WO-2018/170200 A1 | 9/2018 |
| WO | WO-2018/170201 A1 | 9/2018 |
| WO | WO-2018/170203 A1 | 9/2018 |
| WO | WO-2018/170204 A1 | 9/2018 |

OTHER PUBLICATIONS

Anderson, D.R. et al., Benzothiophene inhibitors of MK2. Part 2: Improvements in kinase selectivity and cell potency, Bioorganic & Medicinal Chemistry Letters, 19: 4882-4884 (2009).
International Search Report for PCT/US2015/050495, 2 pages (dated Dec. 11, 2015).
International Search Report for PCT/US2018/022547, 3 pages (dated Apr. 27, 2018).
Natesan, S. et al., Binding Affinity Prediction for Ligans and Receptors Forming Tautomers and Ionization Species: Inhibition of Mitogen-Activated Protein Kinase-Activated Protein Kinase 2 (MK2), Journal of Medicinal Chemistry, 55(5): 2035-2047 (2012).
Lian, Y. et al., Preparation of Heteroaryl Ethers from Azine N-Oxides and Alcohols, Org. Lett., 18:1362-1365 (2016).

*Primary Examiner* — Bruck Kifle
(74) *Attorney, Agent, or Firm* — Choate, Hall & Stewart LLP; Kristen C. Buteau; Nicholas J. Pace

(57) ABSTRACT

The present invention provides methods of preparing a MK2 inhibitor, and intermediates related thereto.

19 Claims, No Drawings

MK2 INHIBITORS, SYNTHESIS THEREOF, AND INTERMEDIATES THERETO

CROSS-REFERENCE TO RELATED APPLICATIONS

The present application claims priority to U.S. Provisional Patent Application No. 62/472,024, filed on Mar. 16, 2017, the entirety of which is hereby incorporated by reference.

TECHNICAL FIELD OF THE INVENTION

The present invention relates to compounds useful as inhibitors of MK2 kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α. (see Deak et al., *EMBO*. 17:4426-4441 (1998); Shi et al., *Biol. Chem.* 383:1519-1536 (2002); Staklatvala, *Curr. Opin. Pharmacol.* 4:372-377 (2004), and Shiroto et al., *J. Mol. Cardiol.* 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

As described herein, in some embodiments, the present invention provides methods for preparing compounds useful as inhibitors of protein kinases. Such compounds include compound I:

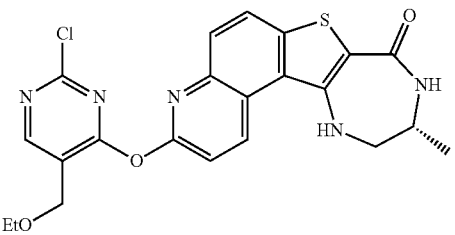

or a pharmaceutically acceptable salt thereof.

The present invention also provides synthetic intermediates useful for preparing such compounds.

The synthesis of compound I is described in Example 82 of WO 2016/044463, published on Mar. 24, 2016 ("the '463 application"). This synthesis, depicted in Scheme 1, below, consists of 12 chemical transformation steps with a combined yield of about 1.8% for the longest linear sequence.

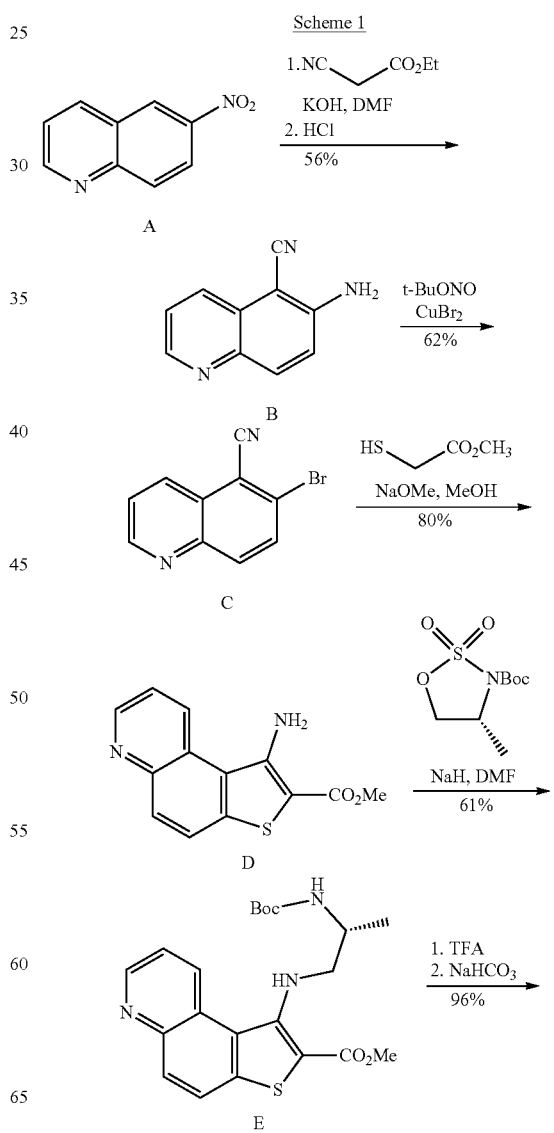

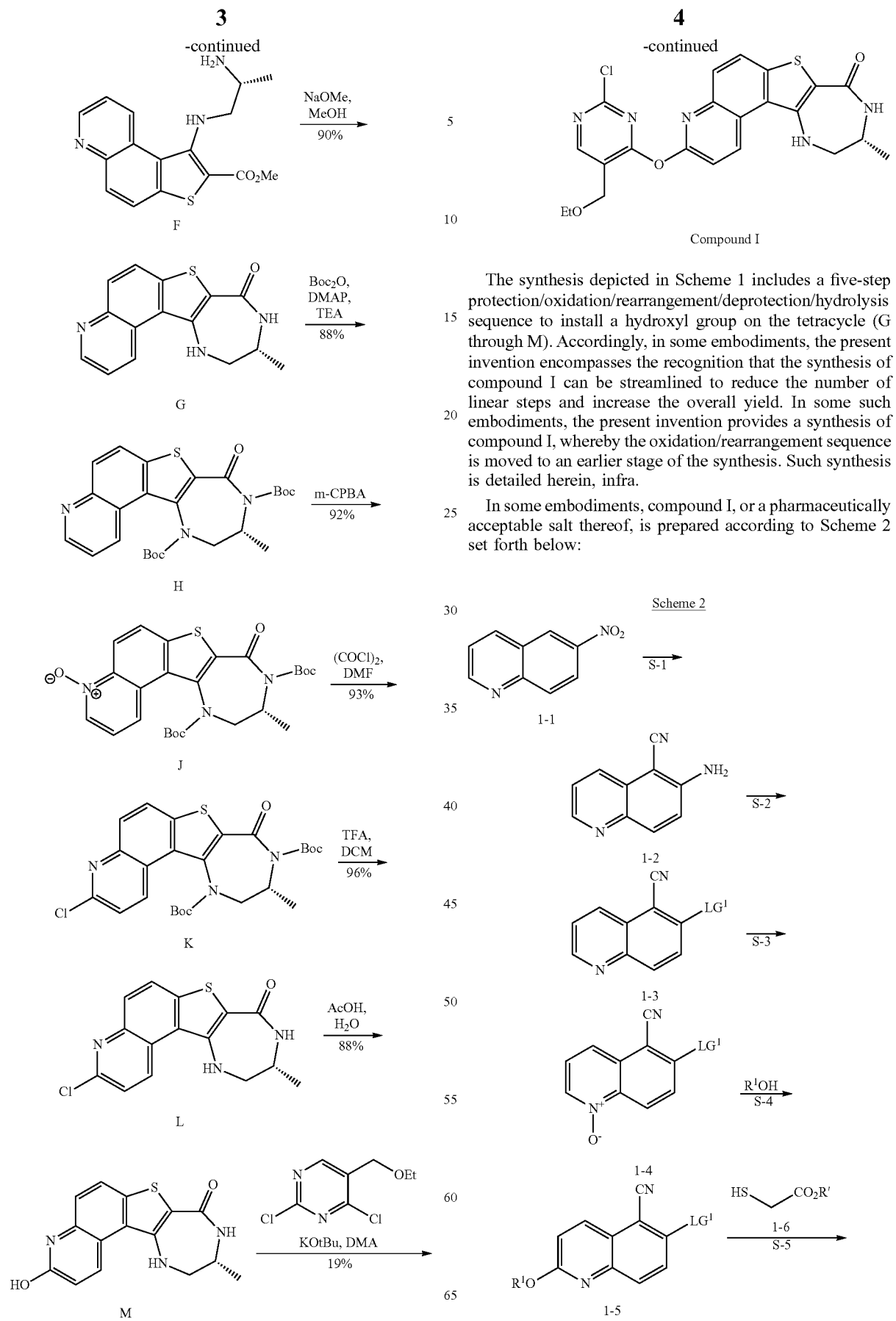

The synthesis depicted in Scheme 1 includes a five-step protection/oxidation/rearrangement/deprotection/hydrolysis sequence to install a hydroxyl group on the tetracycle (G through M). Accordingly, in some embodiments, the present invention encompasses the recognition that the synthesis of compound I can be streamlined to reduce the number of linear steps and increase the overall yield. In some such embodiments, the present invention provides a synthesis of compound I, whereby the oxidation/rearrangement sequence is moved to an earlier stage of the synthesis. Such synthesis is detailed herein, infra.

In some embodiments, compound I, or a pharmaceutically acceptable salt thereof, is prepared according to Scheme 2 set forth below:

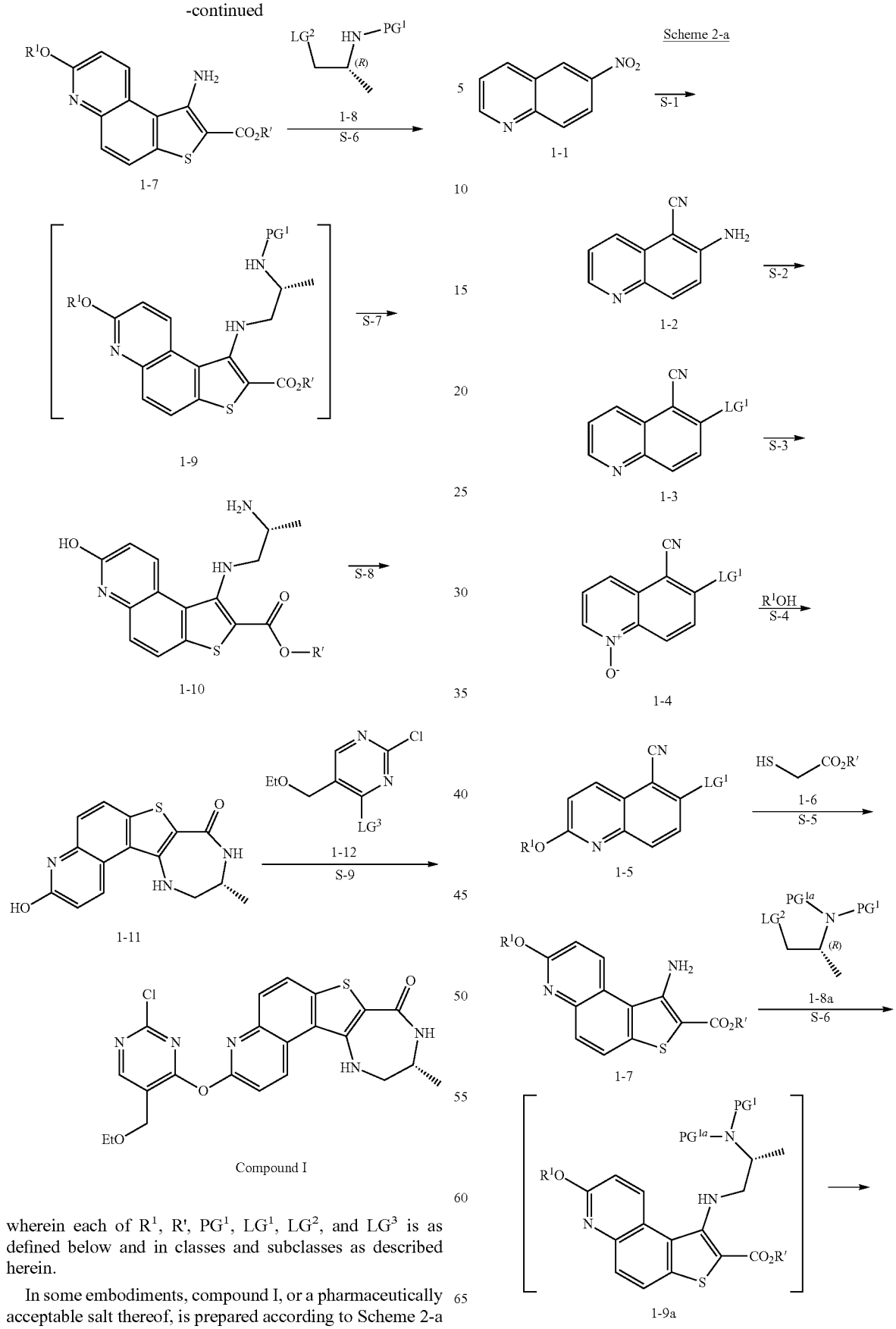
wherein each of $R^1$, R', $PG^1$, $LG^1$, $LG^2$, and $LG^3$ is as defined below and in classes and subclasses as described herein.
In some embodiments, compound I, or a pharmaceutically acceptable salt thereof, is prepared according to Scheme 2-a set forth below:

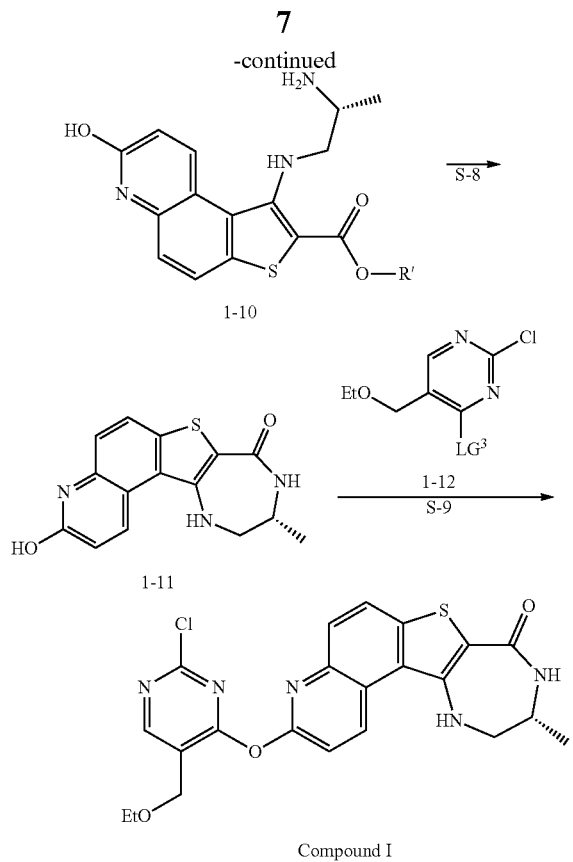

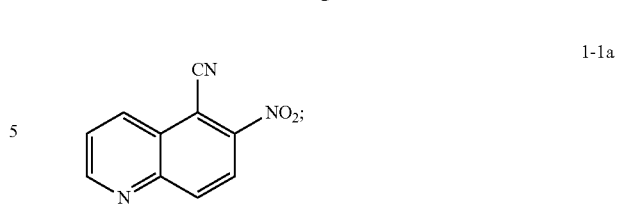

or a salt thereof;
and (b) contacting a compound of formula 1-1a with a suitable reducing agent,
to thereby afford a compound of formula 1-2, or a salt thereof.

In some embodiments, at step (a) of step S-1, a compound of formula 1-1 is contacted with a cyanating agent. In some embodiments, a cyanating agent is a nitrile ester. In some embodiments, a cyanating agent is ethyl cyanoacetate. In some embodiments, a cyanating agent is methyl cyanoacetate.

In some embodiments, at step (b) of step S-1, a compound of formula 1-1 is contacted with a reducing agent. Suitable reducing agents are known in the art, and include hydrides, iron (Fe), etc. Exemplary other such reducing agents are known in the art, for instance, see *Comprehensive Organic Transformations*, R. C. 2$^{nd}$ Edition, John Wiley & Sons, 1999, pages 823-927.

In some embodiments, the crude product of step (a) of step S-1 is taken into step (b) of step S-1 without further treatment or purification. For instance, in some embodiments, a reducing agent is added directly to the resulting mixture of step (a) of step S-1. In some embodiments, step (b) of step S-1 comprises adding a reducing agent to the mixture. In some embodiments, a reducing agent is added at a rate sufficient to maintain a certain temperature. In some embodiments, the reaction temperature is maintained at room temperature. In some embodiments, the reaction temperature is maintained at between about 20° C. and about 25° C. In some embodiments, the reaction temperature is maintained at between about 0° C. and about 50° C.

In some embodiments, the present invention provides a method for preparing a compound of formula 1-2:

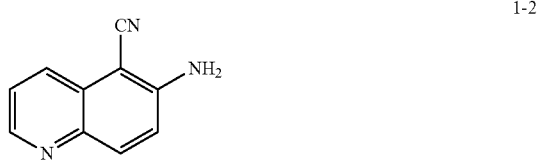 [SMILES: N#Cc1c(N)ccc2ncccc12]

or a salt thereof,
comprising the step of reacting a compound of formula 1-1:

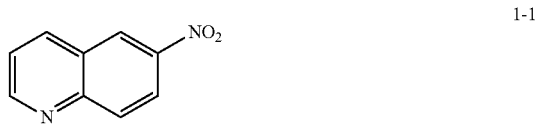 [SMILES: O=[N+]([O-])c1ccc2ncccc2c1]

or a salt thereof;
under suitable reaction conditions to afford the compound of formula 1-2, or a salt thereof.

wherein each of R$^1$, R', PG$^1$, PG$^{1a}$, LG$^1$, LG$^2$, and LG$^3$ is as defined below and in classes and subclasses as described herein.

It will be appreciated that compounds described herein, e.g., compounds in Scheme 2 or Scheme 2-a, may be in salt form. For example, compounds in Scheme 2 or Scheme 2-a, which contain a basic nitrogen atom may form a salt with a suitable acid. For example, an NH$_2$ group may be represented as NH$_3^+$ and may associate with a suitable negatively charged counterion. Alternatively and/or additionally, it will be appreciated that certain —OH groups in compounds of Scheme 2 or Scheme 2-a may form a salt with a suitable base. For example, an OH group may be represented as O$^-$ and associate with a suitable positively charged counterion. Suitable counterions are well known in the art, e.g., see generally, *March's Advanced Organic Chemistry: Reactions, Mechanisms, and Structure*, M. B. Smith and J. March, 5$^{th}$ Edition, John Wiley & Sons, 2001. All forms and types of salts are contemplated by and are within the scope of the invention.

Step S-1 of Scheme 2 or Scheme 2-a

At step S-1, commercially available compound of formula 1-1 is cyanated, followed by reduction of the nitro group to the corresponding amine of a compound of formula 1-2.

In some embodiments, at step S-1, a compound of formula 1-2 is prepared in a "one pot" reaction, such "one pot" reaction comprising cyanating a compound of formula 1-1, followed by in situ reduction of the nitro group, to thereby afford a compound of formula 1-2.

In some embodiments, at step S-1, a compound of formula 1-2 is prepared by a two-step process, comprising:
(a) contacting a compound of formula 1-1 with a cyanating agent to afford a compound of formula 1-1a:

In some embodiments of step S-1, a compound of formula 1-1 is contacted with a cyanating agent. In some embodiments, the cyanating agent is a nitrile ester. In some embodiments, the nitrile ester is ethyl cyanoacetate or methyl cyanoacetate.

In some embodiments, a compound of formula 1-1 is contacted with a cyanating agent in the presence of a base. In some embodiments, the base is an organic base. In some embodiments, the base is 1,8-diazabicyclo[5.4.0]undec-7-ene (DBU).

In some embodiments, step S-1 is conducted in the presence of a solvent. In some embodiments, the solvent comprises an organic solvent. In some embodiments, the solvent comprises a polar aprotic solvent. In some such embodiments, the solvent comprises DMSO. In some embodiments, the solvent further comprises water.

In some embodiments, step S-1 comprises an initial step of heating a mixture of a base (e.g., DBU), and a solvent (e.g., DMSO) to an elevated temperature. In some embodiments, an elevated temperature is about 30° C. to about 60° C. In some embodiments, an elevated temperature is about 40° C. to about 45° C. In some embodiments, once the reaction is heated to an elevated temperature, a cyanating agent (e.g., ethyl cyanoacetate) is added. In some embodiments, a cyanating agent (e.g., ethyl cyanoacetate) is added at a rate sufficient to maintain the reaction temperature.

In some embodiments, after a cyanating agent (e.g., ethyl cyanoacetate) is added to the mixture, the mixture is cooled to a lower temperature. In some embodiments, a lower temperature is room temperature. In some embodiments, a lower temperature is about 20° C. to about 25° C.

In some embodiments, the reaction is held at a lower temperature for between about 8 hrs and about 24 hrs. In some embodiments, the reaction is held at a lower temperature for between about 12 hrs and about 20 hrs. In some embodiments, the reaction is held at a lower temperature for about 16 hrs.

In some embodiments of step S-1, an acid (e.g., HCl) is added directly to the resulting mixture of compound 1-1 and the cyanating agent. In some embodiments, step S-1 comprises adding an acid (e.g., HCl) to the mixture. In some embodiments, an acid (e.g., HCl) is added at a rate sufficient to maintain temperature. In some embodiments, the temperature is maintained at room temperature. In some embodiments, the temperature is maintained at between about 20° C. and about 25° C. In some embodiments, the temperature is maintained at between about 0° C. and about 50° C.

In some embodiments, once the acid (e.g., HCl) is added, the reaction mixture is heated to an elevated temperature. In some embodiments, an elevated temperature is about 80° C. to about 90° C. In some embodiments, an elevated temperature is one wherein the reaction is heated to reflux.

In some embodiments, the reaction is held at an elevated temperature for about 2 hrs to about 8 hrs. In some embodiments, the reaction is held at an elevated temperature for about 2 hrs. In some embodiments, the reaction is held at an elevated temperature for about 3 hrs. In some embodiments, the reaction is held at an elevated temperature for about 4 hrs. In some embodiments, the reaction is held at an elevated temperature for about 5 hrs. In some embodiments, the reaction is held at an elevated temperature for about 6 hrs. In some embodiments, the reaction is held at an elevated temperature for about 7 hrs. In some embodiments, the reaction is held at an elevated temperature for about 8 hrs.

In some embodiments, the present invention provides a method for preparing a compound of formula 1-2:

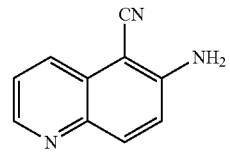

1-2 or a salt thereof,
comprising the steps of
(a) providing a compound of formula 1-1

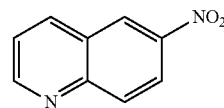

1-1 or a salt thereof, and
(b) reacting the compound of formula 1-1, or a salt thereof, with a cyanating agent and an acid, to thereby afford the compound of formula 1-2, or a salt thereof.

Step S-2 of Scheme 2 or Scheme 2-a

At step S-2, the amine group of a compound of formula 1-2 is converted to leaving group $LG^1$.

As defined herein, a suitable "leaving group" that is "subject to nucleophilic displacement" is a chemical group that is readily displaced by a desired incoming nucleophilic chemical entity. Suitable leaving groups are well known in the art, e.g., see generally, *March's Advanced Organic Chemistry: Reactions, Mechanisms, and Structure*, M. B. Smith and J. March, 5$^{th}$ Edition, John Wiley & Sons, 2001. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, phosphonate, sulfoxide, sulphone, and diazonium moieties. For the above mentioned "optionally substituted" moieties, the moieties may be optionally substituted with $C_{1-4}$ aliphatic, fluoro-substituted $C_{1-4}$ aliphatic, halogen, or nitro. Examples of suitable leaving groups include chloro, iodo, bromo, fluoro, sulfoxide, sulphone, methanesulfonyloxy (mesyloxy), tosyloxy, triflyloxy, benzenesulfonyloxy, nitro-phenylsulfonyloxy (nosyloxy), and bromo-phenylsulfonyloxy (brosyloxy).

In some embodiments, a leaving group is —OSO$_2$R, wherein R is hydrogen or optionally substituted $C_{1-6}$ aliphatic or aryl.

As generally defined above, R is hydrogen or optionally substituted $C_{1-6}$ aliphatic or aryl. In some embodiments, R is hydrogen. In some embodiments, R is optionally substituted $C_{1-6}$ aliphatic or aryl. In some embodiments, R is optionally substituted $C_{1-6}$ aliphatic. In some embodiments, R is methyl. In some embodiments, R is optionally substituted aryl. In some embodiments, an aryl group has 5-14 aromatic ring atoms. In some embodiments, R is optionally substituted phenyl. In some embodiments, R is phenyl. In some embodiments, R is tolyl. In some embodiments, R is p-tolyl.

In some embodiments, a leaving group is —OSO$_2$R wherein R is optionally substituted $C_{1-6}$ aliphatic or aryl. In some embodiments, a leaving group is —OSO$_2$R wherein R is optionally substituted $C_{1-6}$ aliphatic. In some embodiments, a leaving group is —OSO$_2$R wherein R is methyl. In some embodiments, a leaving group is —OSO$_2$R wherein R is optionally substituted aryl. In some embodiments, a leaving group is —OSO$_2$R wherein R is optionally substituted phenyl. In some embodiments, a leaving group is —OSO$_2$Ph. In some embodiments, a leaving group is —OSO$_2$(p-tolyl). In some embodiments, a leaving group is mesyloxy. In some embodiments, a leaving group is tosyloxy. In some embodiments, a leaving group is triflyloxy. In some embodiments, a leaving group is nosyloxy. In some embodiments, a leaving group is brosyloxy.

In some embodiments of formula 1-3, LG$^1$ is halogen. In some embodiments, LG$^1$ is chlorine. In some embodiments, LG$^1$ is bromide.

In some embodiments, step S-2 is conducted in the presence of reagents that install a leaving group LG$^1$. Such reagents are well known in the art, e.g., see generally, *March's Advanced Organic Chemistry: Reactions, Mechanisms, and Structure*, M. B. Smith and J. March, 5$^{th}$ Edition, John Wiley & Sons, 2001.

In some embodiments, at step S-2, a compound of formula 1-3 is prepared in a "one pot" reaction, such "one pot" reaction comprising in situ formation of a diazonium intermediate of formula 1-2a:

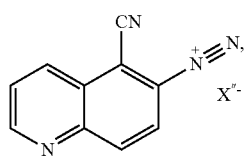

1-2a wherein X" is a counterion.

In some embodiments, at step S-2, a compound of formula 1-3 is prepared in a two-step process, comprising:
(a) formation of a diazonium intermediate of formula 1-2a:

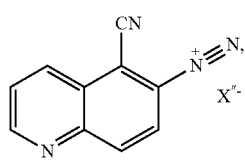

1-2a wherein X" is a counterion; and
(b) contacting the diazonium intermediate of formula 1-2a with a suitable reagent that installs a leaving group LG$^1$, wherein LG$^1$ is halogen.
to thereby afford the compound of formula 1-3, or a salt thereof.

In some embodiments, a suitable reagent that installs a leaving group LG$^1$ is a bromide source, e.g., CuBr$_2$.

In some embodiments of step S-2, diazonium intermediate 1-2a is reacted with a bromide source. In some such embodiments, a bromide source is CuBr$_2$.

In some embodiments, a compound of formula 1-3 is formed in situ from a compound of formula 1-2, the process comprising contacting a compound of formula 1-2 with a bromide source (e.g., CuBr$_2$) in the presence of a nitrite compound. In some embodiments, a nitrite compound is sodium nitrite. In some embodiments, a nitrite compound is potassium nitrite. In some embodiments, a nitrite compound is of formula RONO, wherein R is as defined above and described herein. In some embodiments, a nitrite compound is tert-butyl nitrite.

In some embodiments, step S-2 is conducted in the presence of a solvent. In some embodiments, the solvent comprises a polar aprotic solvent. In some embodiments, the solvent comprises MeCN. In some embodiments, the solvent comprises a polar protic solvent. In some embodiments, the solvent further comprises water. In some embodiments, the solvent comprises a mixture of a polar aprotic solvent and a polar protic solvent. In some embodiments, the solvent comprises a mixture of MeCN and water.

In some embodiments, step S-2 comprises heating a mixture of a compound of formula 1-2, a bromide source (e.g., CuBr$_2$), and a solvent (e.g., MeCN-water) to an elevated temperature. In some embodiments, an elevated temperature is between about 25° C. to about 45° C. In some embodiments, an elevated temperature is between about 30° C. to about 35° C. In some embodiments, the mixture is held at an elevated temperature for between about 15 mins to about 120 mins. In some embodiments, the mixture is held at an elevated temperature for between about 30 mins to about 60 mins.

In some embodiments, a nitrite compound (e.g., tert-butyl nitrite) is added to the mixture of a compound of formula 1-2 and a bromide source. In some embodiments, a nitrite compound (e.g., tert-butyl nitrite) is added over a period of about 60 mins. In some embodiments, the reaction mixture is agitated for between about 2 hr and about 48 hr. In some embodiments, the reaction mixture is agitated for between about 12 hr and about 24 hr. In some embodiments, the reaction mixture is agitated for about 20 h.

In some embodiments, the present invention provides a method for preparing a compound of formula 1-3:

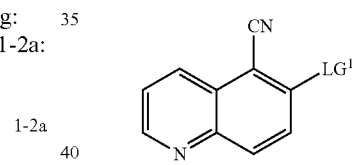

1-3 or a salt thereof, wherein:
LG$^1$ is a suitable leaving group;
comprising the step of reacting a compound of formula 1-2:

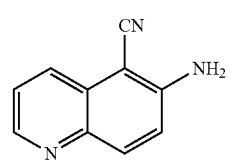

1-2 or a salt thereof;
under suitable reaction conditions to afford the compound of formula 1-3, or a salt thereof.

In some embodiments, the reaction conditions comprise a nitrite compound. In some such embodiments, the nitrite compound is tert-butyl nitrite.

In some embodiments, the reaction conditions further comprise a bromide source. In some such embodiments, the bromide source is CuBr$_2$.

In some embodiments, the present invention provides a method for preparing a compound of formula 1-3:

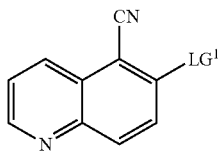

or a salt thereof, wherein:
LG$^1$ is a suitable leaving group;
comprising the steps of:
(a) providing a compound of formula 1-2:

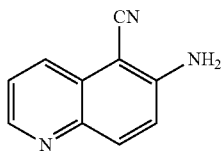

or a salt thereof, and
(b) reacting the compound of formula 1-2, or a salt thereof, with a bromide source and a nitrite compound, to thereby afford the compound of formula 1-3, or a salt thereof.

Step S-3 of Scheme 2 or Scheme 2-a

At step S-3, a compound of formula 1-3 is oxidized to form the N-oxide of formula 1-4.

In some embodiments, step S-3 is conducted in the presence of a peroxide reagent. In some embodiments, a peroxide reagent is hydrogen peroxide. In some embodiments, a peroxide reagent is a peracid. In some embodiments, a peracid contains an acidic —OOH group. In some embodiments, a peracid is of formula ROOH, wherein R is as defined above and described herein. In some embodiments, a peracid is peracetic acid. In some embodiments, a peracid is perbenzoic acid. In some embodiments, a peracid is a substituted perbenzoic acid. In some embodiments, a peracid is meta-chloroperoxybenzoic acid (mCPBA).

In some embodiments, step S-3 is conducted in the presence of a solvent. In some embodiments, the solvent comprises a polar aprotic solvent. In some embodiments, the solvent is dichloromethane.

In some embodiments, step S-3 comprises combining a peroxide reagent (e.g., mCPBA) and a solvent (e.g., dichloromethane). In some embodiments, the reaction is agitated at room temperature. In some embodiments, the reaction is agitated at between about 20° C. and about 25° C. In some embodiments, the reaction is agitated for about 24 hrs.

In some embodiments, at step S-3, a compound of formula 1-4 is prepared by a process comprising:
contacting a compound of formula 1-3:

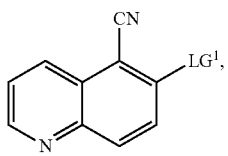

or a salt thereof, wherein:
LG$^1$ is a suitable leaving group;
with an oxidizing reagent,
to thereby afford the compound of formula 1-4, or a salt thereof.

In some embodiments, the present invention provides a method for preparing a compound of formula 1-4:

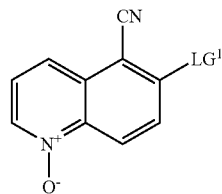

or a salt thereof, wherein:
LG$^1$ is a suitable leaving group;
comprising the step of reacting a compound of formula 1-3:

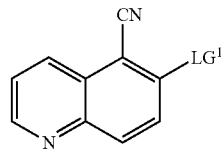

or a salt thereof;
under suitable reaction conditions to afford the compound of formula 1-4, or a salt thereof.

In some embodiments, the present invention provides a method for preparing a compound of formula 1-4:

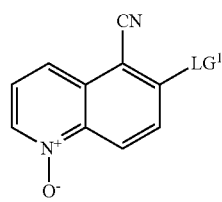

or a salt thereof,
comprising the steps of
(a) providing a compound of formula 1-3

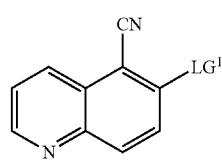

or a salt thereof, and
(b) reacting the compound of formula 1-3, or a salt thereof, with an oxidizing agent, to thereby afford the compound of formula 1-4, or a salt thereof.

In some embodiments of formula 1-4, LG$^1$ is halogen. In some such embodiments, LG$^1$ is bromide.

In some embodiments, the reaction conditions comprise a peroxide reagent. In some such embodiments, the peroxide reagent is mCPBA.

In some embodiments, the present invention provides a method for preparing a compound of formula 1-4:

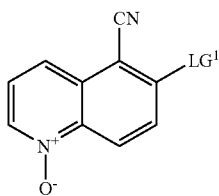

or a salt thereof;
wherein LG$^1$ is Cl, —Br, or —OSO$_3$R, wherein R is hydrogen or optionally substituted C$_{1-6}$ aliphatic or aryl;
comprising the steps of:
(a) providing a compound of formula 1-3:

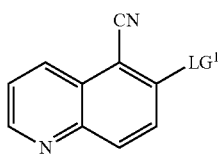

or a salt thereof, and
(b) reacting the compound of formula 1-3, or a salt thereof, with a peroxide, to thereby afford the compound of formula 1-4, or a salt thereof.

Step S-4 of Scheme 2 or Scheme 2-a

At step S-4, a compound of formula 1-4 undergoes a rearrangement to form a compound of formula 1-5.

In some embodiments, at step S-4, a compound of formula 1-5 is prepared by a process comprising:
contacting a compound of formula 1-4:

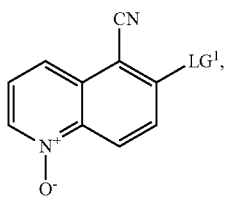

or a salt thereof, wherein:
LG$^1$ is a suitable leaving group;
with R$^1$OH,
to thereby afford the compound of formula 1-5, or a salt thereof.

In some embodiments, step S-4 is conducted in the presence of a compound of formula R$^1$OH, wherein R$^1$OH is a moiety that allows for installation of R$^1$O— to a compound of formula 1-4. In some embodiments, a compound of formula R$^1$OH is an alcohol. In some embodiments, R$^1$ is benzyl, (3-methoxyethoxymethyl, dimethoxytrityl, methoxymethyl, methoxytrityl, p-methoxybenzyl, methylthiomethyl, methyl, and ethoxyethyl. Accordingly, in some embodiments, R$^1$OH is selected from benzyl alcohol, p-methoxybenzyl alcohol, ethoxyethanol (CH$_3$CH$_2$OCH$_2$CH$_2$OH), methoxyethanol (CH$_3$OCH$_2$CH$_2$OH), and methoxymethanol (CH$_3$OCH$_2$OH). In some embodiments, R$^1$OH is benzyl alcohol.

In some embodiments, R$^1$ is an oxygen protecting group PG$^2$. In some embodiments, the R$^1$ group of, e.g., a compound of formulae 1-5, 1-7, 1-9, or 1-9a is PG$^2$. In some embodiments, the R$^1$ group of, e.g., a compound of formulae 1-5, 1-7, 1-9, or 1-9a is further modified to PG$^2$. For example, in some embodiments, R$^1$ is hydrogen, wherein the hydrogen is modified to an oxygen protecting group. Suitable oxygen protecting groups are well known in the art and include those described in detail in *Protecting Groups in Organic Synthesis*, T. W. Greene and P. G. M. Wuts, 3$^{rd}$ edition, John Wiley & Sons, 1999. Examples of suitable oxygen protecting groups include, but are not limited to, acetyl, benzoyl benzyl, β-methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl, tetrahydropyranyl (THP), tetrahydrofuran (THF), trityl, silyl ethers (e.g., trimethylsilyl (TMS), tert-butyldimethylsilyl (TBDMS), tri-iso-propylsilyloxymethyl (TOM), and triisopropylsilyl (TIPS) ethers), methyl ethers, and ethoxyethyl ethers. In some embodiments, PG$^2$ is benzyl.

In some embodiments, step S-4 is conducted in the presence of an activating compound. In some embodiments, an activating compound is an anhydride. In some embodiments, an activating compound is acetic anhydride. In some embodiments, an activating compound is p-toluenesulfonic anhydride. In some embodiments, an activating compound is methanesulfonic anhydride. In some embodiments, an activating compound is a sulfonyl halide. In some embodiments, an activating compound is a sulfonyl chloride. In some embodiments, an activating compound is p-toluenesulfonyl chloride. In some embodiments, an activating compound is methanesulfonyl chloride.

In some embodiments, step S-4 is conducted in the presence of a base. In some embodiments, the base is an organic base. In some embodiments, the base is N,N,-diisopropylethylamine (DIEA).

In some embodiments, step S-4 is conducted in the presence of a suitable solvent. In some embodiments, the solvent comprises an organic solvent. In some embodiments, the solvent comprises a polar aprotic solvent. In some embodiments, the solvent comprises THF.

In some embodiments, step S-4 comprises mixing a compound of formula 1-4 with an alcohol (e.g., benzyl alcohol) and cooling the mixture to a lower temperature. In some embodiments, a lower temperature is between about 3° C. to about 7° C. In some embodiments, a base (e.g., DIEA) is added to the mixture. In some embodiments, the base (e.g., DIEA) is added at a rate sufficient to maintain temperature. In some embodiments, after the base (e.g., DIEA) is added, an activating compound (e.g., p-toluenesulfonic anhydride) in a suitable solvent (e.g., THF) is added. In some embodiments, an activating compound (e.g., p-toluenesulfonic anhydride) in a solvent (e.g., THF) is added over about 2 hrs. After addition of the activating compound (e.g., p-toluenesulfonic anhydride), the reaction mixture is heated to an elevated temperature. In some embodiments, an elevated temperature is room temperature. In some embodiments, an elevated temperature is between about 20° C. and about 25° C. In some embodiments, the reaction mixture is maintained at an elevated temperature for between about 15 mins and about 60 mins. In some embodiments, the reaction mixture is maintained at an elevated temperature for about 30 mins.

In some embodiments, the present invention provides a method for preparing a compound of formula 1-5:

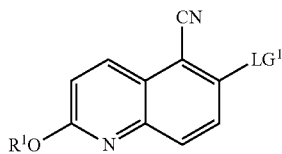

1-5 or a salt thereof, wherein:
LG¹ is a suitable leaving group; and
R¹ is a suitable oxygen protecting group;
comprising the step of reacting a compound of formula 1-4:

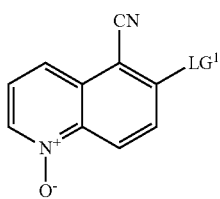

1-4 or a salt thereof,
with a compound of formula R¹OH under suitable reaction conditions to afford a compound of formula 1-5, or a salt thereof.

In some embodiments of formula 1-5, LG¹ is halogen. In some such embodiments, LG¹ is bromide.

In some embodiments, R¹ is benzyl.

In some embodiments, the present invention provides a method for preparing a compound of formula 1-5:

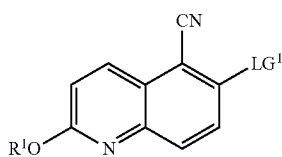

1-5 or a salt thereof; wherein:
LG¹ is a suitable leaving group; and
R¹ is a suitable oxygen protecting group;
comprising the steps of:
(a) providing a compound of formula 1-4:

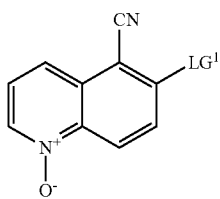

1-4 or a salt thereof;
and
(b) reacting the compound of formula 1-4, or a salt thereof, with R¹OH,
to thereby afford the compound of formula 1-5, or a salt thereof.

Step S-5 of Scheme 2 or Scheme 2-a

At step S-5, a compound of formula 1-5 is coupled with a compound of formula 1-6:

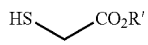

1-6 to thereby afford a compound of formula 1-7. In some embodiments, a compound of formula 1-5 is coupled with a compound of formula 1-6, followed by cyclization to afford a compound of formula 1-7. In some such embodiments, a compound of formula 1-5 is coupled with a compound of formula 1-6 via nucleophilic displacement of LG¹ by the thiol group of a compound of formula 1-6.

In some embodiments, at step S-5, a compound of formula 1-7 is prepared by a process comprising:
contacting a compound of formula 1-5:

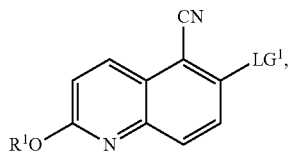

1-5 or a salt thereof, wherein:
LG¹ is a suitable leaving group; and
R¹ is a suitable oxygen protecting group;
with a compound of formula 1-6:

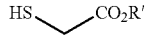

1-6 wherein:
R' is hydrogen or optionally substituted $C_{1-6}$ aliphatic or aryl;
to thereby afford the compound of formula 1-7, or a salt thereof.

In some embodiments of formula 1-7, R¹ is benzyl.

In some embodiments, R' is hydrogen or optionally substituted $C_{1-6}$ aliphatic or aryl. In some embodiments, R' is hydrogen. In some embodiments, R' is optionally substituted $C_{1-6}$ aliphatic. In some embodiments, R' is optionally substituted methyl. In some embodiments, R' is optionally substituted ethyl. In some embodiments, R' is optionally substituted propyl. In some embodiments, R' is optionally substituted butyl. In some embodiments, R' is optionally substituted pentyl. In some embodiments, R' is optionally substituted hexyl. In some embodiments, R' is methyl. In some embodiments, R' is ethyl. In some embodiments, R' is propyl. In some embodiments, R' is butyl. In some embodiments, R' is pentyl. In some embodiments, R' is hexyl. In some embodiments, R' is aryl.

In some embodiments, step S-5 is conducted in the presence of a base. In some embodiments, step S-5 is conducted in the presence of an inorganic base. In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is optionally substituted $C_{1-6}$ aliphatic or aryl. In some embodiments, the base is an alkoxide such as LiOR, NaOR, or KOR, wherein R is optionally substituted $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, an R' group of a compound of formula 1-6 and an R group of a base of formula LiOR, NaOR, or KOR are different. In some embodiments, an R' group of a compound of formula 1-6 and an R group of a base of formula LiOR, NaOR, or KOR are the same. In some embodiments, an R' group of a compound of formula 1-6, and an R group of a base of formula LiOR are the same. In some embodiments, an R' group of a compound of formula 1-6, and an R group of a base of formula NaOR are the same. In some embodiments, an R' group of a compound of formula 1-6, and an R group of a base of formula KOR are the same.

In some embodiments, a compound of formula 1-6 is

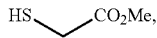

and the base is LiOMe. In some embodiments, a compound of formula 1-6 is

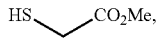

and the base is NaOMe. In some embodiments, a compound of formula 1-6 is

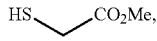

and the base is KOMe.

In some embodiments, a compound of formula 1-6 is

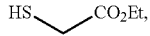

and the base is LiOEt. In some embodiments, a compound of formula 1-6 is

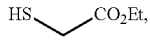

and the base is NaOEt. In some embodiments, a compound of formula 1-6 is

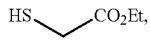

and the base is KOEt.

In some embodiments, a compound of formula 1-6 is

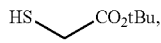

and the base is LiOtBu. In some embodiments, a compound of formula 1-6 is

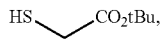

and the base is NaOtBu. In some embodiments, a compound of formula 1-6 is

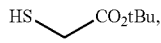

and the base is KOtBu.

In some embodiments, step S-5 is conducted in a solvent. In some embodiments, the solvent comprises a polar protic solvent. In some embodiments, the solvent comprises ROH, wherein R is as defined above and described herein. In some embodiments, the solvent comprises ROH, wherein R is optionally substituted $C_{1-6}$ aliphatic or aryl. In some embodiments, the base is added to the reaction mixture in the solvent. In some embodiments, the base is added in a solvent of formula ROH, wherein R is $C_{1-6}$ aliphatic. In some embodiments, the base is added in methanol. In some embodiments, the base is added in ethanol. In some embodiments, the base is added in tert-butanol. In some embodiments, the R group of a base of formula LiOR and a solvent of formula ROH are different. In some embodiments, the R group of a base of formula NaOR and a solvent of formula ROH are different. In some embodiments, the R group of a base of formula KOR and a solvent of formula ROH are different.

In some embodiments, the R group of a base of formula LiOR and a solvent of formula ROH are the same. In some embodiments, the R group of a base of formula NaOR and a solvent of formula ROH are the same. In some embodiments, the R group of a base of formula KOR and a solvent of formula ROH are the same. In some embodiments, the base is LiOMe and is added in methanol. In some embodiments, the base is NaOMe and is added in methanol. In some embodiments, the base is KOMe and is added in methanol. In some embodiments, the base is LiOEt and is added in ethanol. In some embodiments, the base is NaOEt and is added in ethanol. In some embodiments, the base is KOEt and is added in ethanol. In some embodiments, the base is LiOtBu and is added in tert-butanol. In some embodiments, the base is NaOtBu and is added in tert-butanol. In some embodiments, the base is KOtBu and is added in tert-butanol.

In some embodiments, step S-5 is conducted in the presence of a solvent. In some embodiments, step S-5 is conducted in the presence of a polar aprotic solvent. In some embodiments, the polar aprotic solvent is THF.

In some embodiments, step S-5 comprises mixing a compound of formula 1-5 and a compound of formula 1-6 (e.g., 2-mercaptoacetate) in a solvent (e.g., THF). In some embodiments, a base (e.g., NaOMe) in a solvent (e.g., methanol) is added to the mixture. In some embodiments, a base (e.g., NaOMe) in a solvent (e.g., methanol) is added to the mixture at a rate to maintain a reaction temperature. In some embodiments, a reaction temperature is between about 20° C. and about 25° C. In some embodiments, after a base (e.g., NaOMe) in a solvent (e.g., methanol) is added to the mixture, the reaction mixture is heated. In some embodiments, the reaction mixture is heated to reflux. In some embodiments, the reaction mixture is heated to reflux for about 2 to about 4 hrs. In some embodiments, the reaction mixture is heated to reflux for about 1 to about 6 hrs.

In some embodiments, the present invention provides a method for preparing a compound of formula 1-7:

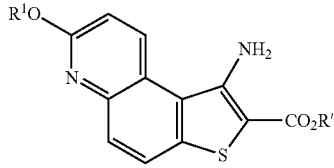

1-7 or a salt thereof, wherein:
R' is hydrogen or optionally substituted $C_{1-6}$ aliphatic or aryl; and
$R^1$ is a suitable oxygen protecting group;
comprising the step of reacting a compound of formula 1-5:

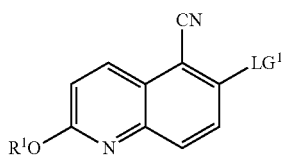

1-5 or a salt thereof, wherein:
$LG^1$ is a suitable leaving group;
with a compound of formula 1-6:

1-6 under suitable reaction conditions to afford the compound of formula 1-7, or a salt thereof.

In some embodiments, the present invention provides a method for preparing a compound of formula 1-7:

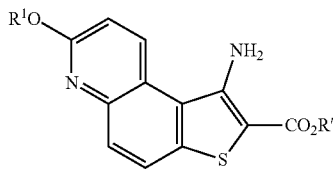

1-7 or a salt thereof, wherein:
R' is hydrogen or optionally substituted $C_{1-6}$ aliphatic or aryl; and
$R^1$ is a suitable oxygen protecting group;
comprising the steps of
(a) providing a compound of formula 1-5:

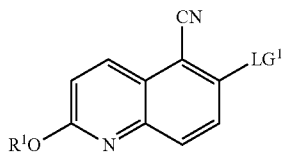

1-5 or a salt thereof, wherein
$LG^1$ is a suitable leaving group; and
(b) reacting the compound of formula 1-5, or a salt thereof, with a compound of formula 1-6:

1-6 to thereby afford the compound of formula 1-7, or a salt thereof.

Step S-6 of Scheme 2

At step S-6 of Scheme 2, a compound of formula 1-7 is coupled with a compound of formula 1-8:

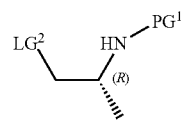

1-8 to thereby afford a compound of formula 1-9. In some embodiments, a compound of formula 1-7 is coupled to a compound of formula 1-8 via nucleophilic displacement of $LG^2$ by the amine of a compound of formula 1-7.

In some embodiments, at step S-6 of Scheme 2, a compound of 1-9 is prepared by a process comprising:
contacting a compound of formula 1-7:

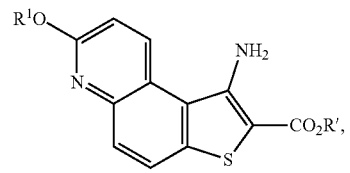

1-7 or a salt thereof, wherein:
R' is hydrogen or optionally substituted $C_{1-6}$ aliphatic or aryl; and
$R^1$ is a suitable oxygen protecting group;
with a compound of formula 1-8:

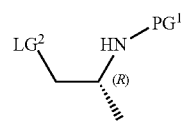

1-8 or a salt thereof, wherein:
$LG^2$ is a suitable leaving group; and
$PG^1$ is a suitable nitrogen protecting group;
to thereby afford the compound of formula 1-9, or a salt thereof.

$LG^2$ is a suitable leaving group as defined above and herein for $LG^1$. In some embodiments, $LG^2$ is sulfonate ester. In some embodiments of formula 1-8, $LG^2$ and the nitrogen atom cyclize to form a sulfamate. Accordingly, in some embodiments, formula 1-8 has the structure:

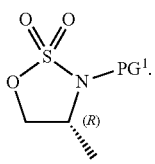

A PG¹ group of a compound of formula 1-8 is a suitable nitrogen protecting group. Various methods and conditions for protecting amines are known in the chemical arts. For example, suitable nitrogen protecting groups are well known in the art and include those described in detail in *Protecting Groups in Organic Synthesis*, T. W. Green and P. G. M. Wuts, 3rd edition, John Wiley & Sons, 1999, the entirety of which is incorporated herein by reference. Suitable nitrogen protecting groups, taken with the —NH— moiety to which it is attached, include, but are not limited to, aralkylamines, carbamates, allyl amines, amides, and the like. Examples of PG¹ groups of a compound of formula 1-8 include t-butyloxycarbonyl (Boc), p-methoxybenzyloxycarbonyl (PMB), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like.

In some embodiments, PG¹ is t-butyloxycarbonyl (Boc). In certain embodiments, PG¹ is Boc, and the reagent used to install PG¹ is di-tert-butyl dicarbonate.

In some embodiments, step S-6 of Scheme 2 is conducted in the presence of a base. In some embodiments, the base is an inorganic base. In some embodiments, the base is NaH.

In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is $C_{1-6}$ aliphatic or aryl. In some embodiments, the base is an alkoxide such as LiOR, NaOR, or KOR, wherein R is $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, step S-6 is conducted in the presence of a solvent. In some embodiments, the solvent comprises N-methyl-2-pyrrolidone (NMP). In some embodiments, the solvent comprises DMF. In some embodiments, the solvent comprises THF.

In some embodiments, step S-6 of Scheme 2 is conducted in the presence of a base and a solvent. In some embodiments, the base is LiOtBu and the solvent comprises NMP. In some embodiments, the base is NaH and the solvent comprises DMF.

In some embodiments, step S-6 of Scheme 2 comprises mixing a compound of formula 1-7, a compound of formula 1-8, and a solvent (e.g., NMP). In some embodiments, the resulting mixture is cooled to a lower temperature. In some embodiments, a lower temperature is between about 0° C. and −25° C. In some embodiments, a lower temperature is between about −10° C. and −15° C. In some embodiments, a base (e.g., LiOtBu) in a solvent (e.g, THF) is added. In some embodiments, the addition of a base (e.g., LiOtBu) in a solvent (e.g, THF) is over a period of about 90 mins. In some embodiments, a resulting reaction mixture is agitated for a period of time. In some embodiments, the period of time is between about 15 mins to about 60 mins. In some embodiments, the period of time is about 30 mins. In some embodiments, while a resulting reaction mixture is agitated, the temperature is maintained.

In some embodiments, a compound of formula 1-9 is taken into step S-7 of Scheme 2 without being isolated. In some embodiments, a compound of formula 1-9 is isolated after step S-6 of Scheme 2.

In some embodiments of formula 1-9, R¹ is benzyl.

In some embodiments of formula 1-9, R' is $C_{1-6}$ aliphatic. In some such embodiments, R' is methyl.

In some embodiments, the present invention provides a method for preparing a compound of formula 1-9:

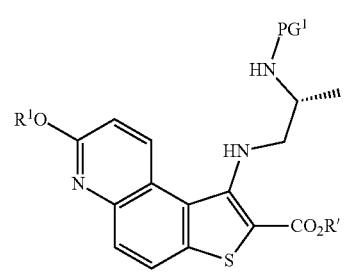

or a salt thereof, wherein:
PG¹ is a suitable nitrogen protecting group;
R' is hydrogen or optionally substituted $C_{1-6}$ aliphatic or aryl; and
R¹ is a suitable oxygen protecting group;
comprising the step of reacting a compound of formula 1-7:

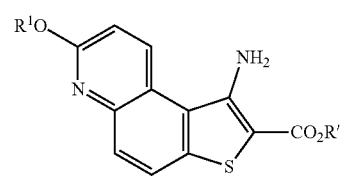

or a salt thereof;
with a compound of formula 1-8:

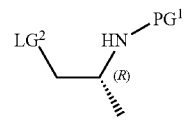

or a salt thereof, wherein,
LG² is a suitable leaving group;
under suitable reaction conditions to afford the compound of formula 1-9, or a salt thereof.

In some embodiments, the present invention provides a method for preparing a compound of formula 1-9:

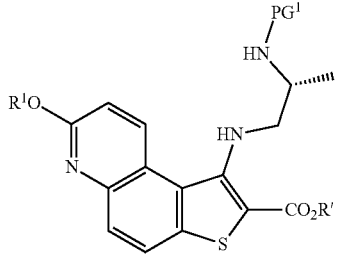

1-9 or a salt thereof, wherein:
PG¹ is a suitable nitrogen protecting group;
R' is hydrogen or optionally substituted $C_{1-6}$ aliphatic or aryl; and
R¹ is a suitable oxygen protecting group;
comprising the steps of
(a) providing a compound of formula 1-7

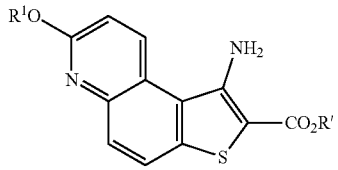

1-7 or a salt thereof, and
(b) reacting the compound of formula 1-7, or a salt thereof, with a compound of formula 1-8:

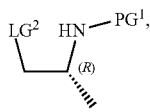

1-8 or a salt thereof,
to thereby afford the compound of formula 1-9, or a salt thereof.

In some embodiments, the present invention provides a method for preparing a compound of formula 1-9:

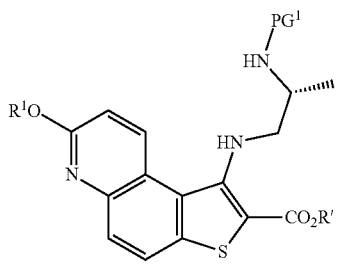

1-9 or a salt thereof, wherein:
PG¹ is a suitable nitrogen protecting group;
R' is hydrogen or optionally substituted $C_{1-6}$ aliphatic or aryl; and
R¹ is a suitable oxygen protecting group;
comprising the step of reacting a compound of formula 1-7:

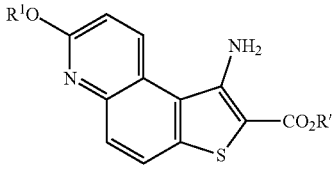

1-7 or a salt thereof;
with a compound of formula 1-8:

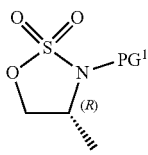

1-8 under suitable reaction conditions to afford the compound of formula 1-9, or a salt thereof.

In some embodiments, the present invention provides a method for preparing a compound of formula 1-9:

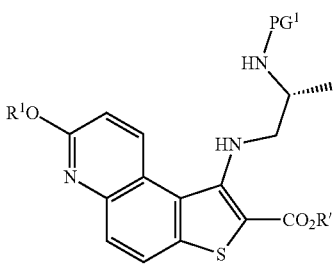

1-9 or a salt thereof, wherein:
PG¹ is a suitable nitrogen protecting group;
R' is hydrogen or optionally substituted $C_{1-6}$ aliphatic or aryl; and
R¹ is a suitable oxygen protecting group;
comprising the steps of
(a) providing a compound of formula 1-7

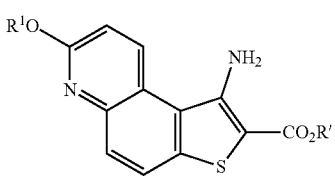

1-7 or a salt thereof, and
(b) reacting the compound of formula 1-7, or a salt thereof, with a compound of formula 1-8:

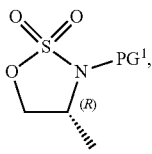

to thereby afford the compound of formula 1-9, or a salt thereof.

Step S-6 of Scheme 2-a

At step S-6 of Scheme 2-a, a compound of formula 1-7 is coupled with a compound of formula 1-8a:

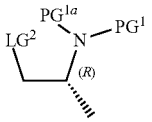

wherein:
$LG^2$ is a suitable leaving group; and
each of $PG^1$ and $PG^{1a}$ is independently a suitable nitrogen protecting group;
to thereby afford a compound of formula 1-9a.

In some embodiments, a compound of formula 1-7 is coupled to a compound of formula 1-8a via nucleophilic displacement of $LG^2$ by the amine of a compound of formula 1-7.

In some embodiments, at step S-6 of Scheme 2-a, a compound of formula 1-9a is prepared by a process comprising:
contacting a compound of formula 1-7:

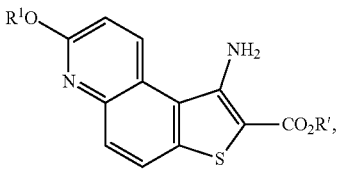

or a salt thereof, wherein:
R' is hydrogen or optionally substituted $C_{1-6}$ aliphatic or aryl; and
$R^1$ is a suitable oxygen protecting group;
with a compound of formula 1-8a:

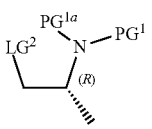

or a salt thereof, wherein:
$LG^2$ is a suitable leaving group; and
each of $PG^1$ and $PG^{1a}$ is independently a suitable nitrogen protecting group;
to thereby afford the compound of formula 1-9a, or a salt thereof.

$LG^2$ is a suitable leaving group as defined above and herein for $LG^1$. In some embodiments, $LG^2$ is sulfonate ester. In some embodiments of formula 1-8a, $LG^2$ and $PG^{1a}$ cyclize to form a sulfamate. Accordingly, in some embodiments, formula 1-8a has the structure:

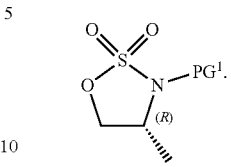

Each of the $PG^1$ and $PG^{1a}$ groups of a compound of formula 1-8a is independently a suitable nitrogen protecting group. Examples of suitable nitrogen protecting groups include t-butyloxycarbonyl (Boc), p-methoxybenzyloxycarbonyl (PMB), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like.

In some embodiments, each of $PG^1$ and $PG^{1a}$ is independently t-butyloxycarbonyl (Boc). In certain embodiments, each of $PG^1$ and $PG^{1a}$ is independently Boc, and the reagent used to install each of $PG^1$ and $PG^{1a}$ is di-tert-butyl dicarbonate.

In some embodiments, step S-6 of Scheme 2-a is conducted in the presence of a base. In some embodiments, the base is an inorganic base. In some embodiments, the base is NaH.

In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is $C_{1-6}$ aliphatic or aryl. In some embodiments, the base is an alkoxide such as LiOR, NaOR, or KOR, wherein R is $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, step S-6 of Scheme 2-a is conducted in the presence of a solvent. In some embodiments, the solvent comprises N-methyl-2-pyrrolidone (NMP). In some embodiments, the solvent comprises DMF. In some embodiments, the solvent comprises THF.

In some embodiments, step S-6 of Scheme 2-a is conducted in the presence of a base and a solvent. In some embodiments, the base is LiOtBu and the solvent comprises NMP. In some embodiments, the base is NaH and the solvent comprises DMF.

In some embodiments, step S-6 of Scheme 2-a comprises mixing a compound of formula 1-7, a compound of formula 1-8a, and a solvent (e.g., NMP). In some embodiments, the resulting mixture is cooled to a lower temperature. In some embodiments, a lower temperature is between about 0° C.

and −25° C. In some embodiments, a lower temperature is between about −10° C. and −15° C. In some embodiments, a base (e.g., LiOtBu) in a solvent (e.g, THF) is added. In some embodiments, the addition of a base (e.g., LiOtBu) in a solvent (e.g, THF) is over a period of about 90 mins. In some embodiments, a resulting reaction mixture is agitated for a period of time. In some embodiments, the period of time is between about 15 mins to about 60 mins. In some embodiments, the period of time is about 30 mins. In some embodiments, while a resulting reaction mixture is agitated, the temperature is maintained.

In some embodiments, a compound of formula 1-9a is taken into step S-7 of Scheme 2-a without being isolated. In some embodiments, a compound of formula 1-9a is isolated after step S-6 of Scheme 2-a.

In some embodiments of formula 1-9a, $R^1$ is benzyl.

In some embodiments of formula 1-9a, R' is $C_{1-6}$ aliphatic. In some such embodiments, R' is methyl.

In some embodiments, the present invention provides a method for preparing a compound of formula 1-9a:

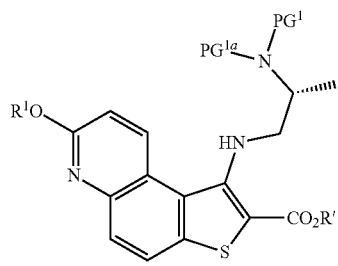

1-9a or a salt thereof, wherein:
each of $PG^1$ and $PG^{1a}$ is independently a suitable nitrogen protecting group;
R' is hydrogen or optionally substituted $C_{1-6}$ aliphatic or aryl; and
$R^1$ is a suitable oxygen protecting group;
comprising the step of reacting a compound of formula 1-7:

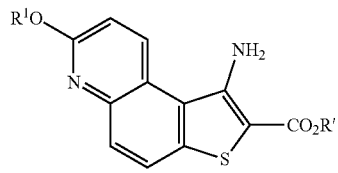

1-7 or a salt thereof;
with a compound of formula 1-8a:

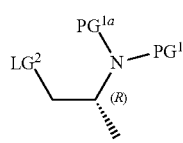

1-8a or a salt thereof, wherein,
$LG^2$ is a suitable leaving group;
under suitable reaction conditions to afford the compound of formula 1-9a, or a salt thereof.

In some embodiments, the present invention provides a method for preparing a compound of formula 1-9a:

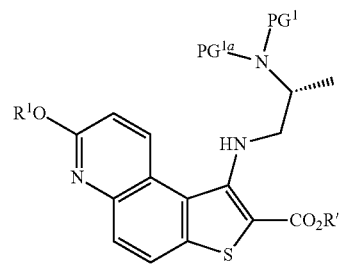

1-9a or a salt thereof, wherein:
each of $PG^1$ and $PG^{1a}$ is independently a suitable nitrogen protecting group;
R' is hydrogen or optionally substituted $C_{1-6}$ aliphatic or aryl; and
$R^1$ is a suitable oxygen protecting group;
comprising the steps of
(a) providing a compound of formula 1-7

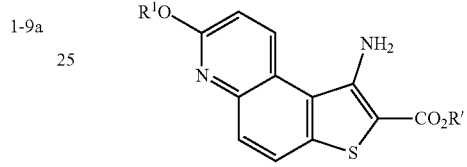

1-7 or a salt thereof, and
(b) reacting the compound of formula 1-7, or a salt thereof, with a compound of formula 1-8a:

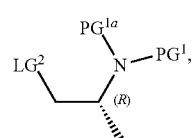

1-8a or a salt thereof, wherein
$LG^2$ is a suitable leaving group;
to thereby afford the compound of formula 1-9a, or a salt thereof.

Step S-7 of Scheme 2

At step S-7 of Scheme 2, a compound of formula 1-9 is deprotected to afford a compound of formula 1-10. In some embodiments, at step S-7 of Scheme 2, a compound of formula 1-10 is prepared by a process comprising:
contacting a compound of formula 1-9:

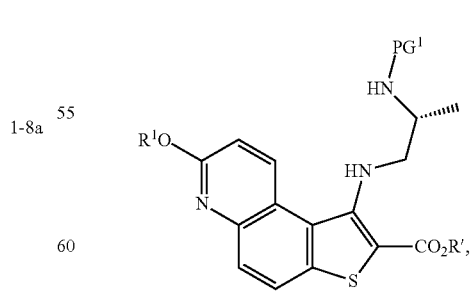

1-9 or a salt thereof, wherein:
$PG^1$ is a suitable nitrogen protecting group;
R' is hydrogen or optionally substituted $C_{1-6}$ aliphatic or aryl; and
$R^1$ is a suitable oxygen protecting group;

with an acid, to thereby afford the compound of formula 1-10, or a salt thereof.

$PG^1$ is as described above and defined herein. Various methods and conditions for deprotecting amines (e.g., $PG^1$) are known in the chemical arts. For example, methods and conditions for deprotecting amines are well known in the art and include those described in detail in *Protecting Groups in Organic Synthesis*, T. W. Green and P. G. M. Wuts, $3^{rd}$ edition, John Wiley & Sons, 1999, the entirety of which is incorporated herein by reference. In some embodiments of formula 1-9, $PG^1$ is Boc.

In some embodiments, $PG^1$ of formula 1-9 is removed by acid. In some embodiments, a wide variety of acids are useful for removing nitrogen protecting groups that are acid labile. In some embodiments, the acid is a Lewis acid. In some embodiments, the acid is a Bronsted acid.

In some embodiments, the acid is an inorganic acid. In some embodiments, the acid is HCl. In some embodiments, the inorganic acid is in a solvent. In some embodiments, the inorganic acid is in water. In some embodiments, the inorganic acid is in isopropanol. In some embodiments, HCl is in isopropanol.

In some embodiments, $PG^1$ of a compound of formula 1-9 is removed with a sulfonic acid, for example methanesulfonic acid, benzenesulfonic acid (BSA), or p-toluenesulfonic acid (PTSA). In some embodiments, $PG^1$ of formula 1-9 is removed with methanesulfonic acid. In some embodiments, $PG^1$ of formula 1-9 is removed with BSA. In some embodiments, $PG^1$ of formula 1-9 is removed with PTSA.

$R^1$ is as described above and defined herein. In some embodiments, $R^1$ is a suitable oxygen protecting group. Various methods and conditions for deprotecting alcohols are known in the chemical arts. For example, methods and conditions for deprotecting alcohols are well known in the art and include those described in detail in *Protecting Groups in Organic Synthesis*, T. W. Green and P. G. M. Wuts, $3^{rd}$ edition, John Wiley & Sons, 1999, the entirety of which is incorporated herein by reference.

In some embodiments of formula 1-9, $R^1$ is benzyl. In some embodiments, $R^1$ of a compound of formula 1-9 is removed by acid. In some embodiments, a wide variety of acids are useful for removing oxygen protecting groups that are acid labile. In some embodiments, the acid is a Lewis acid. In some embodiments, the acid is a Bronsted acid.

In some embodiments, $R^1$ of a compound of formula 1-9 is removed with a sulfonic acid, for example methanesulfonic acid, benzenesulfonic acid (BSA), or p-toluenesulfonic acid (PTSA). In some embodiments, $R^1$ of a compound of formula 1-9 is removed with methanesulfonic acid. In some embodiments, $R^1$ of a compound of formula 1-9 is removed with BSA. In some embodiments, $R^1$ of a compound of formula 1-9 is removed with PTSA.

In some embodiments, step S-7 of Scheme 2 is conducted in the presence of a solvent. In some embodiments, the solvent comprises a polar protic solvent. In some embodiments, the solvent comprises methanol. In some embodiments, the solvent comprises a polar aprotic solvent. In some embodiments, the solvent comprises MeCN. In some embodiments, the solvent comprises a polar protic solvent and a polar aprotic solvent. In some embodiments, the solvent comprises methanol and MeCN.

In some embodiments, a compound of formula 1-9 is isolated after step S-6 of Scheme 2. In some embodiments, step S-7 of Scheme 2 comprises mixing a compound of formula 1-9 in a solvent (e.g., methanol) and an acid (e.g., HCl) in a solvent (e.g., isopropanol). In some embodiments, the reaction mixture is agitated for an amount of time. In some embodiments, the reaction mixture is agitated for between about 5 mins and about 1 hr. In some embodiments, the reaction mixture is agitated for about 15 mins. In some embodiments, the reaction mixture is additionally heated and agitated for an amount of time. In some embodiments, the reaction mixture is additionally heated to reflux and agitated for an amount of time. In some embodiments, the reaction mixture is additionally heated to reflux and agitated for between about 6 hr and about 36 hr. In some embodiments, the reaction mixture is additionally heated to reflux and agitated for about 20 h.

In some embodiments, at step S-7 of Scheme 2, a compound of formula 1-10 is prepared in a "one pot" reaction, such "one pot" reaction comprising coupling a compound of formula 1-7 with a compound of formula 1-8 to thereby afford a compound of formula 1-9, followed by in situ deprotection, thereby resulting in a compound of formula 1-10. For instance, in some embodiments, step S-7 of Scheme 2 comprises an addition of a solvent (e.g., MeCN) to the crude product of step S-6 of Scheme 2. In some embodiments, step S-7 of Scheme 2 comprises an addition of an acid (e.g., BSA) in a solvent (e.g., methanol) to the crude product of step S-6 of Scheme 2. In some embodiments, an addition of an acid (e.g., BSA) in a solvent (e.g., methanol) is performed dropwise. In some embodiments, an addition of an acid (e.g., BSA) in a solvent (e.g., methanol) is performed at between about 65° C. and 70° C. In some embodiments, the reaction is agitated for an amount of time. In some embodiments, the reaction is agitated for between about 6 hr and about 24 hr. In some embodiments, the reaction is agitated for an amount of time. In some embodiments, the reaction is agitated for about 16 h.

In certain embodiments, each of $PG^1$ and $R^1$ is removed by HCl. In some such embodiments, the compound of formula 1-10 is isolated as a HCl salt.

In certain embodiments, each of $PG^1$ and $R^1$ is removed by BSA. In some such embodiments, the compound of formula 1-10 is isolated as a benzene sulfonic acid salt.

In some embodiments, the present invention provides a method for preparing a compound of formula 1-10:

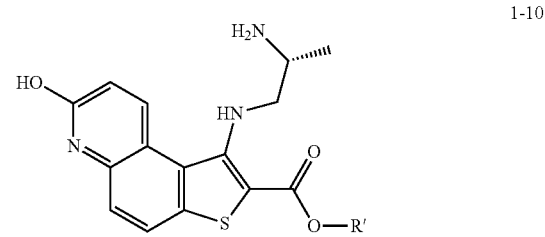

1-10 or a salt thereof, wherein:
R' is hydrogen or optionally substituted $C_{1-6}$ aliphatic or aryl;
comprising the step of reacting a compound of formula 1-9:

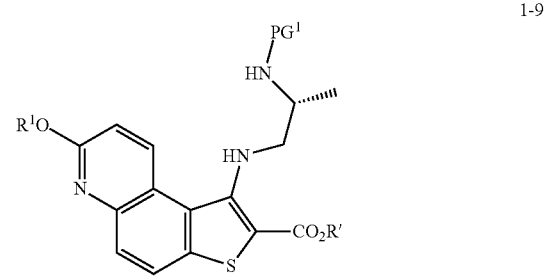

1-9 or a salt thereof, wherein:
$R^1$ is a suitable oxygen protecting group; and
$PG^1$ is a suitable nitrogen protecting group;
under suitable reaction conditions to afford the compound of formula 1-10, or a salt thereof.

In some embodiments, the present invention provides a method for preparing a compound of formula 1-10:

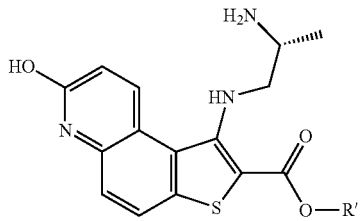

or a salt thereof, wherein:
R' is hydrogen or optionally substituted $C_{1-6}$ aliphatic or aryl;
comprising the steps of:
(a) reacting a compound of formula 1-7:

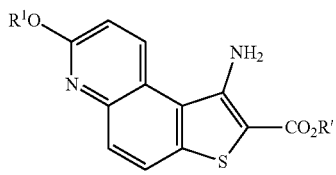

or a salt thereof, wherein:
$R^1$ is a suitable oxygen protecting group;
with a compound of formula 1-8:

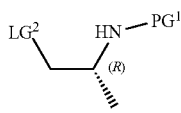

or a salt thereof, wherein:
$PG^1$ is a suitable nitrogen protecting group; and
$LG^2$ is a suitable leaving group;
under suitable reaction conditions to afford a compound of formula 1-9:

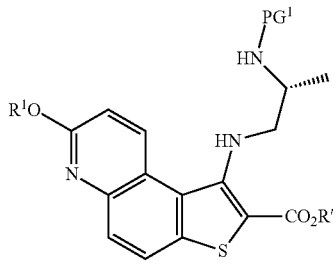

or a salt thereof; and
(b) reacting the compound of formula 1-9 under suitable reaction conditions to afford the compound of formula 1-10, or a salt thereof.
Step S-7 of Scheme 2-a
At step S-7 of Scheme 2-a, a compound of formula 1-9a is deprotected to afford a compound of formula 1-10. In some embodiments, at step S-7 of Scheme 2-a, a compound of formula 1-10 is prepared by a process comprising: contacting a compound of formula 1-9a:

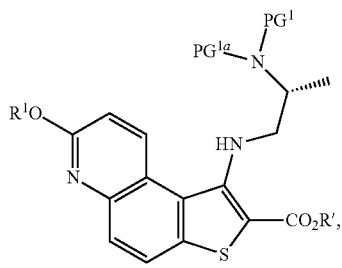

or a salt thereof, wherein:
each of $PG^1$ and $PG^{1a}$ is independently a suitable nitrogen protecting group;
R' is hydrogen or optionally substituted $C_{1-6}$ aliphatic or aryl; and
$R^1$ is a suitable oxygen protecting group;
with an acid, to thereby afford the compound of formula 1-10, or a salt thereof.

Each of $PG^1$ and $PG^{1a}$ is as described above and defined herein. Various methods and conditions for deprotecting amines (e.g., $PG^1$ or $PG^{1a}$) are known in the chemical arts. For example, methods and conditions for deprotecting amines are well known in the art and include those described in detail in *Protecting Groups in Organic Synthesis*, T. W. Green and P. G. M. Wuts, $3^{rd}$ edition, John Wiley & Sons, 1999, the entirety of which is incorporated herein by reference. In some embodiments of formula 1-9a, $PG^1$ is Boc.

In some embodiments, each of $PG^1$ and $PG^{1a}$ of formula 1-9a is removed by acid. In some embodiments, a wide variety of acids are useful for removing nitrogen protecting groups that are acid labile. In some embodiments, an acid is a Lewis acid. In some embodiments, an acid is a Bronsted acid.

In some embodiments, the acid is an inorganic acid. In some embodiments, the acid is HCl. In some embodiments, the inorganic acid is in a solvent. In some embodiments, the inorganic acid is in water. In some embodiments, the inorganic acid is in isopropanol. In some embodiments, HCl is in isopropanol.

In some embodiments, each of $PG^1$ and $PG^{1a}$ of formula 1-9a is removed with a sulfonic acid, for example methanesulfonic acid, benzenesulfonic acid (BSA), or p-toluenesulfonic acid (PTSA). In some embodiments, each of $PG^1$ and $PG^{1a}$ of formula 1-9a is removed with methanesulfonic acid. In some embodiments, each of $PG^1$ and $PG^{1a}$ of formula 1-9a is removed with BSA. In some embodiments, each of $PG^1$ and $PG^{1a}$ of formula 1-9a is removed with PTSA.

In some embodiments, each of $PG^1$ and $PG^{1a}$ of formula 1-9a is removed orthogonally. For example, in some embodiments, $PG^1$ and $PG^{1a}$ are not the same and are removed under different conditions. In some embodiments, $PG^1$ is removed under acidic conditions, whereas $PG^{1a}$ is removed under catalytic hydrogenation. It will be appreciated that a number of protecting groups can be used and removed in whichever order is desirable under the conditions.

$R^1$ is as described above and defined herein. In some embodiments, $R^1$ is a suitable oxygen protecting group. Various methods and conditions for deprotecting alcohols are known in the chemical arts. For example, methods and conditions for deprotecting alcohols are well known in the art and include those described in detail in *Protecting Groups in Organic Synthesis*, T. W. Green and P. G. M. Wuts, $3^{rd}$ edition, John Wiley & Sons, 1999, the entirety of which is incorporated herein by reference.

In some embodiments of formula 1-9a, $R^1$ is benzyl.

In some embodiments, $R^1$ of a compound of formula 1-9 is removed by acid. In some embodiments, a wide variety of acids are useful for removing oxygen protecting groups that are acid labile. In some embodiments, the acid is a Lewis acid. In some embodiments, the acid is a Bronsted acid.

In some embodiments, $R^1$ of a compound of formula 1-9a is removed with a sulfonic acid, for example methanesulfonic acid, benzenesulfonic acid (BSA), or p-toluenesulfonic acid (PTSA). In some embodiments, $R^1$ of a compound of formula 1-9a is removed with methanesulfonic acid. In some embodiments, $R^1$ of a compound of formula 1-9a is removed with BSA. In some embodiments, $R^1$ of a compound of formula 1-9a is removed with PTSA.

In some embodiments, step S-7 of Scheme 2-a is conducted in the presence of a solvent. In some embodiments, the solvent comprises a polar protic solvent. In some embodiments, the solvent comprises methanol. In some embodiments, the solvent comprises a polar aprotic solvent. In some embodiments, the solvent comprises MeCN. In some embodiments, the solvent comprises a polar protic solvent and a polar aprotic solvent. In some embodiments, the solvent comprises methanol and MeCN.

In some embodiments, a compound of formula 1-9a is isolated after step S-6 of Scheme 2-a. In some embodiments, step S-7 of Scheme 2-a comprises mixing a compound of formula 1-9a in a solvent (e.g., methanol) and an acid (e.g., HCl) in a solvent (e.g., isopropanol). In some embodiments, the reaction mixture is agitated for an amount of time. In some embodiments, the reaction mixture is agitated for between about 5 mins and about 1 hr. In some embodiments, the reaction mixture is agitated for about 15 mins. In some embodiments, the reaction mixture is additionally heated and agitated for an amount of time. In some embodiments, the reaction mixture is additionally heated to reflux and agitated for an amount of time. In some embodiments, the reaction mixture is additionally heated to reflux and agitated for between about 6 hr and about 36 hr. In some embodiments, the reaction mixture is additionally heated to reflux and agitated for about 20 h.

In some embodiments, at step S-7 of Scheme 2, a compound of formula 1-10 is prepared in a "one pot" reaction, such "one pot" reaction comprising coupling a compound of formula 1-7 with a compound of formula 1-8a to thereby afford a compound of formula 1-9a, followed by in situ deprotection, thereby resulting in a compound of formula 1-10. For instance, in some embodiments, step S-7 of Scheme 2-a comprises an addition of a solvent (e.g., MeCN) to the crude product of step S-6 of Scheme 2-a. In some embodiments, step S-7 of Scheme 2-a comprises an addition of an acid (e.g., BSA) in a solvent (e.g., methanol) to the crude product of step S-6 of Scheme 2-a. In some embodiments, an addition of an acid (e.g., BSA) in a solvent (e.g., methanol) is performed dropwise. In some embodiments, an addition of an acid (e.g., BSA) in a solvent (e.g., methanol) is performed at between about 65° C. and 70° C. In some embodiments, the reaction is agitated for an amount of time. In some embodiments, the reaction is agitated for between about 6 hr and about 24 hr. In some embodiments, the reaction is agitated for an amount of time. In some embodiments, the reaction is agitated for about 16 h.

In certain embodiments, each of $PG^1$ and $R^1$ is removed by HCl. In some such embodiments, the compound of formula 1-10 is isolated as a HCl salt.

In certain embodiments, each of $PG^1$ and $R^1$ is removed by BSA. In some such embodiments, the compound of formula 1-10 is isolated as a benzene sulfonic acid salt.

In some embodiments, the present invention provides a method for preparing a compound of formula 1-10:

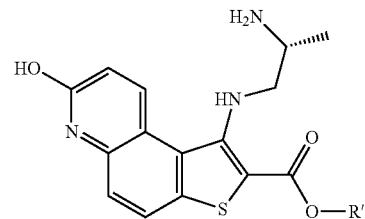

1-10 or a salt thereof, wherein:

R' is hydrogen or optionally substituted $C_{1-6}$ aliphatic or aryl;

comprising the step of reacting a compound of formula 1-9a:

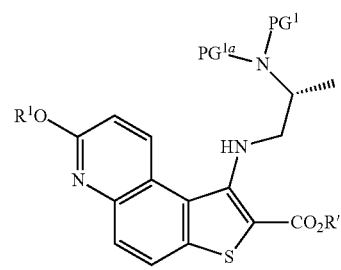

1-9a or a salt thereof, wherein:

$R^1$ is a suitable oxygen protecting group; and each of $PG^1$ and $PG^{1a}$ is independently a suitable nitrogen protecting group;

under suitable reaction conditions to afford the compound of formula 1-10, or a salt thereof.

In some embodiments, the present invention provides a method for preparing a compound of formula 1-10:

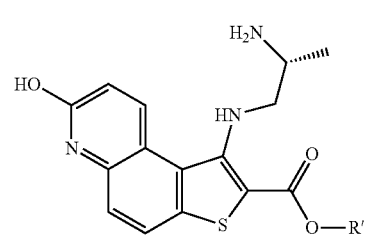

1-10 or a salt thereof, wherein:

R' is hydrogen or optionally substituted $C_{1-6}$ aliphatic or aryl;

comprising the steps of:

(a) reacting a compound of formula 1-7:

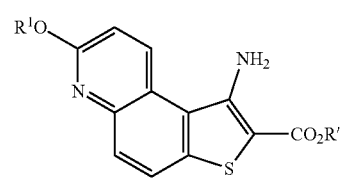

1-7 or a salt thereof, wherein:

$R^1$ is a suitable oxygen protecting group;

with a compound of formula 1-8a:

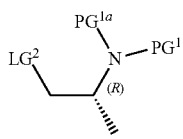

wherein:
each of PG¹ and PG¹ᵃ is independently a suitable nitrogen protecting group; and
LG² is a suitable leaving group;
under suitable reaction conditions to afford a compound of formula 1-9a:

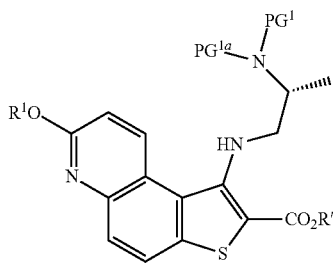

or a salt thereof; and
(b) reacting the compound of formula 1-9a under suitable reaction conditions to afford the compound of formula 1-10, or a salt thereof.

Step S-8 of Scheme 2 or Scheme 2-a

At step S-8, a compound of formula 1-10 undergoes a cyclization to form a compound of formula 1-11.

In some embodiments, step S-8 is conducted in the presence of a base.

In some embodiments, the present invention provides a method for preparing a compound of formula 1-11:

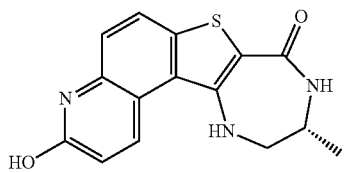

or a salt thereof,
comprising the steps of
(a) providing a compound of formula 1-10

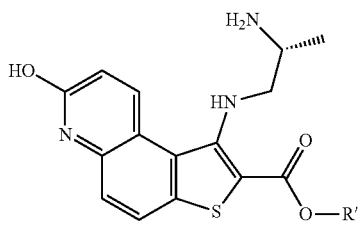

or a salt thereof, and
(b) reacting the compound of formula 1-10, or a salt thereof, with a base, to thereby afford the compound of formula 1-11, or a salt thereof.

In some embodiments, the base is an inorganic base. In some embodiments, the base is an alkali hydroxide. In some embodiments, the base is LiOH. In some embodiments, the base is NaOH. In some embodiments, the base is KOH. In some embodiments, the base is a carbonate. In some embodiments, the base is $K_2CO_3$. In some embodiments, the base is $Na_2CO_3$. In some embodiments, the base is a bicarbonate. In some embodiments, the base is $KHCO_3$. In some embodiments, the base is $NaHCO_3$. In some embodiments, the base is a phosphate. In some embodiments, the base is $Na_3PO_4$. In some embodiments, the base is $K_3PO_4$.

In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is $C_{1-6}$ aliphatic or aryl. In some embodiments, the base is an alkoxide such as LiOR, NaOR, or KOR, wherein R is $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, the base is an organic base. In some embodiments, the base is an amine base. In some embodiments, the base is trimethylamine. In some embodiments, the base is diisopropylethylamine (DIEA). In some embodiments, the base is triethylamine. In some embodiments, the base is DBU.

In some embodiments, step S-8 is conducted in the presence of a solvent. In some embodiments, the solvent comprises a polar protic solvent. In some embodiments, the solvent comprises methanol.

In some embodiments, step S-8 comprises mixing a compound of formula 1-10 and a solvent (e.g., methanol). In some embodiments, step S-7 comprises an addition of a base (e.g., DBU). In some embodiments, the base (e.g., DBU) is added dropwise. In some embodiments, the base (e.g., DBU) is added at a rate to maintain the temperature of the mixture. In some embodiments, the base (e.g., DBU) is added at room temperature. In some embodiments, the base (e.g., DBU) is added to the mixture of a compound of formula 1-10 and a solvent (e.g., methanol) at a temperature between about 10° C. and about 45° C. In some embodiments, the base (e.g., DBU) is added to the mixture of a compound of formula 1-10 and a solvent (e.g., methanol) at a temperature between about 20° C. and about 30° C. In some embodiments, the base (e.g., DBU) is added to the mixture of a compound of formula 1-10 and a solvent (e.g., methanol) at a temperature between about 20° C. and about 25° C. In some embodiments, the reaction mixture is heated to an elevated temperature and agitated for a period of time. In some embodiments, an elevated temperature is between about 50° C. and about 85° C. In some embodiments, an elevated temperature is between about 60° C. and about 70° C. In some embodiments, an elevated temperature is between about 60° C. and about 65° C. In some embodiments, a period of time is between about 12 h to about 48 h. In some embodiments, a period of time is about 40 h. In some embodiments, a period of time is about 24 h to about 30 h.

In some embodiments, the present invention provides a method for preparing a compound of formula 1-11:

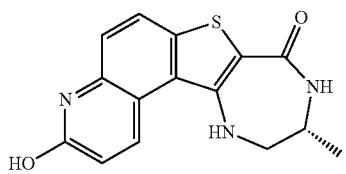

or a salt thereof;
comprising the step of reacting a compound of formula 1-10:

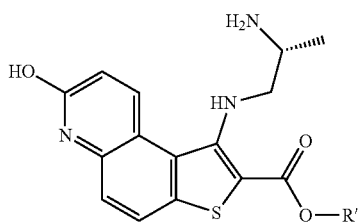

or a salt thereof, wherein:
R' is hydrogen or optionally substituted $C_{1-6}$ aliphatic or aryl; and under suitable reaction conditions to afford the compound of formula 1-11, or a salt thereof.

Step S-9 of Scheme 2 or Scheme 2-a

At step S-9, a compound of formula 1-11 is coupled with a compound of formula 1-12:

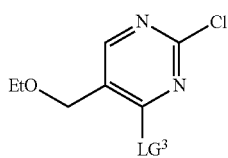

to thereby afford compound I. In some embodiments, a compound of formula 1-11 is coupled with a compound of formula 1-12 via nucleophilic displacement of $LG^3$ by the hydroxyl group of a compound of formula 1-11 to afford compound I.

$LG^3$ is a suitable leaving group as defined above and herein for $LG^1$ and $LG^2$. In some embodiments, $LG^3$ is a halogen. In some embodiments, $LG^3$ is chloro. In some embodiments, $LG^3$ is bromo. In some embodiments, $LG^3$ is iodo.

In some embodiments, step S-9 is conducted in the presence of a base. In some embodiments, the base is an inorganic base. In some embodiments, the base is a carbonate. In some embodiments, the base is $K_2CO_3$. In some embodiments, the base is $Na_2CO_3$. In some embodiments, the base is a bicarbonate. In some embodiments, the base is $KHCO_3$. In some embodiments, the base is $NaHCO_3$. In some embodiments, the base is a phosphate. In some embodiments, the base is $Na_3PO_4$. In some embodiments, the base is $K_3PO_4$.

In some embodiments, the base is a hydroxide base. In some embodiments, the base is LiOH. In some embodiments, the base is NaOH. In some embodiments, the base is KOH. In some embodiments, the base is RbOH. In some embodiments, the base is CsOH.

In some embodiments, the base is LiOR, NaOR, or KOR, wherein R is as defined above and described herein. In some embodiments, the base is an alkoxide. For instance, in some embodiments, the base is LiOR, NaOR, or KOR, wherein R is $C_{1-6}$ aliphatic or aryl. In some embodiments, the base is an alkoxide such as LiOR, NaOR, or KOR, wherein R is $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, the base is an organic base. In some embodiments, the base is an amine base. In some embodiments, the base is trimethylamine. In some embodiments, the base is DIEA. In some embodiments, the base is triethylamine. In some embodiments, the base is DBU.

In some embodiments, step S-9 is conducted in the presence of a solvent. In some embodiments, the solvent comprises a polar aprotic solvent. In some embodiments, the solvent comprises DMSO.

In some embodiments, step S-9 comprises mixing a compound of formula 1-11, a compound of formula 1-12 (e.g., wherein $LG^3$ is chloro), a base (e.g., $K_2CO_3$) and a solvent (e.g., DMSO). In some embodiments, the reaction mixture is agitated for a period of time at room temperature. In some embodiments, the period of time is between about 5 mins and about 1 hr. In some embodiments, the period of time is about 15 mins. In some embodiments, the reaction mixture is then heated to an elevated temperature and agitated. In some embodiments, the elevated temperature is between about 25° C. to about 70° C. In some embodiments, the elevated temperature is between about 40° C. to about 45° C. In some embodiments, the period of time is between about 1 h about 24 h. In some embodiments, the period of time is about 7 h. In some embodiments, the reaction mixture is then cooled to a lower temperature and agitated for a period of time. In some embodiments, the cooler temperature is room temperature. In some embodiments, the cooler temperature is between about 20° C. and about 25° C. In some embodiments, the period of time is between about 1 h about 24 h. In some embodiments, the period of time is about 10 h.

In some embodiments, the present invention provides a method for preparing compound I:

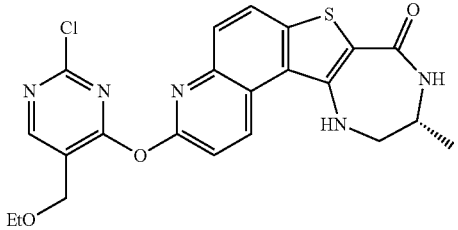

or a pharmaceutically acceptable salt thereof;
comprising the step of reacting a compound of formula 1-11:

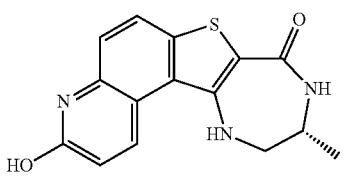

or a salt thereof,
with a compound of formula 1-12,

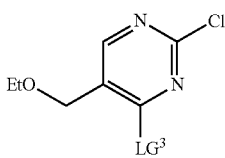

wherein:
LG³ is a suitable leaving group;
under suitable conditions to afford compound I, or a pharmaceutically acceptable salt thereof.

In some embodiments, compound I', or a pharmaceutically acceptable salt thereof, is prepared according to Scheme 3 set forth below:

Scheme 3

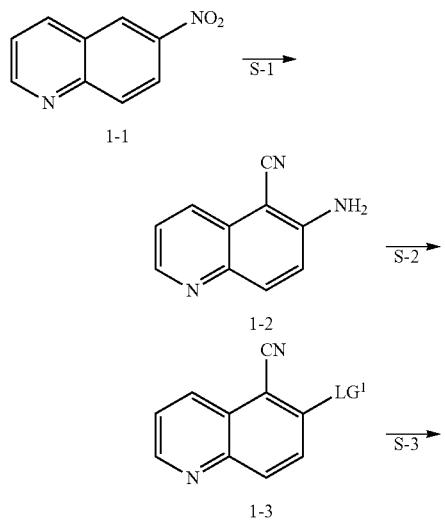

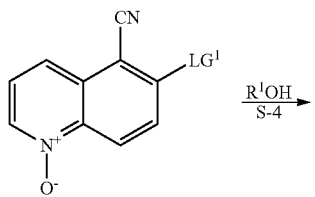

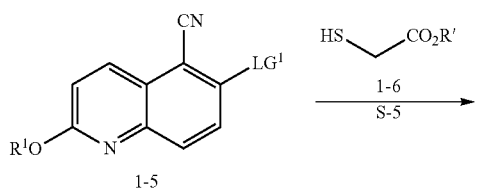

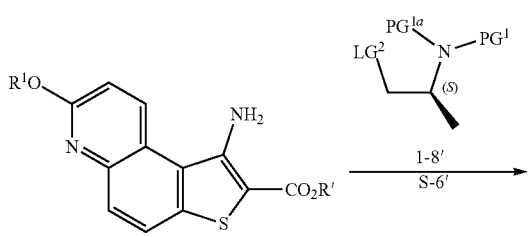

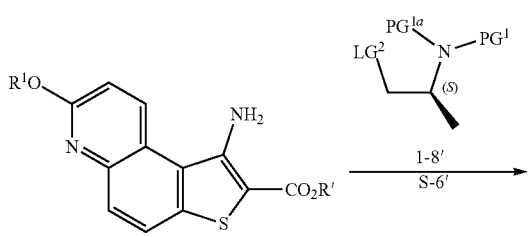

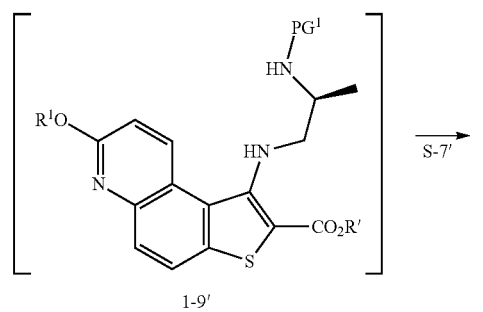

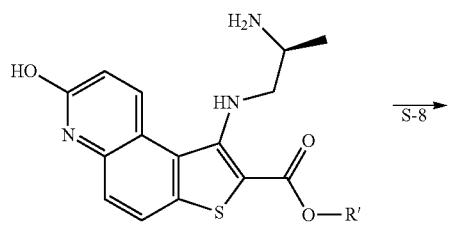

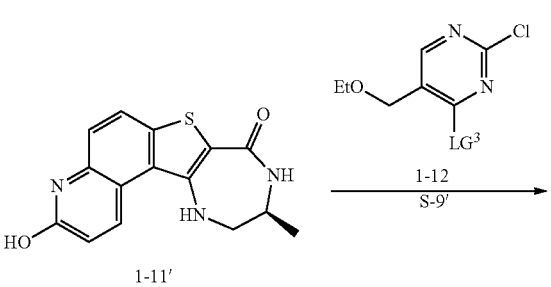

-continued

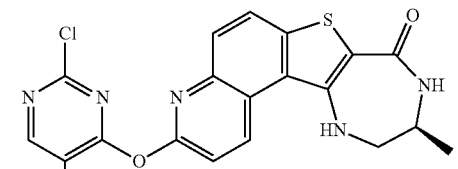

Compound I' wherein each of R¹, R', PG¹, LG¹, LG², and LG³ is as defined below and in classes and subclasses as described herein.

It will be appreciated that step S-6' is analogous to step S-6 discussed above, using a compound of formula 1-8' in place of a compound of formula 1-8. It will be appreciated that step S-7' is analogous to step S-7 discussed above, using a compound of formula 1-9' in place of a compound of formula 1-9. It will be appreciated that step S-8' is analogous to step S-8 discussed above, using a compound of formula 1-10' in place of a compound of formula 1-10. It will be appreciated that step S-9' is analogous to step S-9 discussed above, using a compound of formula 1-11' in place of a compound of formula 1-11.

In some embodiments, compound I', or a pharmaceutically acceptable salt thereof, is prepared according to Scheme 3-a set forth below:

Scheme 3-a

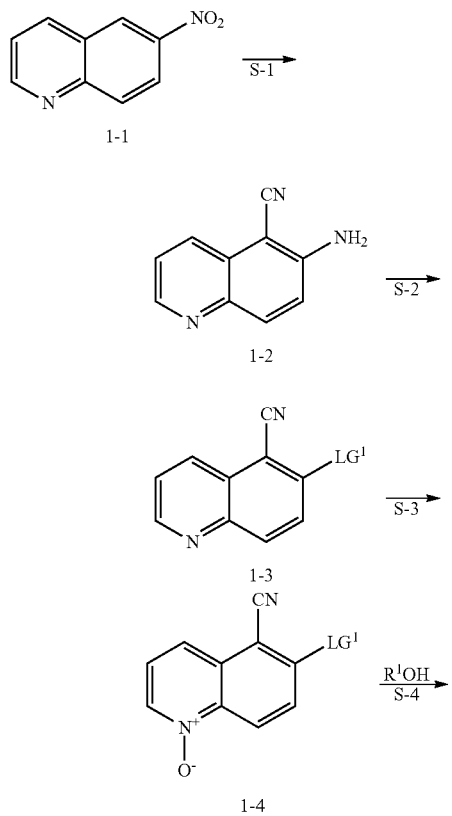

-continued

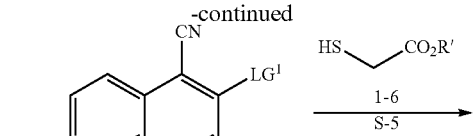

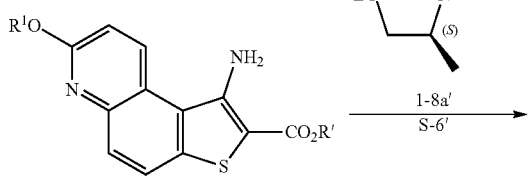

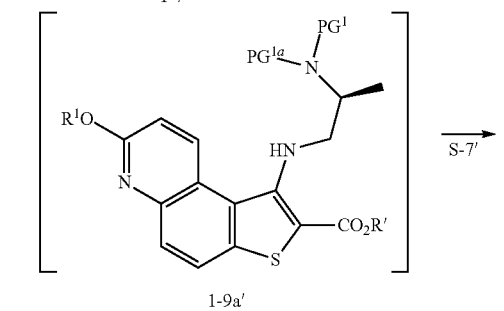

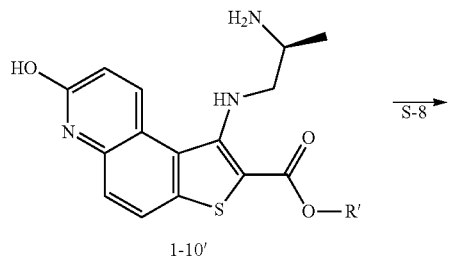

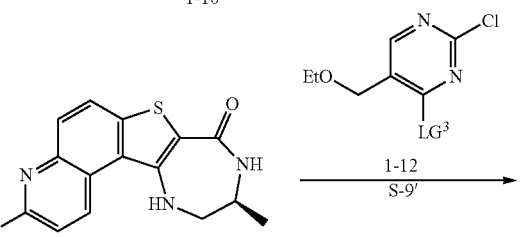

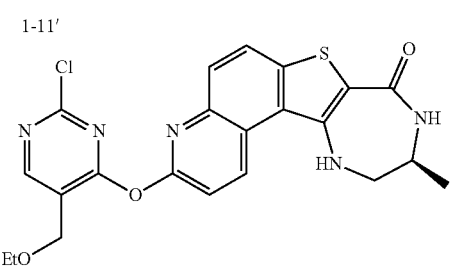

Compound I' wherein each of R¹, R', PG¹, PG¹ᵃ, LG¹, LG², and LG³ is as defined below and in classes and subclasses as described herein.

It will be appreciated that step S-6' is analogous to step S-6 in Scheme 2-a discussed above, using a compound of formula 1-8a' in place of a compound of formula 1-8a. It will be appreciated that step S-7' is analogous to step S-7 in Scheme 2-a discussed above, using a compound of formula 1-9a' in place of a compound of formula 1-9a. It will be appreciated that step S-8' is analogous to step S-8 discussed above, using a compound of formula 1-10' in place of a compound of formula 1-10. It will be appreciated that step S-9' is analogous to step S-9 discussed above, using a compound of formula 1-11' in place of a compound of formula 1-11.

Alternative Routes

In some embodiments, the present invention provides alternative methods for preparing a compound of formula 1-11 or a compound of formula 1-11'. In the alternative routes described herein, the position alpha to the quinoline nitrogen will be depicted as X, wherein X is selected from —OH, a suitably protected hydroxyl group —OPG², or a hydroxyl group surrogate which can be unveiled to reveal the hydroxyl or hydrogen, wherein the hydrogen can be converted to hydroxyl using a five-step protection/oxidation/rearrangement/deprotection/hydrolysis sequence to install a hydroxyl group as detailed in Scheme 1. These more general intermediates are referred to herein as "Compound X," "Compound X'," and "Compound X"."

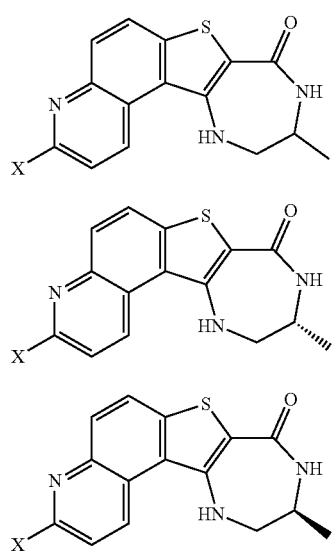

Compound X

Compound X'

Compound X"

In some embodiments, the present invention provides alternative methods for preparing Compound X, as depicted in Scheme 4.

Scheme 4.

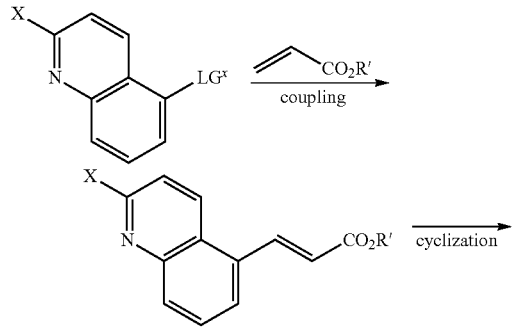

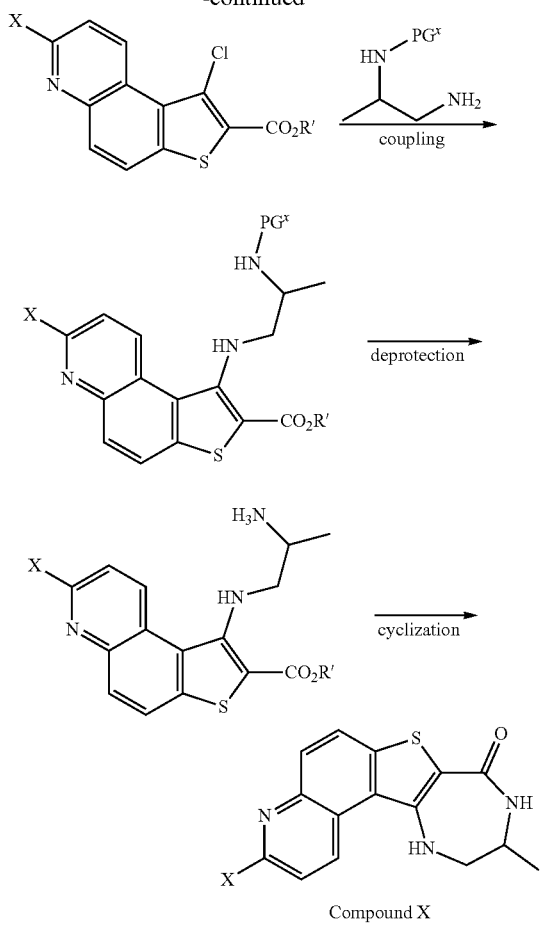

wherein
each R' is as defined above and described herein;
each LG$^x$ is a suitable leaving group as defined above and herein for LG$^1$, LG$^2$, LG$^3$; and
each PG$^x$ is a suitable nitrogen protecting group as defined above and herein for PG$^1$.

Examples of a methods described by Scheme 4 are provided in Scheme 4-a and Scheme 4-b.

Scheme 4-a.

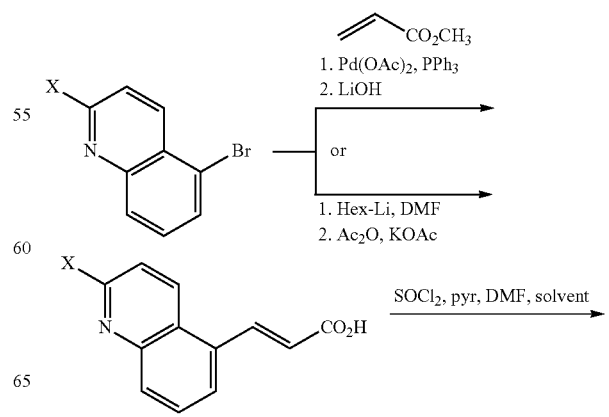

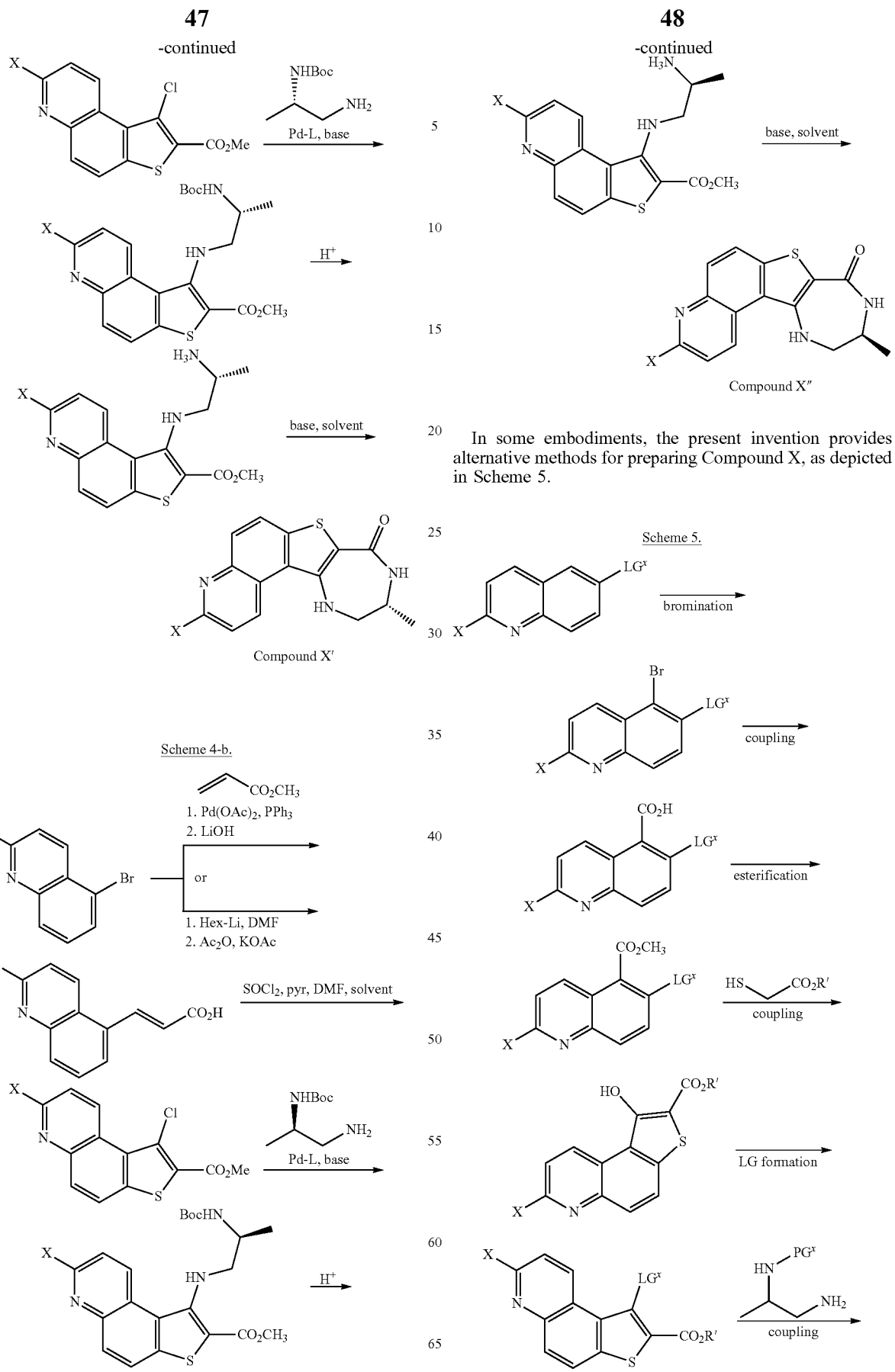
In some embodiments, the present invention provides alternative methods for preparing Compound X, as depicted in Scheme 5.

-continued
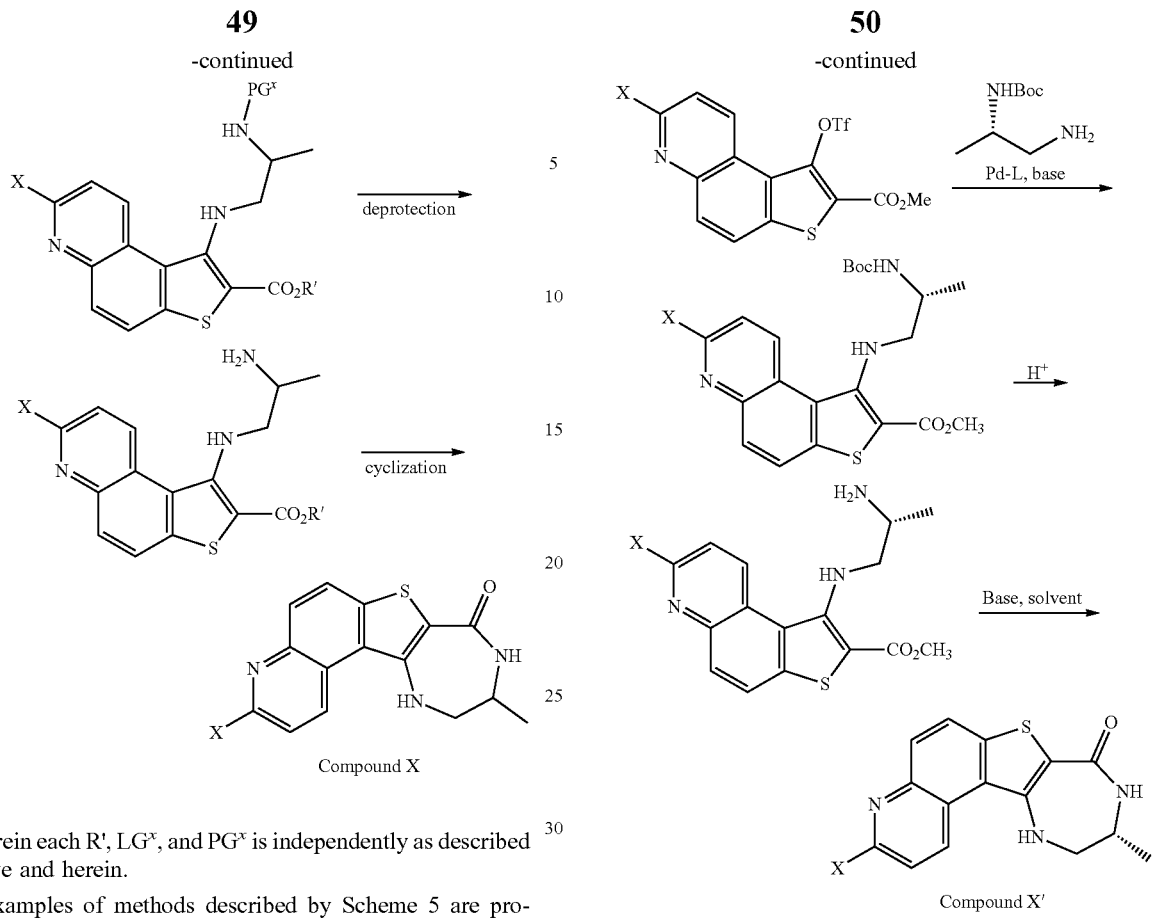
wherein each R', LG$^x$, and PG$^x$ is independently as described above and herein.
Examples of methods described by Scheme 5 are provided in Scheme 5-a and Scheme 5-b.
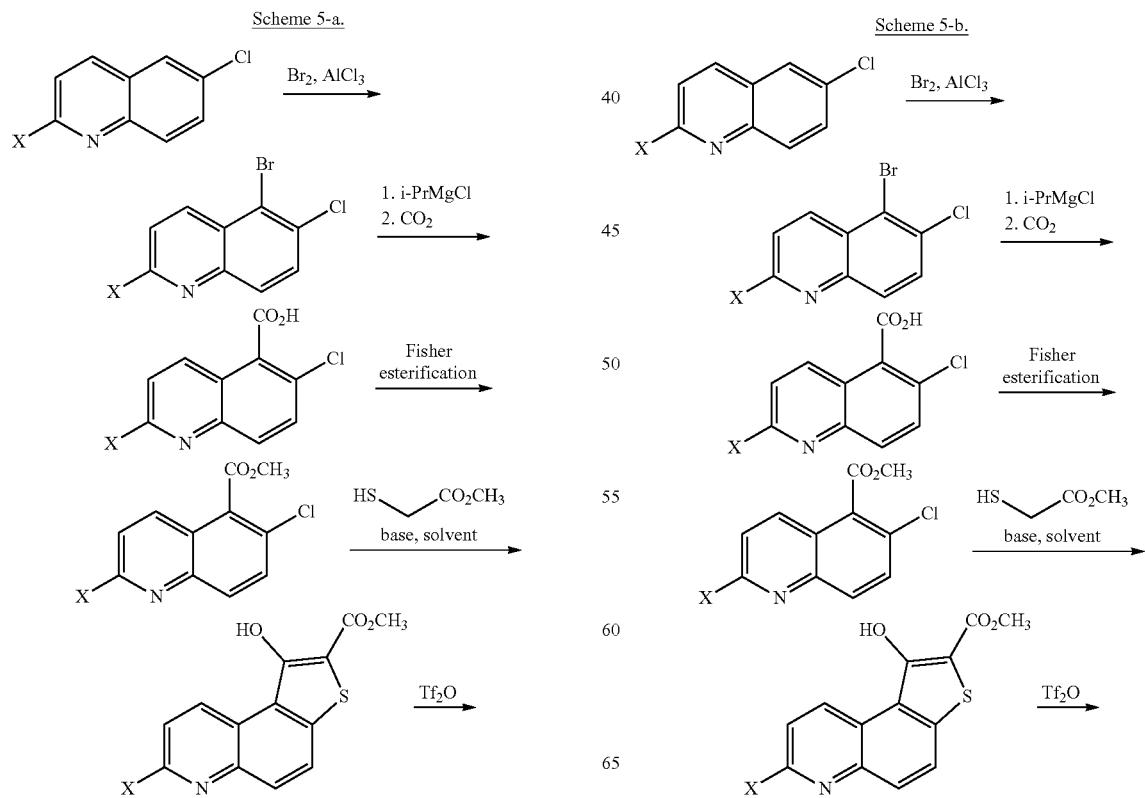

51

-continued

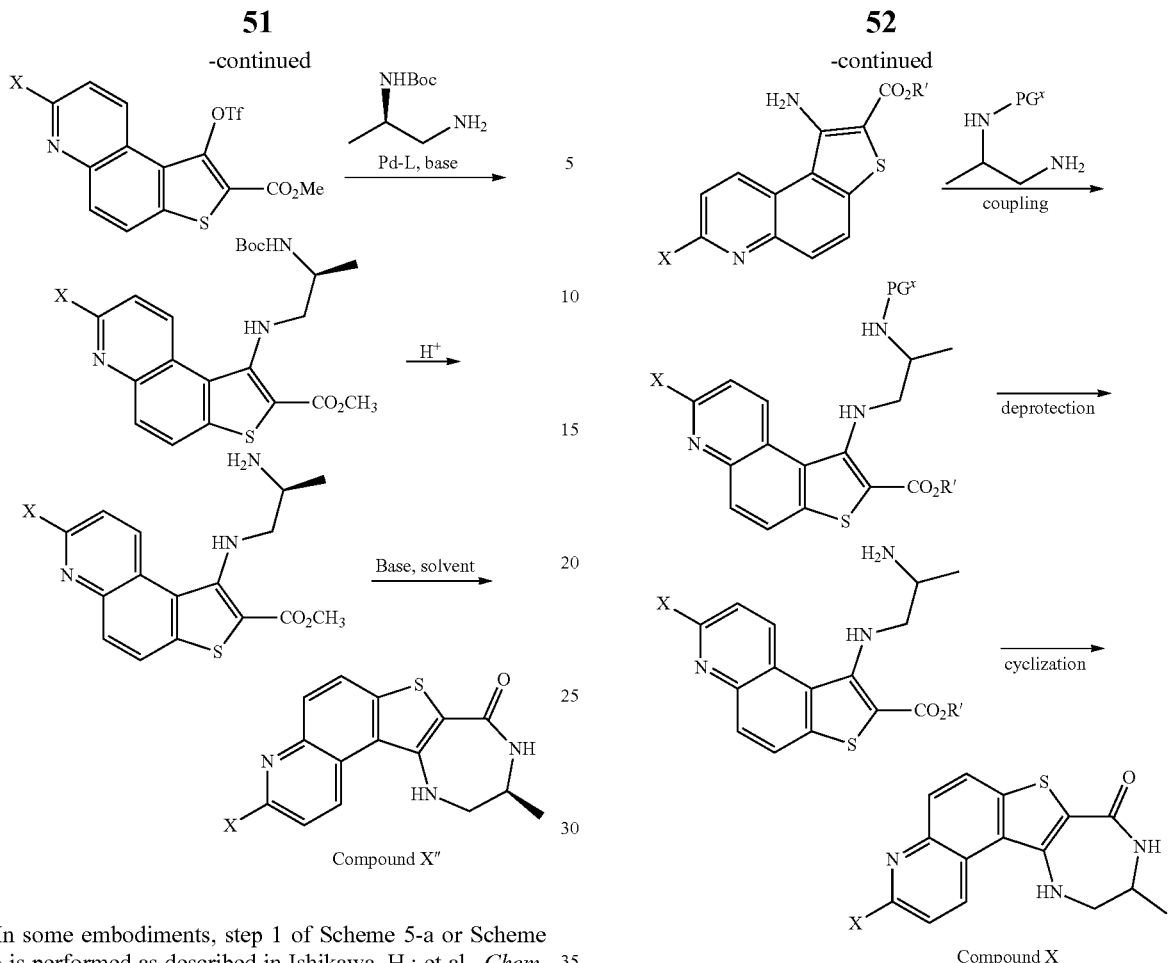

In some embodiments, step 1 of Scheme 5-a or Scheme 5-b is performed as described in Ishikawa, H.; et al., *Chem. Pharm. Bull.*, 37(8), 2103-2108 (1989). In some embodiments, step 2 of Scheme 5-a or Scheme 5-b is performed as described in WO 2009/132000 A1.

In some embodiments, the present invention provides alternative methods for preparing Compound X, as depicted in Scheme 6.

52

-continued wherein each R', $LG^x$, and $PG^x$ is independently as described above and here.

Examples of methods described by Scheme 6 are provided in Scheme 6-a and Scheme 6-b.

Scheme 6.

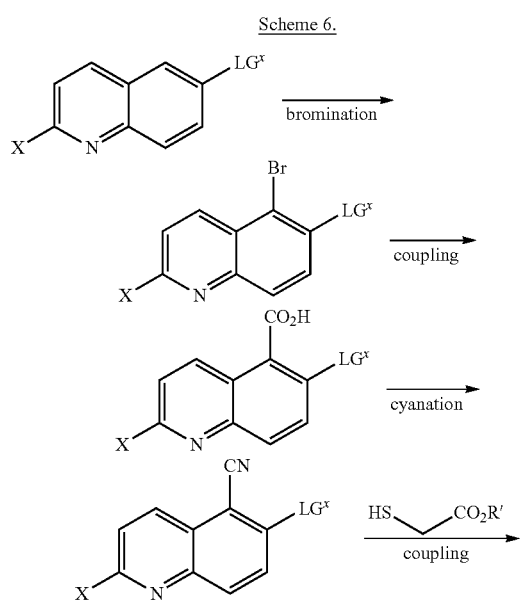

Scheme 6-a.

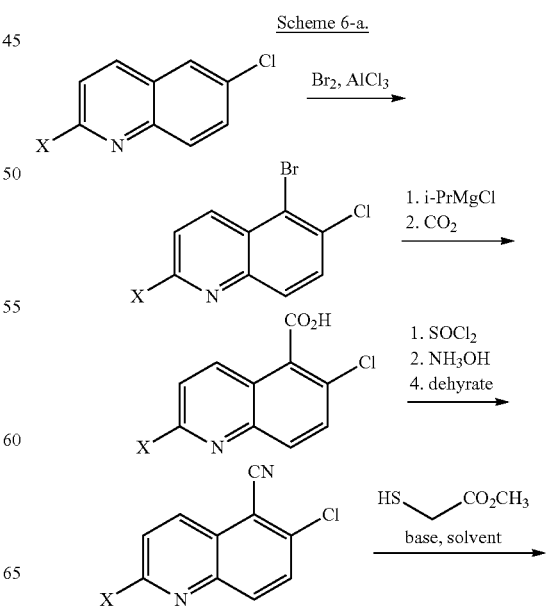

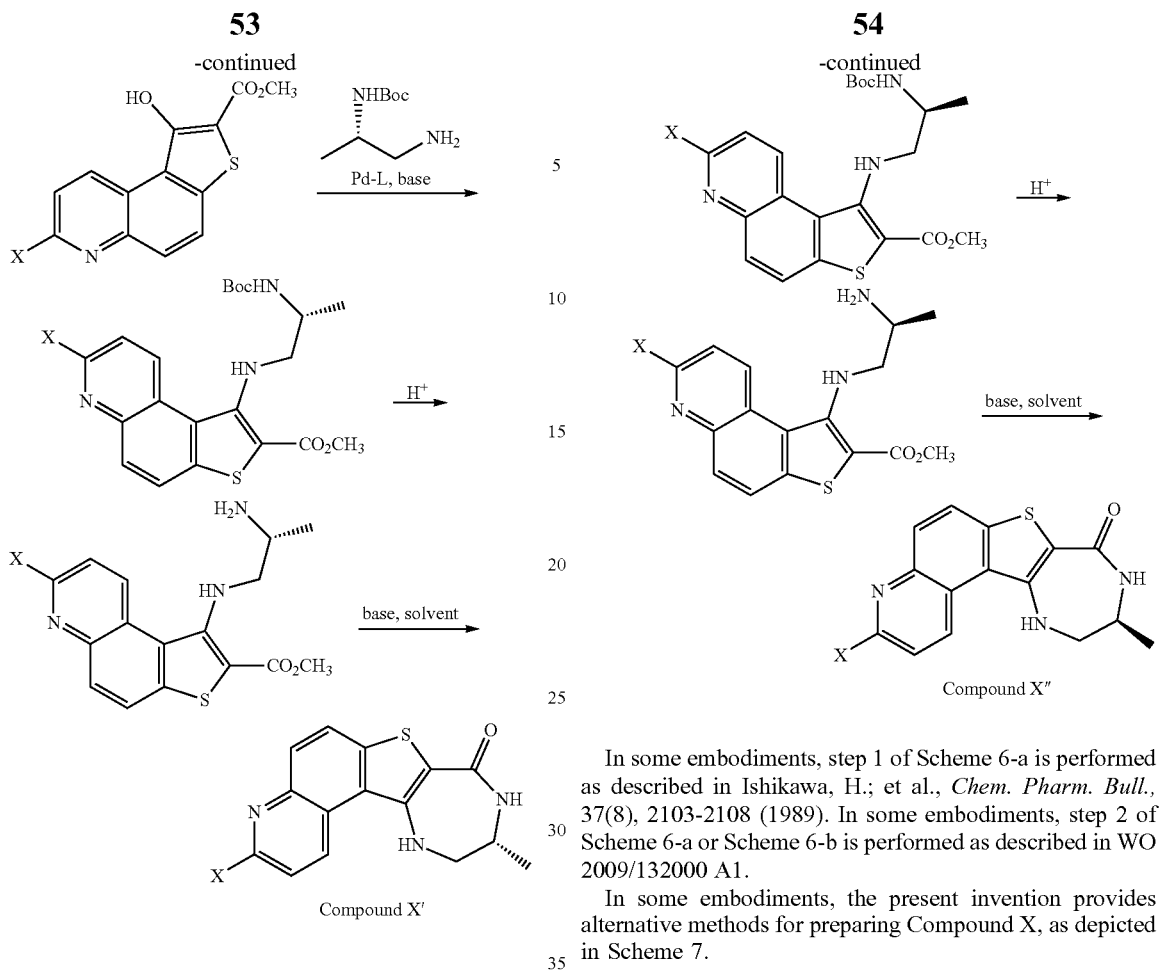
In some embodiments, step 1 of Scheme 6-a is performed as described in Ishikawa, H.; et al., *Chem. Pharm. Bull.*, 37(8), 2103-2108 (1989). In some embodiments, step 2 of Scheme 6-a or Scheme 6-b is performed as described in WO 2009/132000 A1.
In some embodiments, the present invention provides alternative methods for preparing Compound X, as depicted in Scheme 7.
Scheme 6-b.
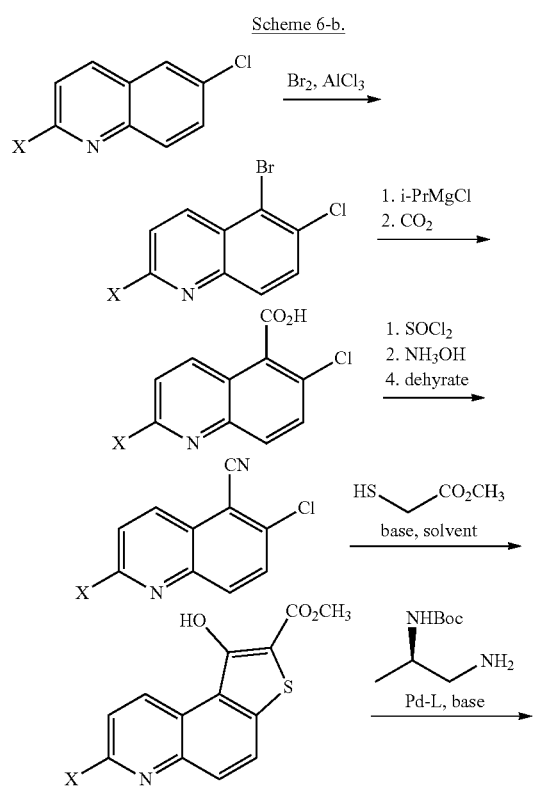
Scheme 7.
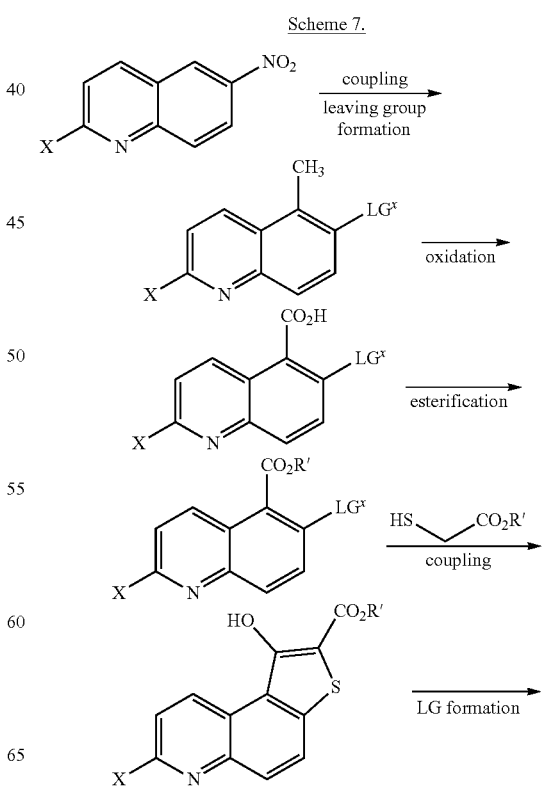

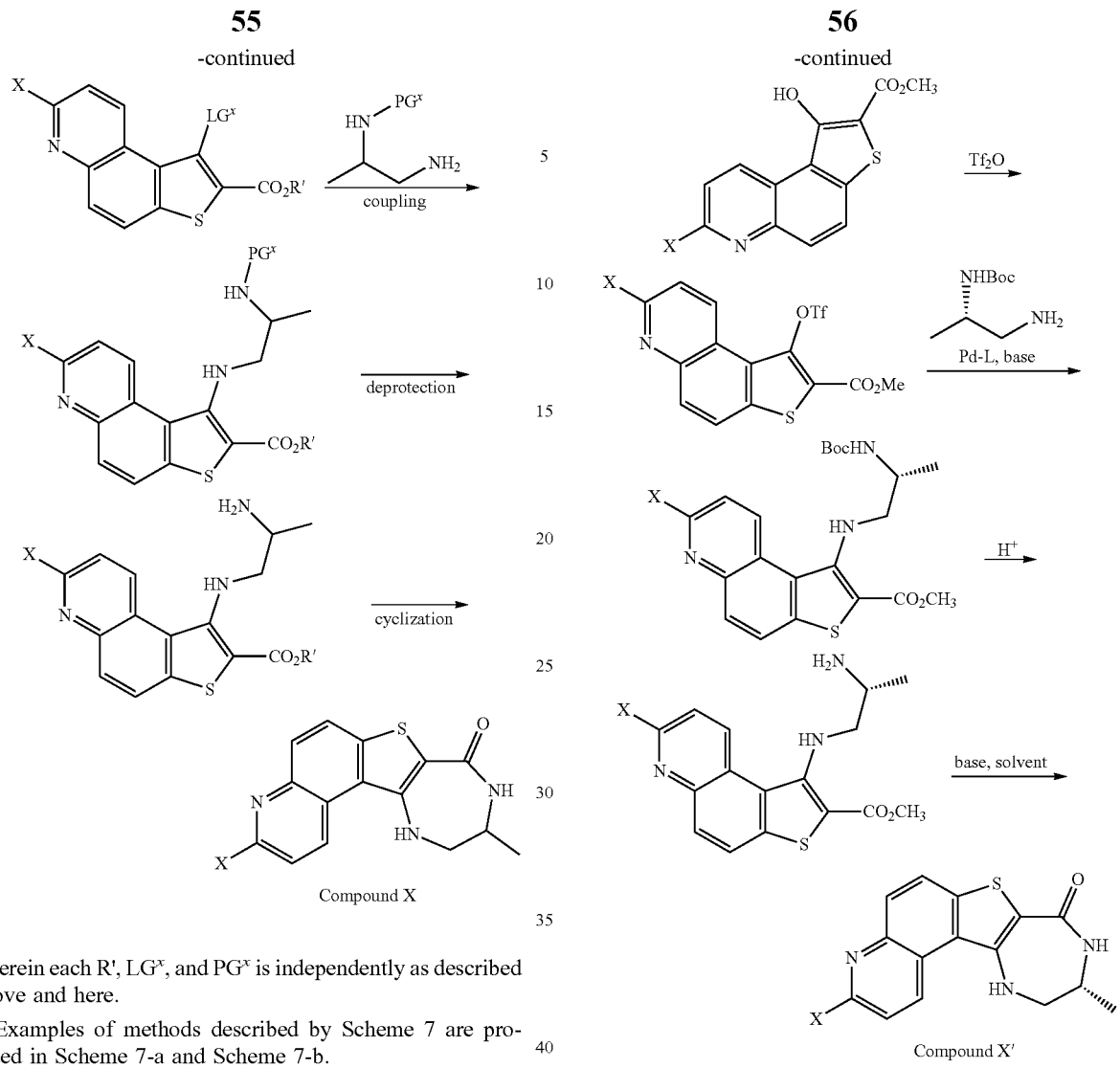
wherein each R', LG$^x$, and PG$^x$ is independently as described above and here.
Examples of methods described by Scheme 7 are provided in Scheme 7-a and Scheme 7-b.
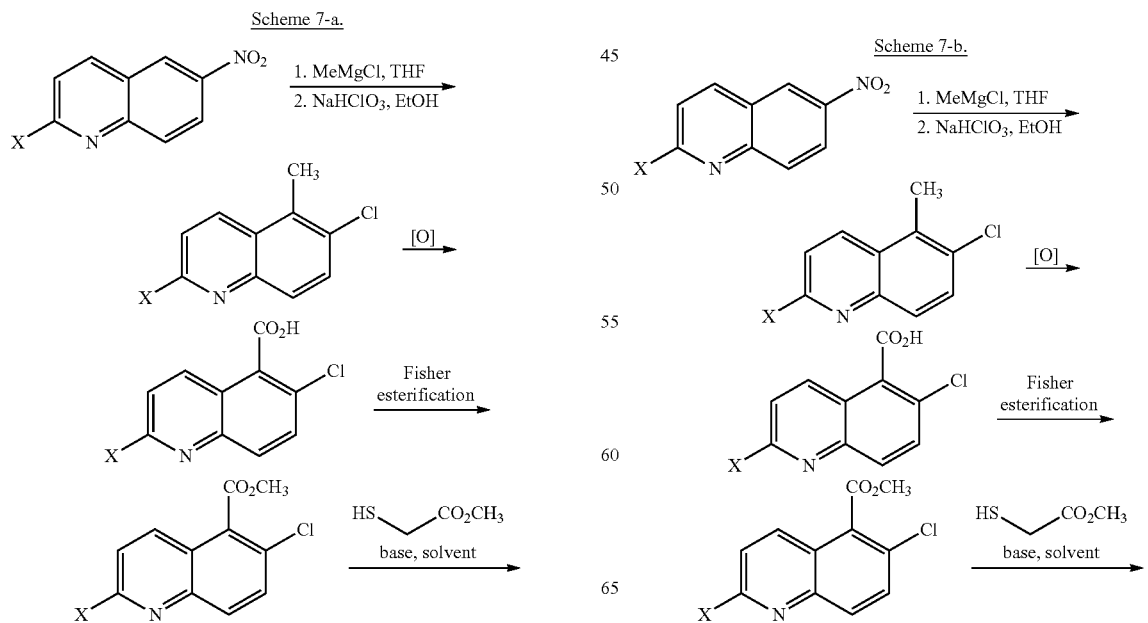

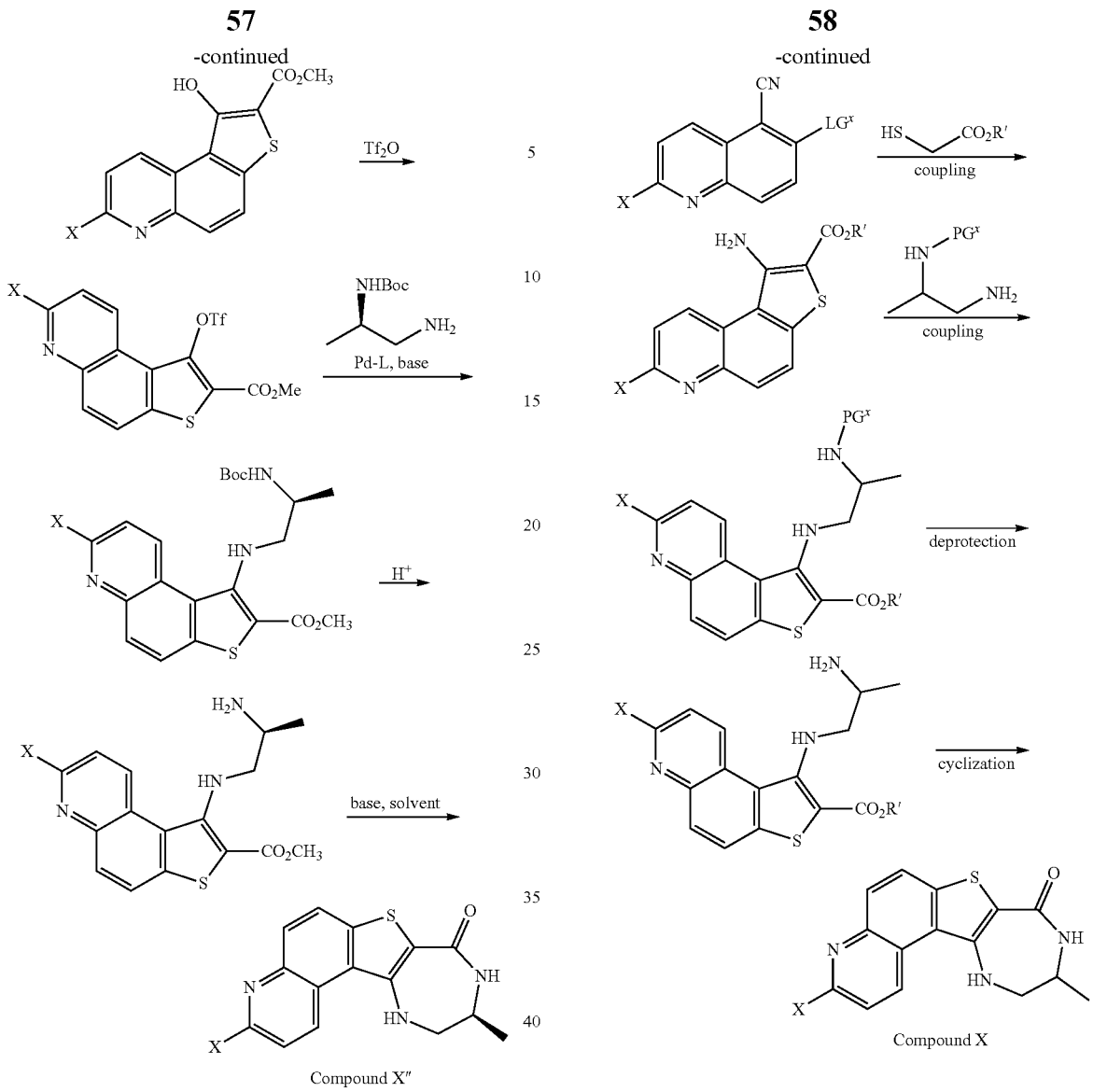
In some embodiments, the present invention provides alternative methods for preparing Compound X, as depicted in Scheme 8.
wherein each R', LG$^x$, and PG$^x$ is independently as described above and here.
Examples of methods described by Scheme 8 are provided in Scheme 8-a and Scheme 8-b.
Scheme 8.
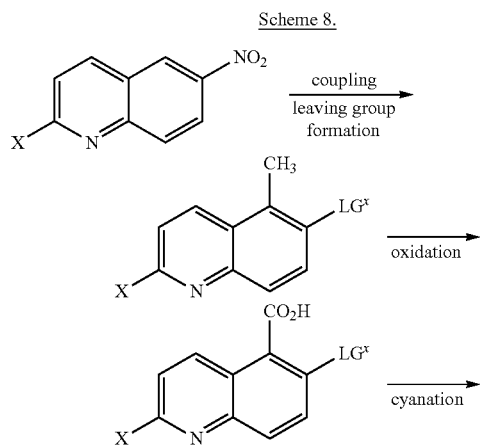
Scheme 8-a.
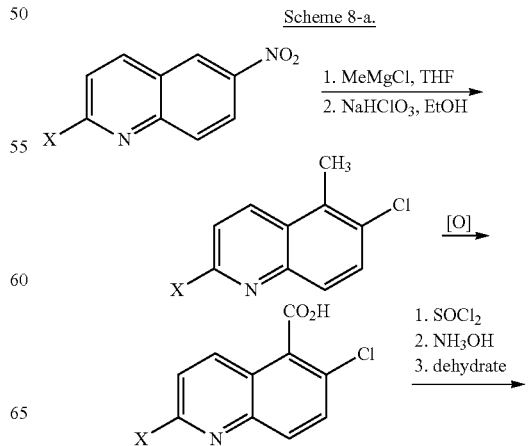

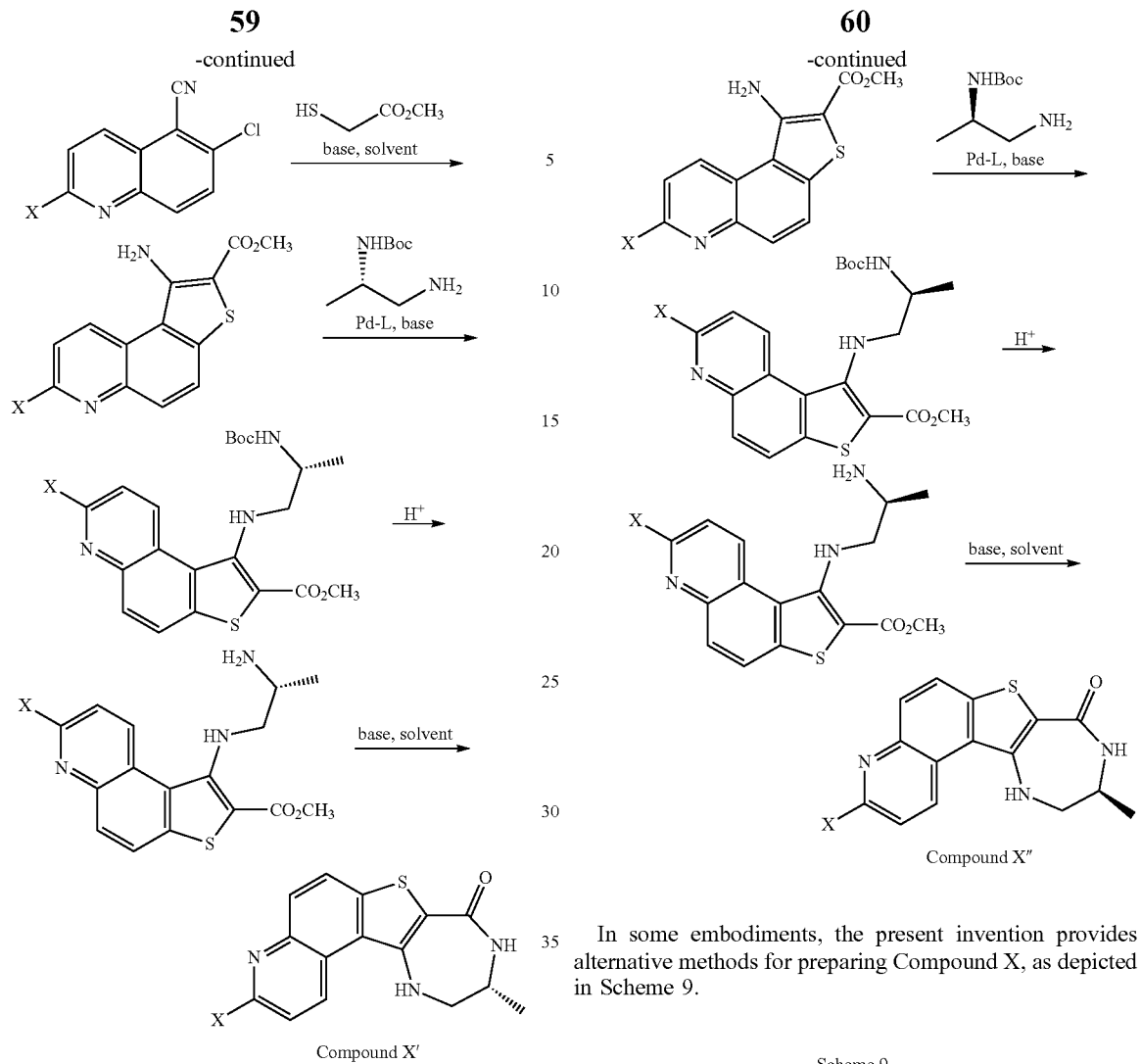
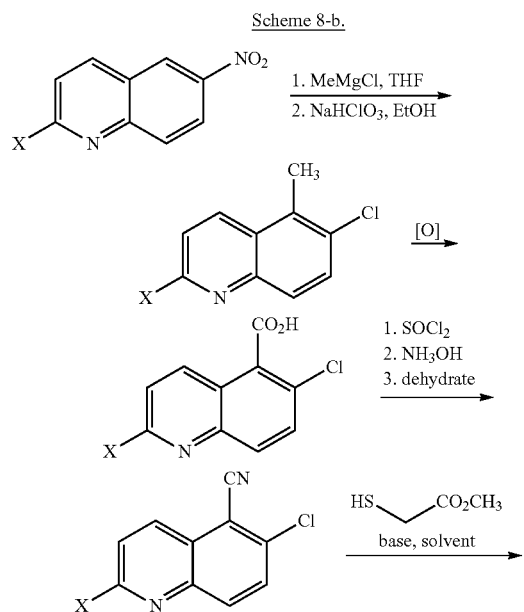
Scheme 8-b.
In some embodiments, the present invention provides alternative methods for preparing Compound X, as depicted in Scheme 9.
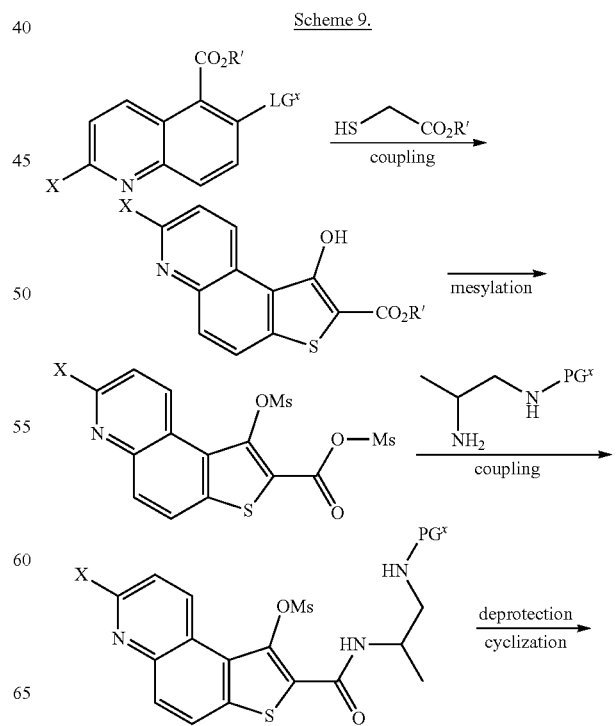
Scheme 9.

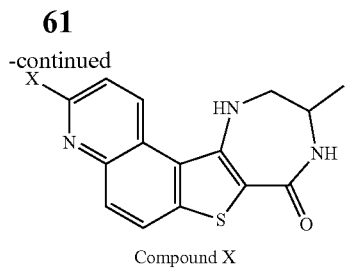

Compound X wherein each R', LG$^x$, and PG$^x$ is independently as described above and here.

Examples of methods described by Scheme 9 are provided in Scheme 9-a and Scheme 9-b.

Scheme 9-a.

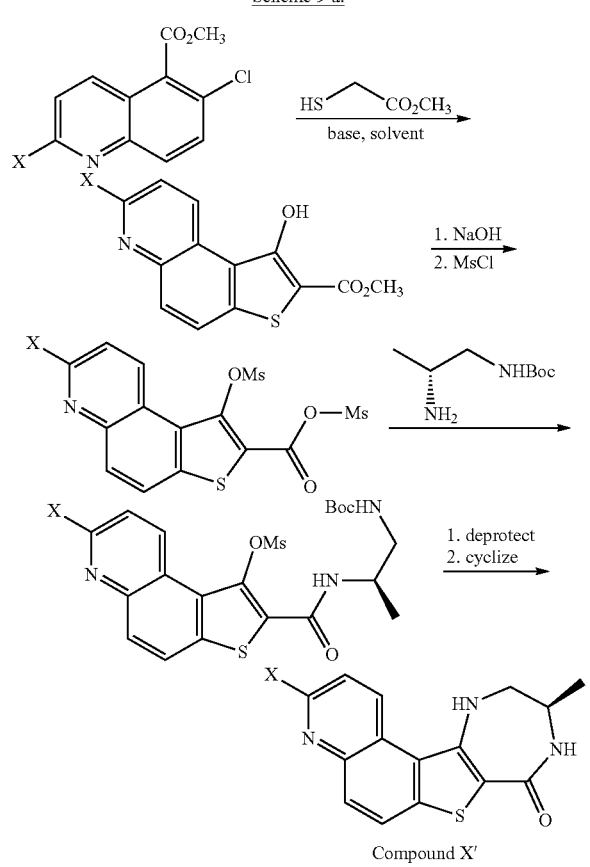

Compound X'

Scheme 9-b.

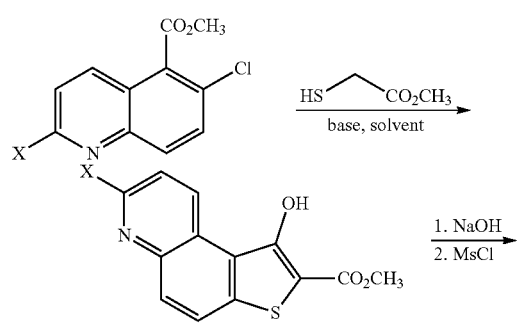

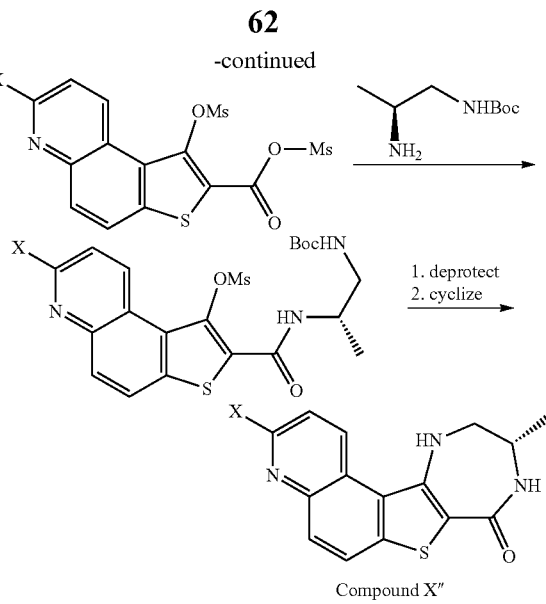

Compound X''

In some embodiments, the present invention provides alternative methods for preparing Compound X, as depicted in Scheme 10.

Scheme 10.

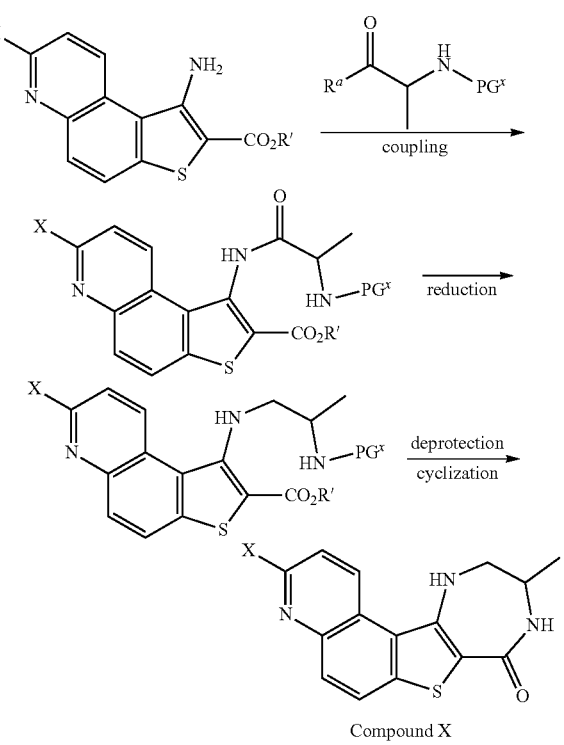

Compound X wherein each of LG$^x$, PG$^x$, and R' is independently as described above and herein; and R$^a$ is an activating moiety.

Suitable activating moieties (i.e., R$^a$ groups) are well known in the art and include those described in detail in *Protecting Groups in Organic Synthesis*, T. W. Green and P. G. M. Wuts, 3$^{rd}$ edition, John Wiley & Sons, 1999. In some embodiments, R$^a$ is —OR, wherein R is as defined above and described herein. In some embodiments, R$^a$ is a halogen.

63

In some such embodiments, $R^a$ is chloride. In some embodiments, $R^a$ is —OC(O)R, wherein R is as defined above and described herein.

Examples of methods described by Scheme 10 are provided in Scheme 10-a and Scheme 10-b.

Scheme 10-a.

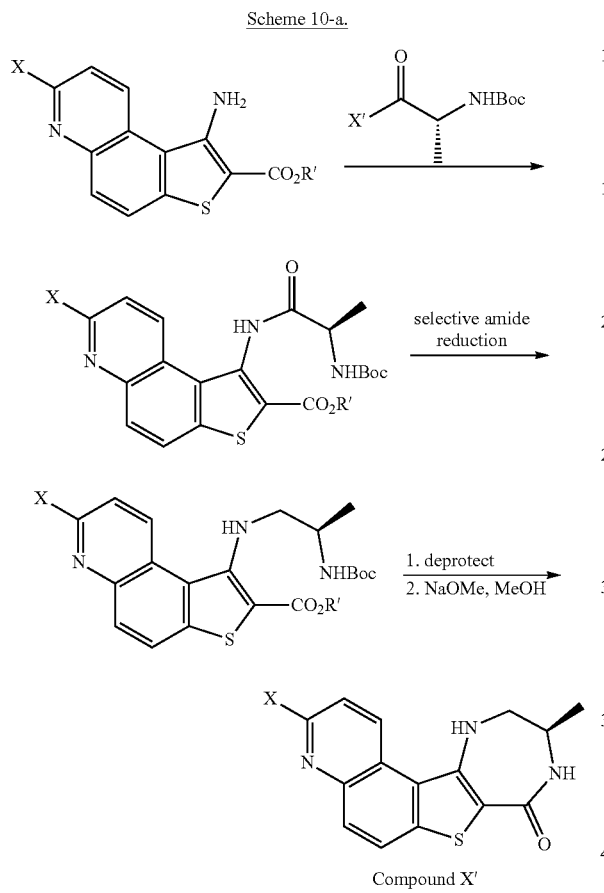

Scheme 10-b.

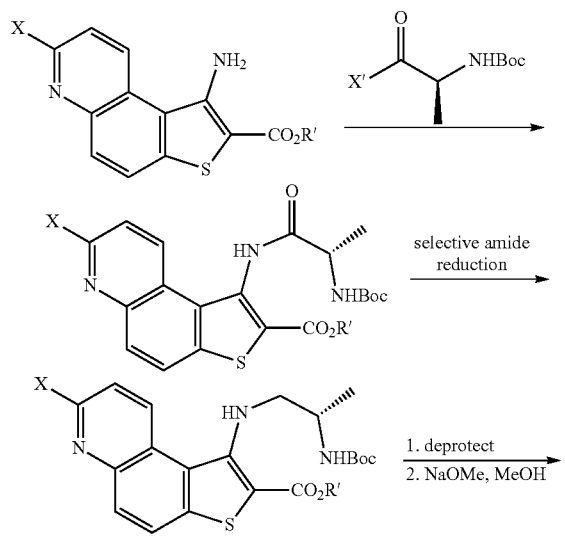

64

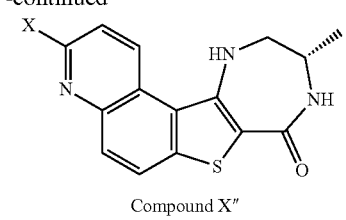

Compound X″ wherein each R' is independently as described above and herein; and X' is a halogen.

In some embodiments, X' is chloro. In some embodiments, X' is bromo. In some embodiments, X' is iodo.

In some embodiments, the present invention provides alternative methods for preparing Compound X, as depicted in Scheme 11.

Scheme 11.

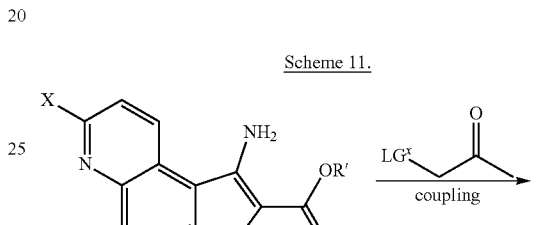

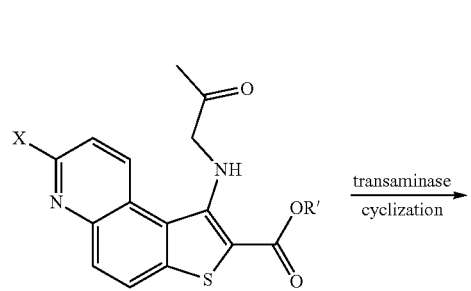

Compound X wherein each $LG^x$ and R' is independently as described above and herein.

Examples of methods described by Scheme 11 are provided in Scheme 11-a and Scheme 11-b.

Scheme 11-a.

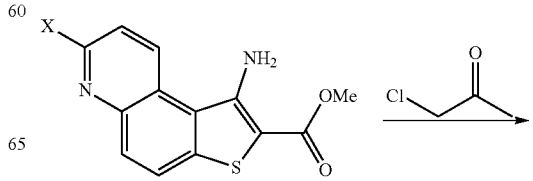

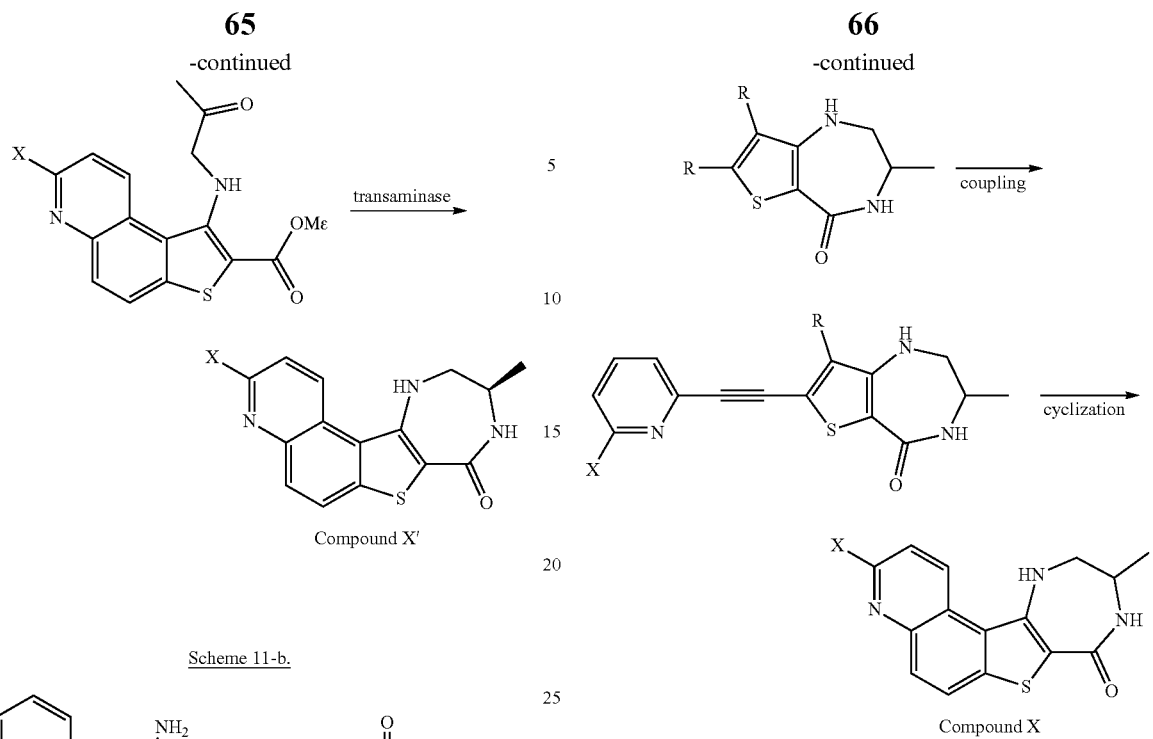
Scheme 11-b.
In some embodiments, the present invention provides alternative methods for preparing Compound X, as depicted in Scheme 12.
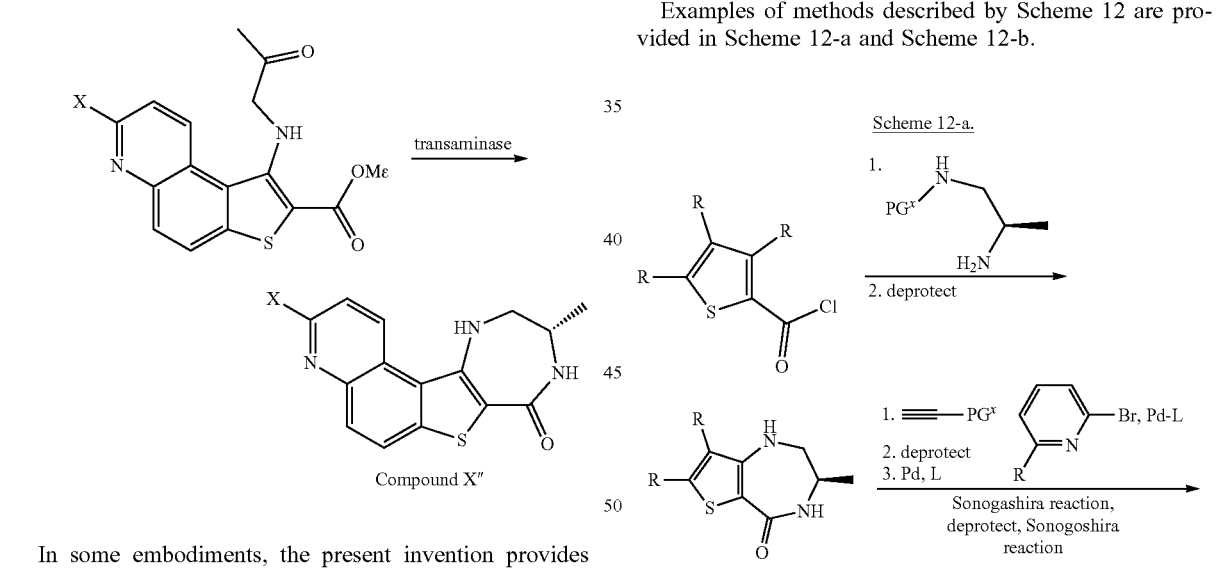
wherein each PG$^x$ and R is independently as described above and herein
Examples of methods described by Scheme 12 are provided in Scheme 12-a and Scheme 12-b.
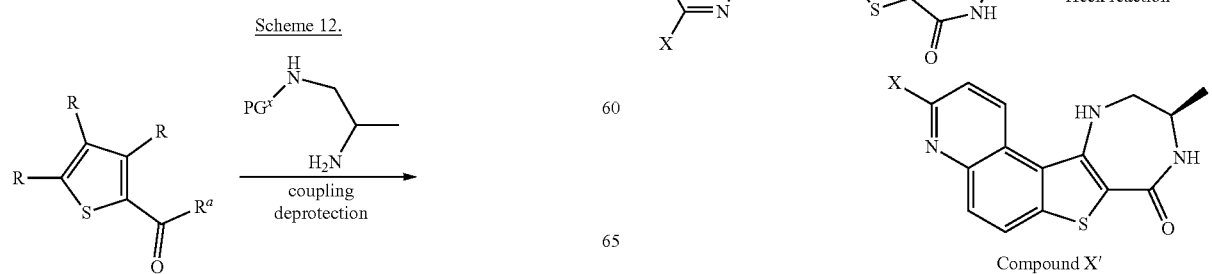

Scheme 12-b.
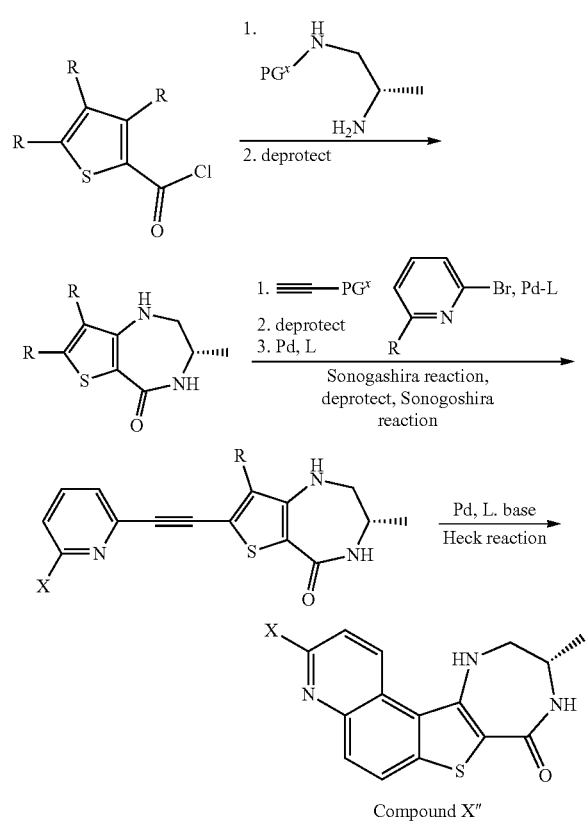
In some embodiments, the present invention provides alternative methods for preparing Compound X, as depicted in Scheme 13.
wherein each R', LG$^x$, and PG$^x$ is independently as described above and here.
Examples of methods described by Scheme 13 are provided in Scheme 13-a and Scheme 13-b.
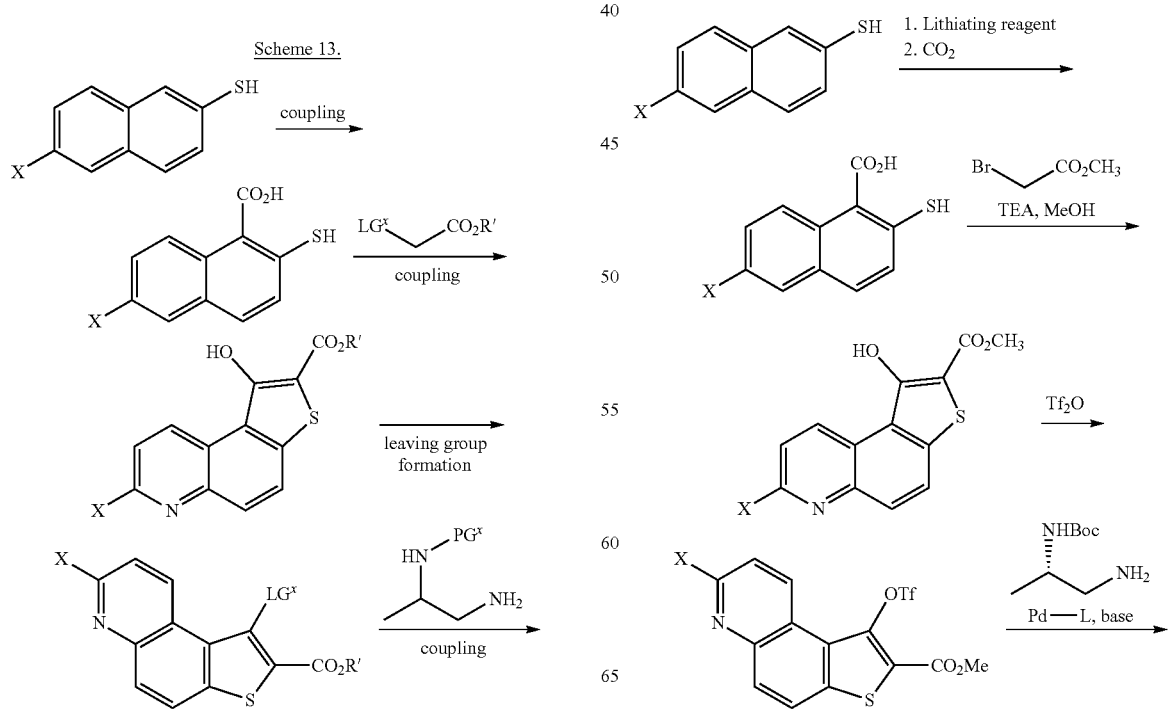

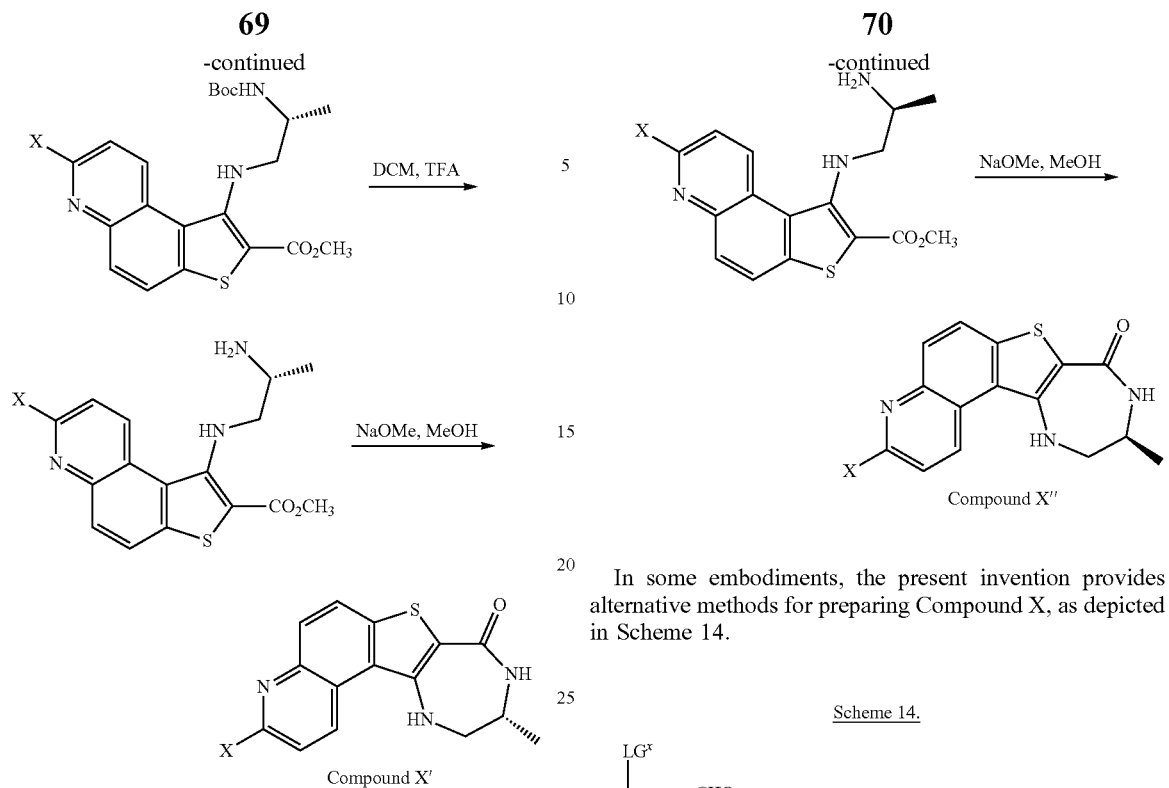
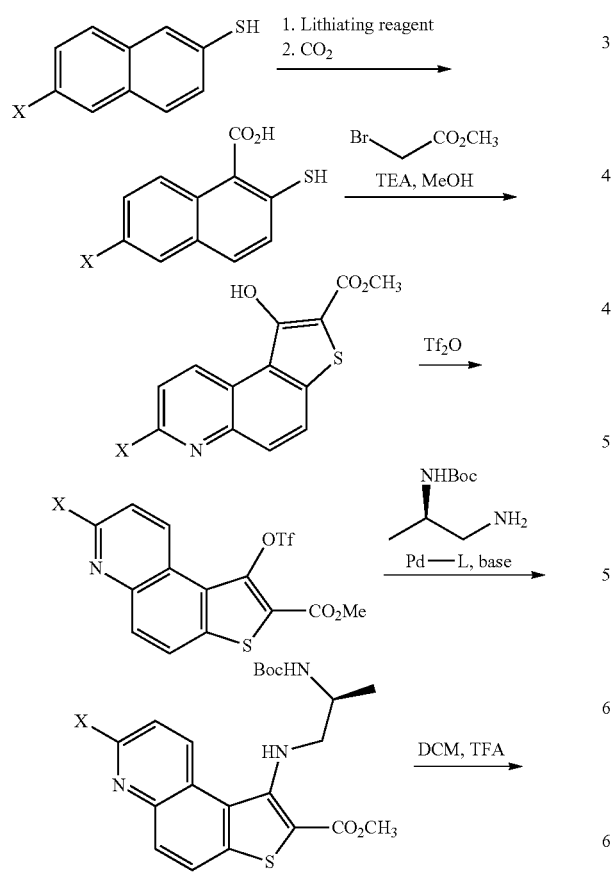
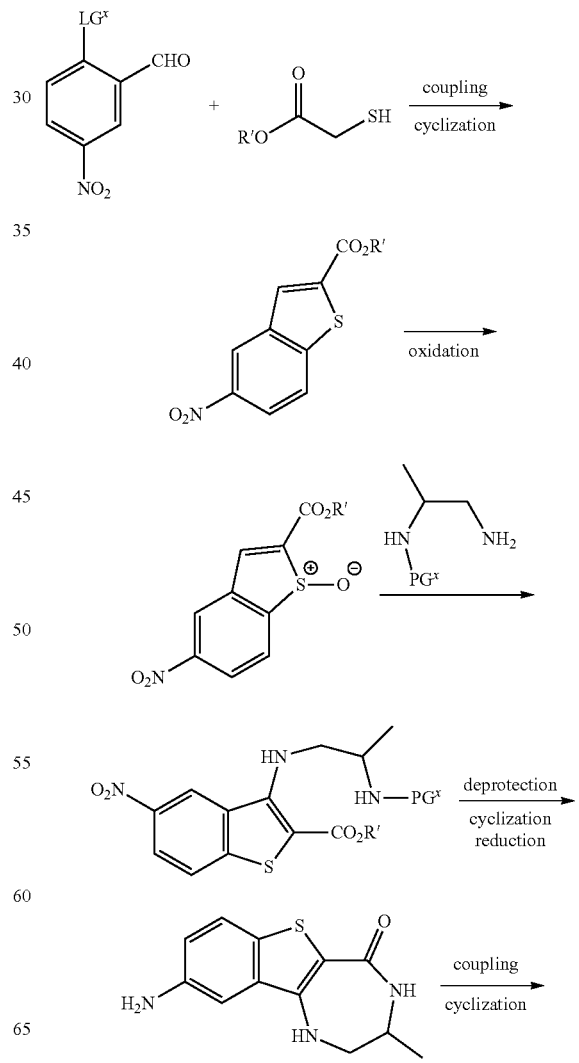
In some embodiments, the present invention provides alternative methods for preparing Compound X, as depicted in Scheme 14.

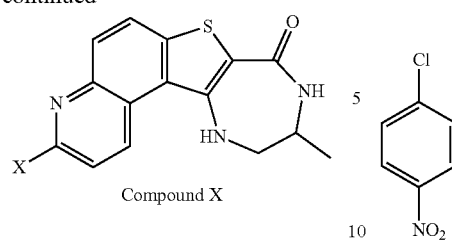
Compound X
wherein each LG$^x$, PG$^x$, and R' is independently as described above and herein.
Examples of methods described by Scheme 14 are provided in Scheme 14-a and Scheme 14-b.
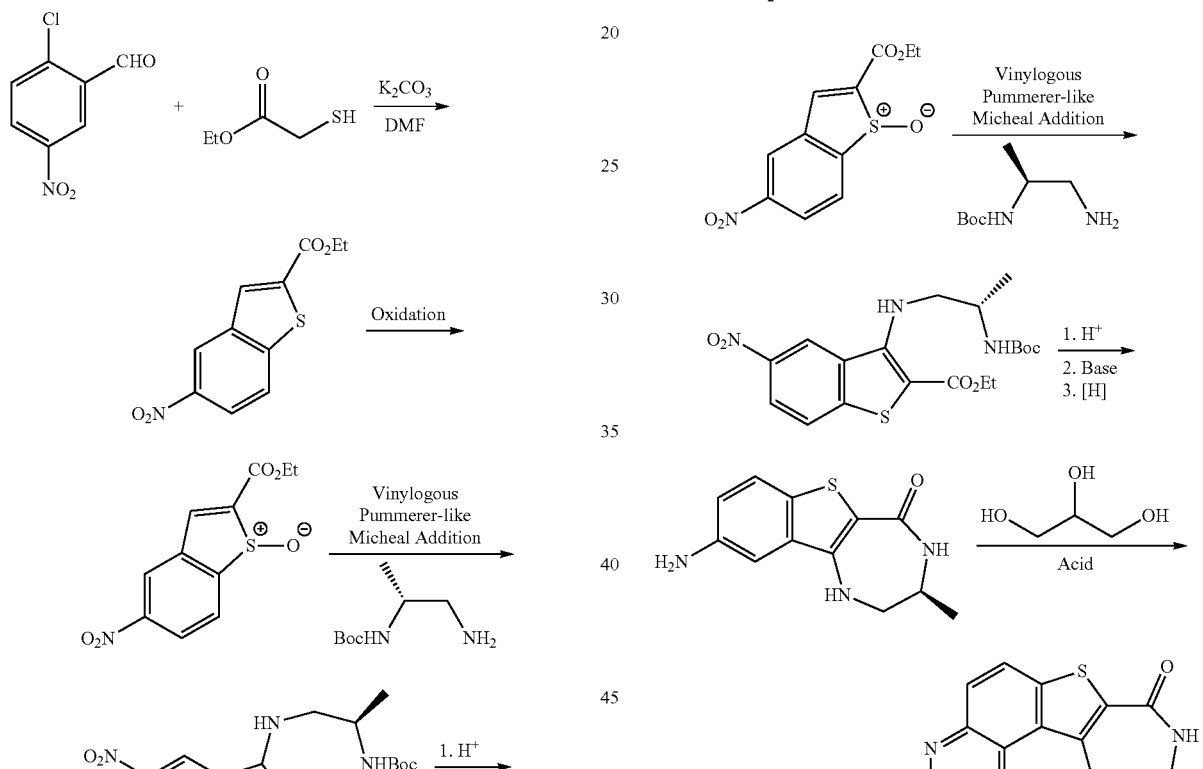
In some embodiments, the present invention provides alternative methods for preparing Compound X, as depicted in Scheme 15.
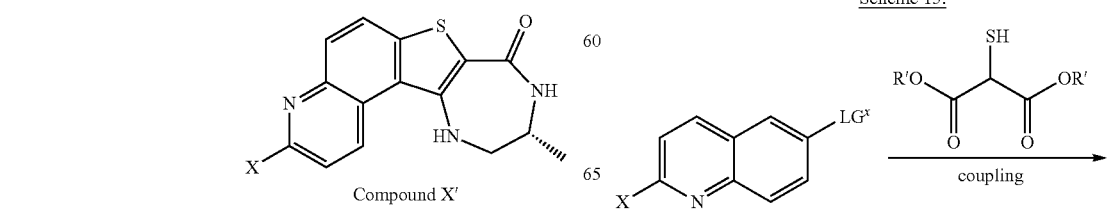

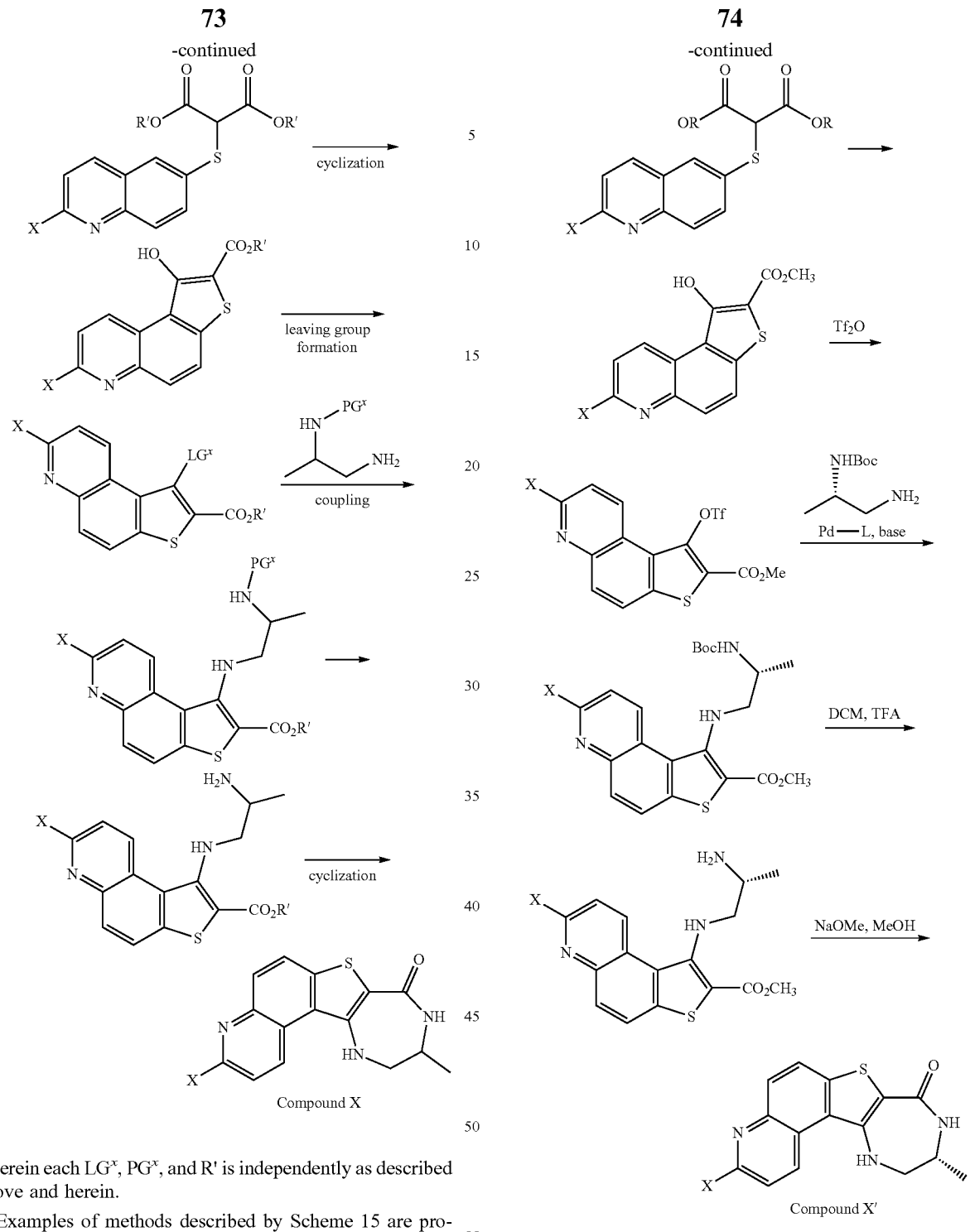
wherein each LG$^x$, PG$^x$, and R' is independently as described above and herein.
Examples of methods described by Scheme 15 are provided in Scheme 15-a and Scheme 15-b.
Scheme 15-a.
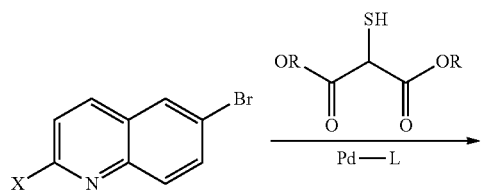
Scheme 15-b.
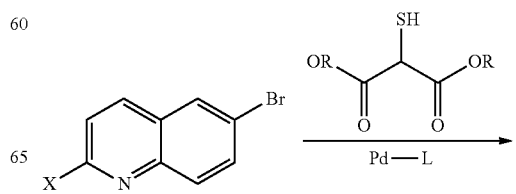

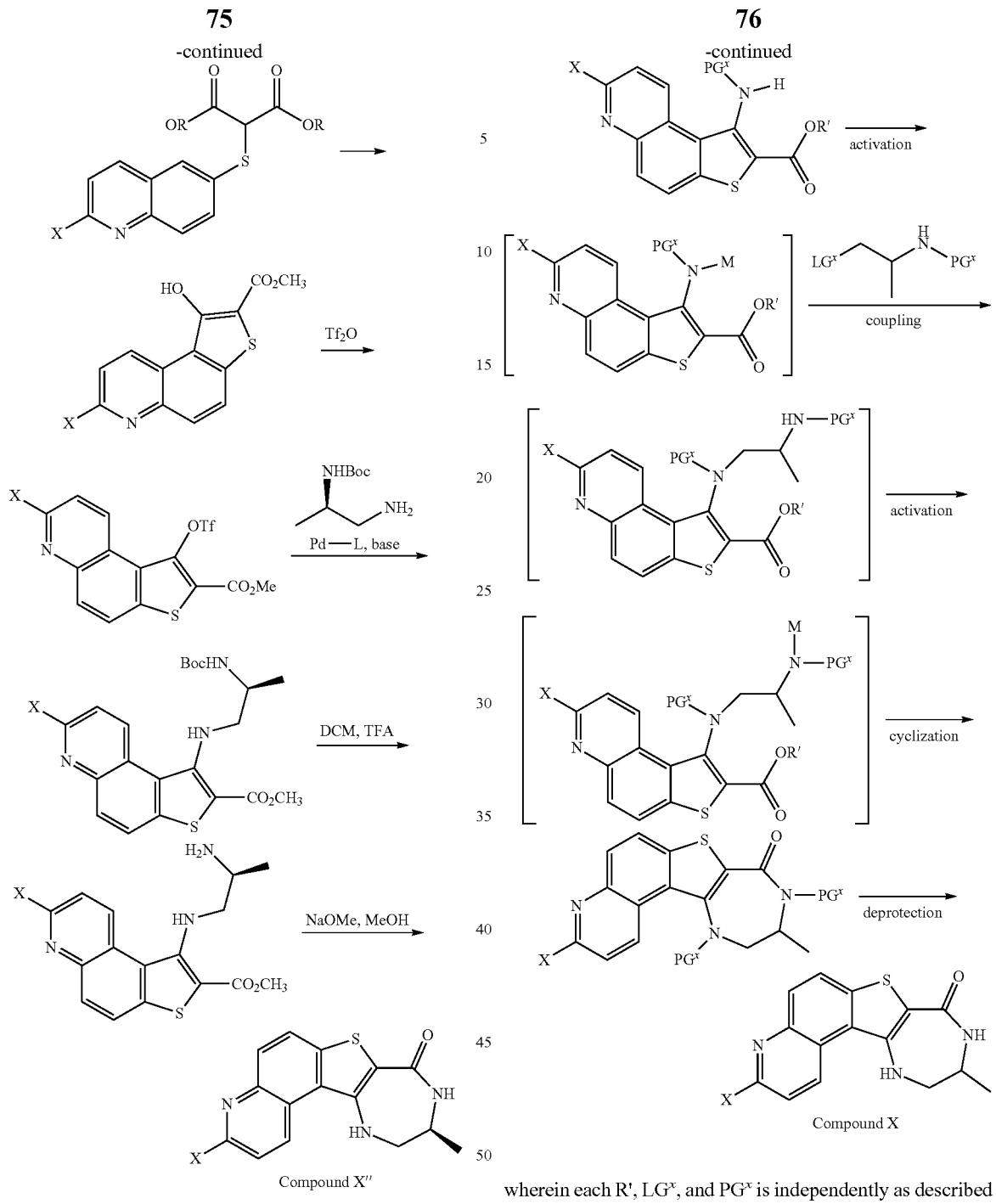
In some embodiments, the present invention provides alternative methods for preparing Compound X, as depicted in Scheme 16.
wherein each R', LG$^x$, and PG$^x$ is independently as described above and herein; and M represents a metal atom.
In some embodiments, M is lithium.
Examples of methods described by Scheme 16 are provided in Scheme 16-a and Scheme 16-b.
Scheme 16.
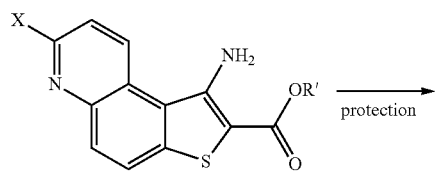
Scheme 16-a.
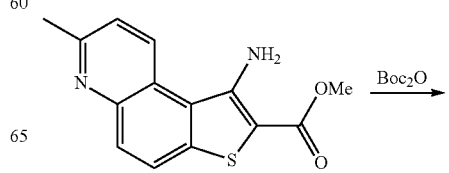

77
-continued
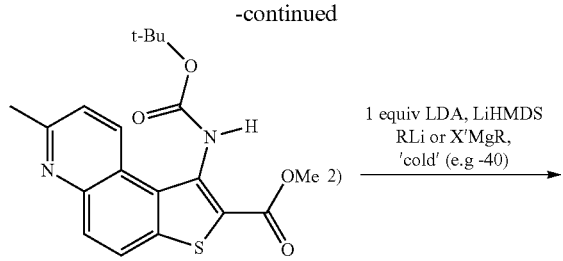
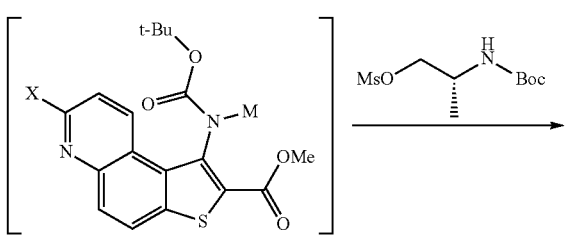
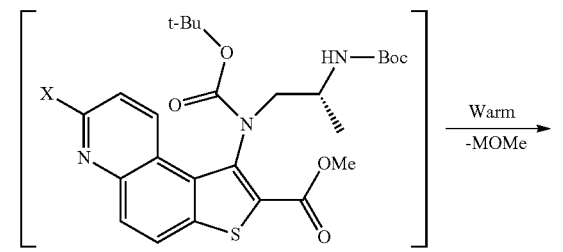
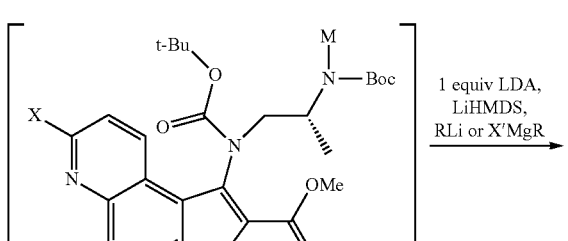
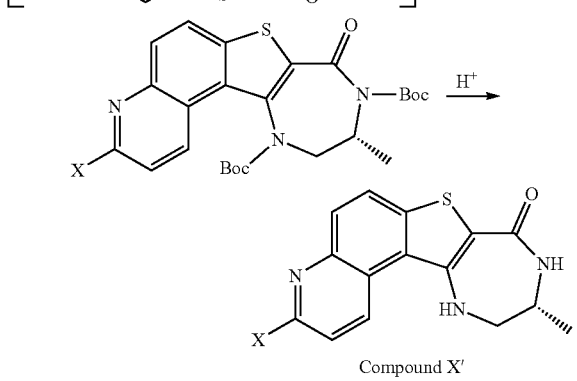
Compound X'
Scheme 16-b.
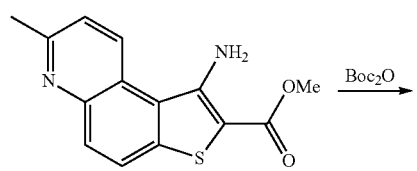
78
-continued
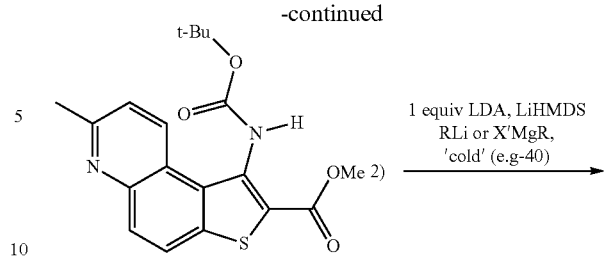
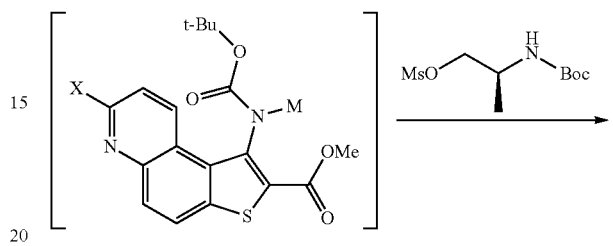
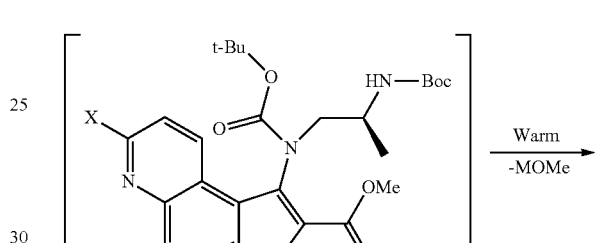
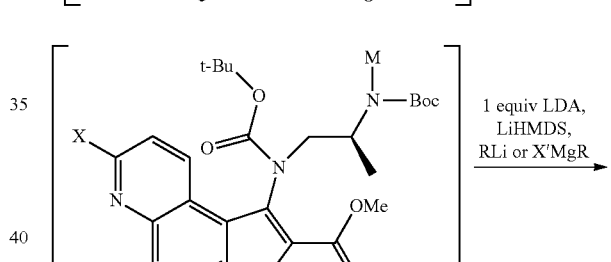
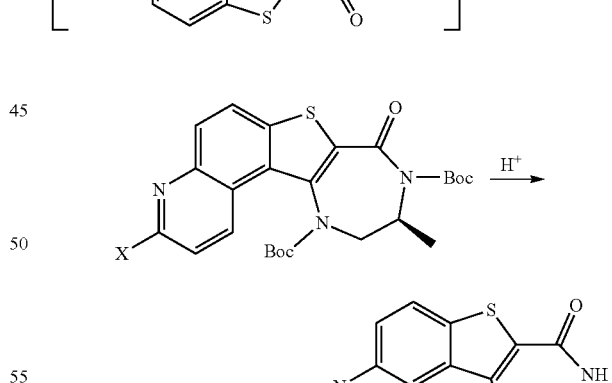
Compound X''
wherein each R is independently as described above and herein each X' is independently as defined above and described herein.
In some embodiments, the present invention provides alternative methods for preparing Compound X, as depicted in Scheme 17.

Scheme 17.
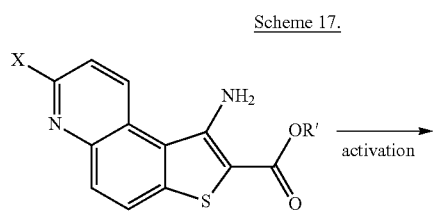
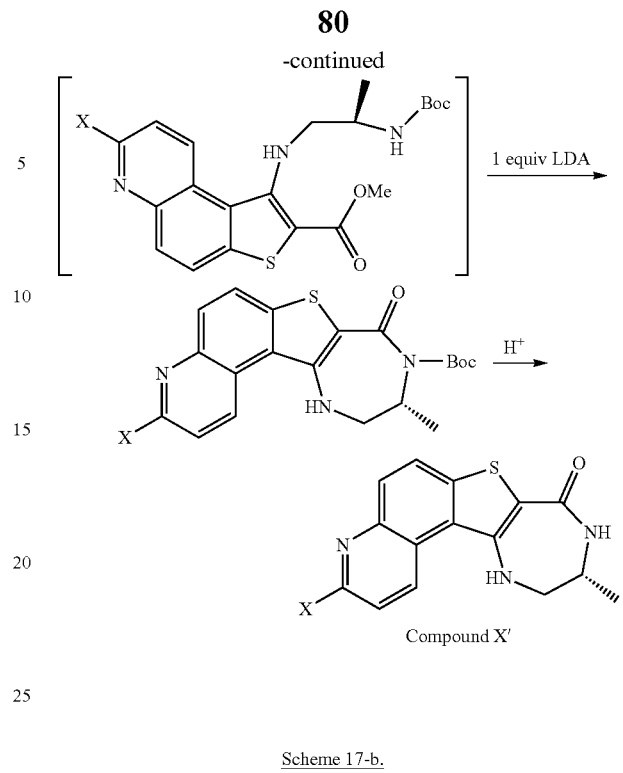
wherein each R', LG$^x$, and PG$^x$ is independently as described above and here.
Examples of methods described by Scheme 17 are provided in Scheme 17-a and Scheme 17-b.
Scheme 17-a.
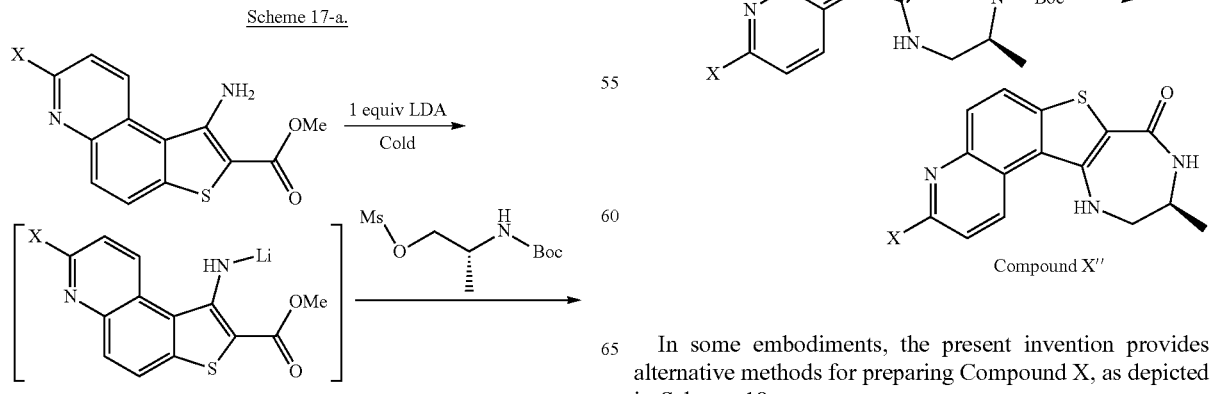
In some embodiments, the present invention provides alternative methods for preparing Compound X, as depicted in Scheme 18.

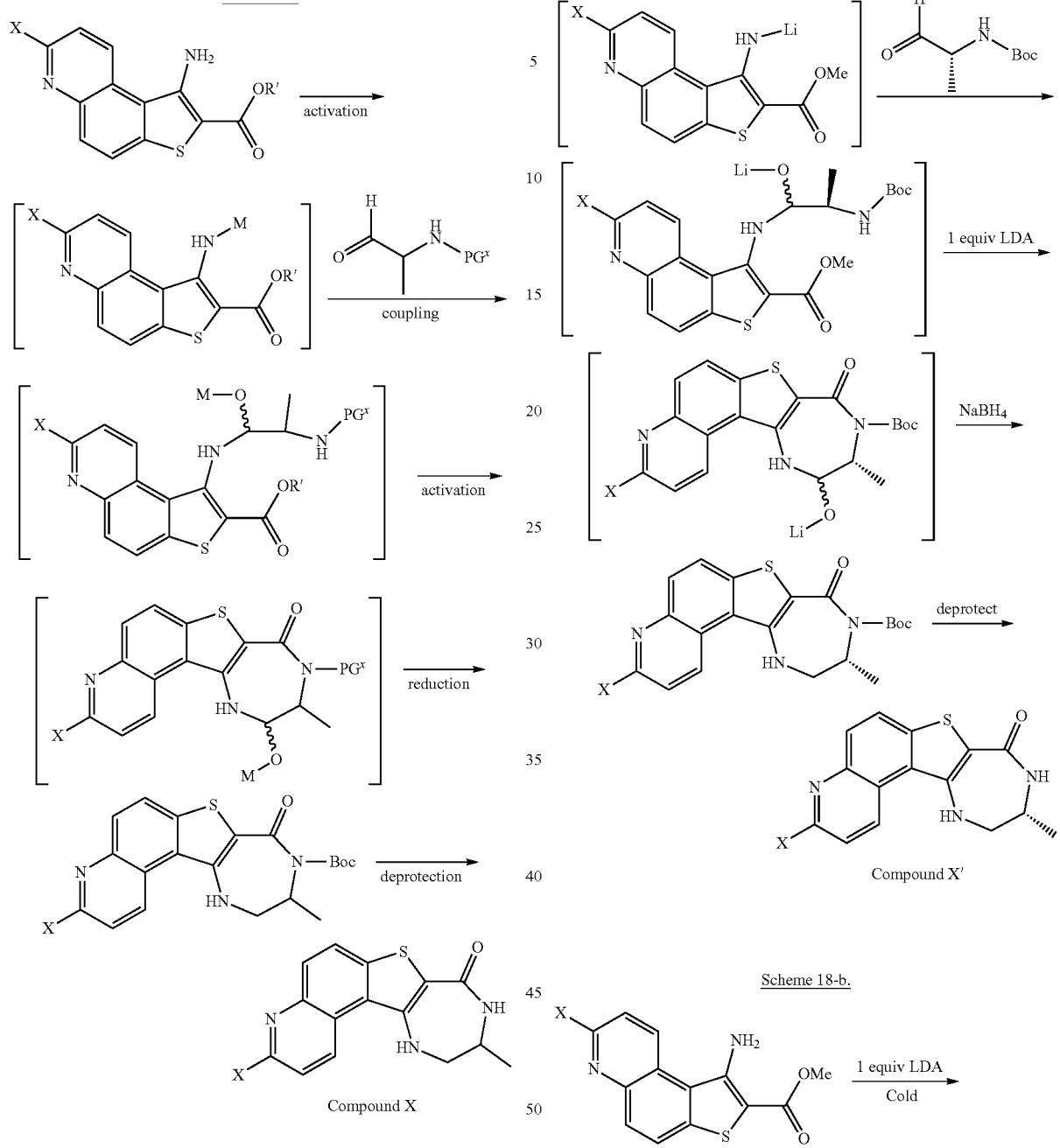
wherein each R', M, and PG$^x$ is independently as described above and herein.
Examples of methods described by Scheme 18 are provided in Scheme 18-a and Scheme 18-b.
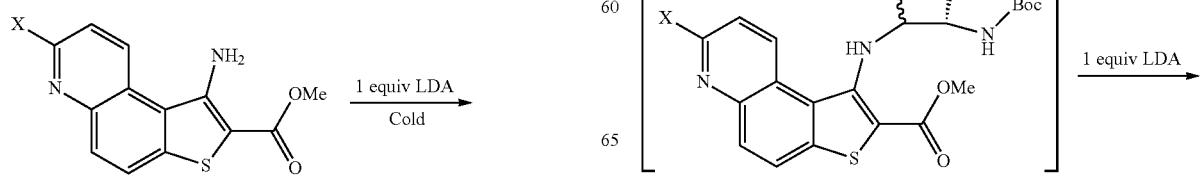

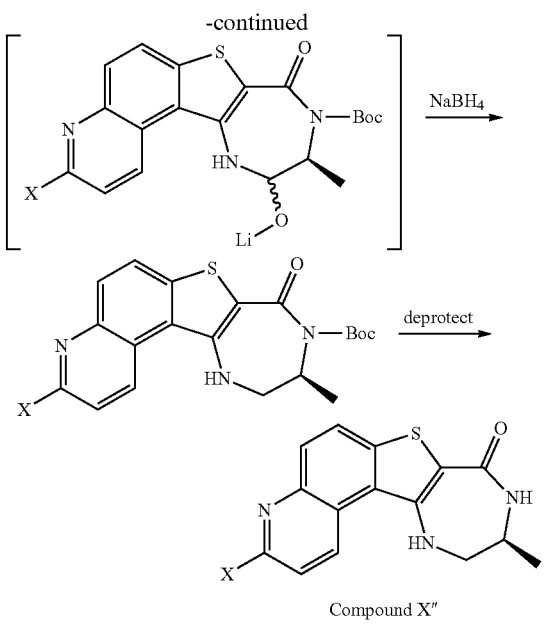

Compound X″

Uses, Formulation and Administration

Pharmaceutically Acceptable Compositions

According to another embodiment, the invention provides a composition comprising a compound of this invention or a pharmaceutically acceptable salt thereof and a pharmaceutically acceptable carrier, adjuvant, or vehicle. In certain embodiments, the amount of compound in compositions of this invention is such that it is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

Compounds and compositions, according to method of the present invention, are administered using any amount and any route of administration effective for treating or lessening the severity of a disorder provided herein (i.e., an MK2-mediated disease or disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage.

Compositions of the present invention may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this invention are administered without food. In other embodiments, pharmaceutically acceptable compositions of this invention are administered with food. Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a)

fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are set forth in the Examples, below.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating an MK2-mediated disease or disorder, in a patient in need thereof, comprising the step of administering to said patient a compound according to the present invention or pharmaceutically acceptable composition thereof. Such disorders are described in detail herein.

MK2 Kinase

MAP kinase-activated protein kinase 2 ("MK2") is an enzyme that in humans is encoded by the MAPKAPK2 gene. The MAPKAPK2 gene encodes a member of the Ser/Thr protein kinase family and two transcript variants encoding two different isoforms have been found. MK2 is regulated through direct phosphorylation by p38 MAP kinase.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS.

MK2 is known to be involved in many cellular processes including stress and inflammatory responses, nuclear export, gene expression regulation and cell proliferation. Indeed, MK2 regulates, by a post-transcriptional mechanism, biosynthesis of tumor necrosis factor α (TNFα) that is over-produced in inflammatory diseases such as rheumatoid arthritis and inflammatory bowel disease. See Natesan et al., *J Med. Chem.* 2012, 55, 2035-2047.

Compound I has been shown to inhibit phosphorylation of heat shock protein 27 (Hsp27). See Example 138 of WO 2016/044463. Inhibition of Hsp27 phosphorylation occurs by inhibiting the formation of the p38 kinase-MK2-Hsp27 signaling complex. Phosphorylation of Hsp27 is the penultimate event in a complex signaling cascade that occurs in response to extracellular stimuli. See Zheng et al., *The Journal of Biological Chemistry*, vol. 281, no. 48, 37215-37226, Dec. 1, 2006. Hsp27 usually exists as oligomers and plays a role in regulation of many cellular functions such as inhibition of the death receptor-mediated apoptosis, promotion of proper refolding of denatured proteins by acting as a molecular chaperone, and regulation of cytoskeleton. The presence of MK2 is a necessary condition for the formation of p38 kinase-MK2-Hsp27 signaling complex in cells. See Zheng et al., *The Journal of Biological Chemistry*, vol. 281, no. 48, 37215-37226, Dec. 1, 2006.

Evidence suggests that many signaling proteins form multimeric complexes. See Zheng et al., *The Journal of Biological Chemistry*, vol. 281, no. 48, 37215-37226, Dec. 1, 2006. One such complex is the Hsp27/Akt (a serine/threonine kinase) dimer, which forms in the cytoplasm of a cell. Another complex is formed between MK2 and p38. See Ben-Levy et al., *Current Biology* 1998, 8:1049-1057; Natesan et al., *J Med. Chem.* 2012, 55, 2035-2047; Zheng et al., *The Journal of Biological Chemistry*, vol. 281, no. 48, 37215-37226, Dec. 1, 2006.

In unstimulated conditions, inactive p38 and unphosphorylated MK2 form such dimer in the nucleus of a cell. Upon activation, p38 phosphorylates MK2, thereby inducing a conformational change of the autoinhibitory domain of MK2 and exposing the active site for substrate binding. Once MK2 is phosphorylated, the p38-MK2 dimer is translocated to the cytoplasm, where it forms a quaternary complex with the Hsp27-Akt dimer. See Zheng et al., *The Journal of Biological Chemistry*, vol. 281, no. 48, 37215-37226, Dec. 1, 2006. Hsp27 is then phosphorylated by MK2, resulting in degradation of the quaternary complex and the release of p-Hsp27 monomers and dimers. Because inhibition of MK2 blocks phosphorylation of Hsp27, without wishing to be bound by theory, it is believed that inhibition of MK2 prevents degradation of the p38-MK2-Akt-Hsp27 quaternary complex, thereby altering downstream effects. Consequent to the inhibition of quaternary complex degradation, the amount of quaternary complex would thereby increase.

Moreover, the equilibrium of p38 and MK2 between the cytoplasm and nucleus would be shifted towards the cytoplasm.

Interestingly, transport of the MK2/p38 complex out of the nucleus does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating an MK2-mediated disease or disorder in a patient in need thereof, wherein said method comprises administering to said patient a therapeutically effective amount of a provided compound, or composition thereof. Such MK2-mediated diseases or disorders include, but are not limited to those described herein.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behçet's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (for example, Meniere's disease), Goodpasture's syndrome, Graves' disease, HW-related autoimmune syndromes, Guillain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxicosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

EXEMPLIFICATION

Example 1

Synthesis of Compound 1-2

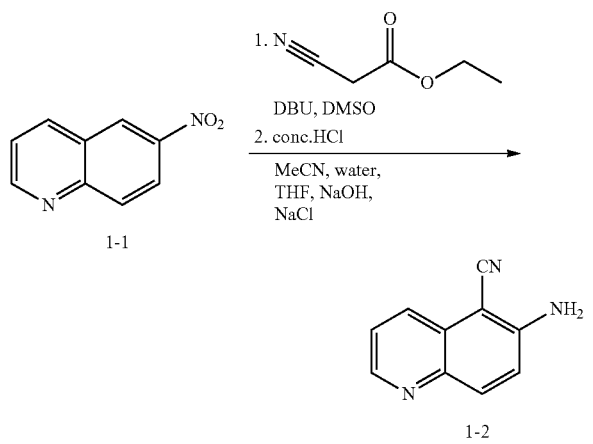

A mixture of 6-nitroquinoline 1-1 (450 g, 2.6 mol) and DBU (1.16 L, 7.8 mol) in DMSO (1.8 L) was warmed to 40 to 45° C. and ethyl cyanoacetate (690 mL, 6.5 mol) was added at a rate sufficient to maintain the batch temp. in the same range. At the end of the addition, the batch is cooled to 20-25° C. After 16 h, the batch was sampled by HPLC for full consumption of the starting material. Then, concentrated HCl (1.13 L, 13.5 mol) was added at a rate sufficient to maintain the batch temp. at 20-25° C. The batch was warmed to 80-90° C. and agitated for 4 h and then sampled for completion by HPLC. The batch was cooled to 20-30° C., acetonitrile (4.5 L) was added and the batch was further cooled to 0-5° C. and held for 2 h. The batch was filtered and the cake is rinsed with acetonitrile (2×900 mL) and dried under vacuum. The cake was transferred to a clean vessel and combined with THF (4.5 L) and water (1.8 L). Then, 10N aqueous NaOH solution was added at a rate sufficient to maintain the batch temperature less than 25° C. The batch was agitated, settled and split, and the upper organic phase was retained in the reactor. A 10% Aqueous NaCl solution (2.25 L) was charged to the vessel. The batch was agitated, settled and split, and the upper organic phase was retained in the reactor. The batch was then heated to reflux and continuously distilled at atmospheric pressure with the addition of water (4.5 L) to maintain a constant volume. The batch was cooled to 20-25° C. and the product was filtered. The cake was washed with water (2×900 mL) and dried under vacuum at 30-40° C. to afford compound 1-2, 440 g, in 65% yield.

$^1$H NMR (300 MHz, DMSO-$d_6$) δ 6.93 (s, 2H) 7.20-7.33 (m, 1H) 7.52 (dd, J=8.44, 4.31 Hz, 1H) 7.93 (s, 4H) 7.95-8.09 (m, 1H) 8.61 (dd, J=4.31, 1.56 Hz, 14H).

$^{13}$C NMR (75 MHz, DMSO-$d_6$) δ 82.9, 117.1, 122.0, 123.9, 129.4, 130.1, 135.7, 141.8, 146.8, 153.0.

MS: M+1 Calc: 170.2. Found: 170.0.

Example 2

Synthesis of Compound 1-3

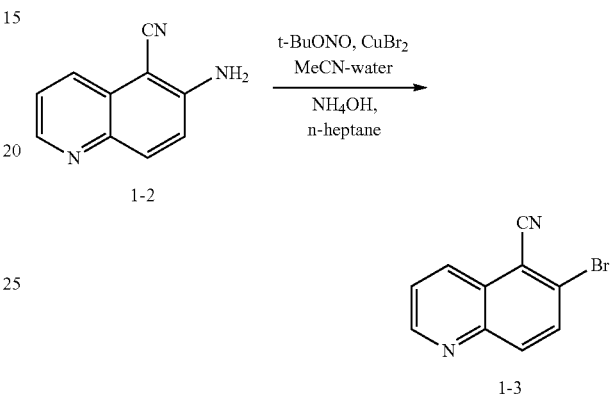

A mixture of compound 1-2 (80 g, 470 mmol) and copper (II) bromide (137 g, 620 mmol), acetonitrile (1.28 L) and water (320 mL) was warmed to 30-35° C. and agitated for 30-60 min. Tert-butyl nitrite (147 mL, 1.4 mol) was then added over 60 min. After the addition was completed, the mixture was stirred for 20 h and then sampled for completion by HPLC. The mixture was then warmed to 55-60° C. and held at this temperature for 1 h. Then, conc. ammonium hydroxide (240 mL) was added over 1 h, taking care to maintain the batch temperature under 60° C. The batch was stirred for 2 h and then cooled to 20-25° C., held for an additional 2 h, and the product was filtered. The cake was washed with water (3×400 mL) and heptane (400 mL), and the product was dried under vacuum at 30-40° C. to afford compound 1-3, 99 g, in 89% yield.

$^1$H NMR (300 MHz, CDCl$_3$-d) δ ppm 7.65 (dd, J=8.25, 3.85 Hz, 1H) 7.94 (d, J=8.99 Hz, 1H) 8.21 (d, J=9.08 Hz, 1H) 8.52 (d, J=8.53 Hz, 1H).

MS: M+1 Calc: 233.0/235.0. Found: 233.0/235.0.

Example 3

Synthesis of Compound 1-4

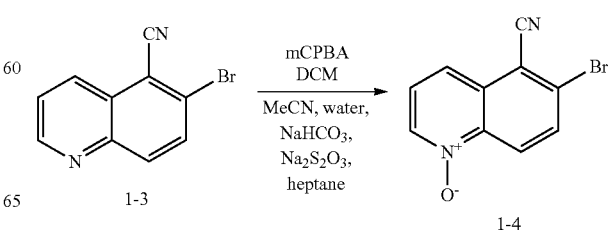

To a well agitated slurry of 6-bromoquinoline-5-carbonitrile 1-3 (50 g, 215 mmol) in dichloromethane (750 mL) at room temperature was charged a solution of mCPBA (69.1 g, 300 mmol of 77% mCPBA) in dichloromethane (350 mL) at a rate sufficiently slow to maintain the batch temperature under 25° C. The mixture was stirred at 20-25° C. for 24 h. The batch was sampled by HPLC for reaction completion. The mixture was warmed to 35° C. and distilled at 80-100 Torr to reduce the batch volume to ~500 mL. Then acetonitrile was slowly added while continuing to distill under reduced pressure, maintaining a constant batch volume at ~500 mL. After 1.1 L of acetonitrile was added, the batch was sampled by $^1$H NMR to ensure that the solvent mixture contained less than 7.5 mol % of dichloromethane. The batch was cooled to 20-25° C. and an aqueous solution of 10% $Na_2S_2O_3$ (350 mL) was charged to the batch and the mixture was agitated for a minimum of 2 h at 20-25° C. An aqueous solution of 5% $NaHCO_3$ (350 mL) was then added over 10-15 min and the mixture was agitated for a minimum of 4 h at 20-25° C. The batch was filtered and washed with MeCN:water (1:1) (350 mL) followed by water (350 mL) and then heptane (350 mL). The cake was dried at 40-45° C. under vacuum to afford the product compound 1-4, (41.5 g, 78% yield).

$^1$H NMR (300 MHz, DMSO-$d_6$) δ ppm 7.73 (dd, J=8.62, 6.14 Hz, 0H) 7.96 (d, J=8.71 Hz, 0H) 8.19 (d, J=9.44 Hz, 0H) 8.57-8.84 (m, 2H).

MS: M+1 Calc: 249.0/251.0. Found: 248.8/250.8.

Example 4

Synthesis of Compound 1-5

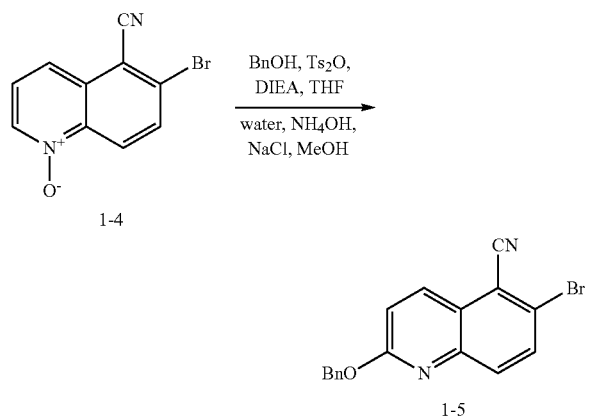

A mixture of 6-bromo-5-cyanoquinoline 1-oxide 1-4 (102 g, 411 mmol) and BnOH (1.0 L, 9.6 mol) was cooled to 3-7° C. and DIEA (215 mL, 1.25 mol) was added at a rate sufficient to maintain the batch temp. in the same range. Then, a solution of p-toluenesulfonic anhydride (201 g, 620 mmol) in THF (1.0 L) was added over a period of 2 h. At the end of the addition, the batch was warmed to 20-25° C. After 30 min, the batch was sampled by HPLC for reaction completion. Additional DIEA (215 mL, 1.25 mol) was added to the mixture, which was then warmed to 40-45° C. and 10% aq. $NH_4OH$ solution (1 L of a 10% $NH_3$ in water) was added. The batch was stirred at 40-45° C. for 45 min, and was then settled and the phases were split, retaining the upper organic phase in the reactor. 20% aqueous NaCl solution (510 mL) was charged to the reactor. The batch was agitated, settled and split, and the upper organic phase was retained in the reactor. The batch was heated to 70-75° C. and distilled at atmospheric pressure until THF stops distilling over. The batch was cooled to 40-45° C. and agitated until a thin slurry forms. Methanol (510 mL) was added over a period of 2 h and the slurry was agitated for 1 h. Water (510 mL) was added over a period of 2 h and the slurry was agitated for 1 h. The batch was cooled to 20-25° C., stirred for an additional 1 h and then filtered. The cake was washed with 1:1 MeOH/water (510 mL) and dried under vacuum at 30-40° C. to provide 104 g of compound 1-5, in 75% yield.

$^1$H NMR (300 MHz, DMSO-$d_6$) δ ppm 5.52 (s, 2H) 7.28-7.45 (m, 4H) 7.49-7.60 (m, 2H) 7.95-8.08 (m, 2H) 8.31 (d, J=9.08 Hz, 1H).

MS: M+1 Calc: 339.0/341.0. Found: 339.1/341.0.

Example 5

Synthesis of Compound 1-7

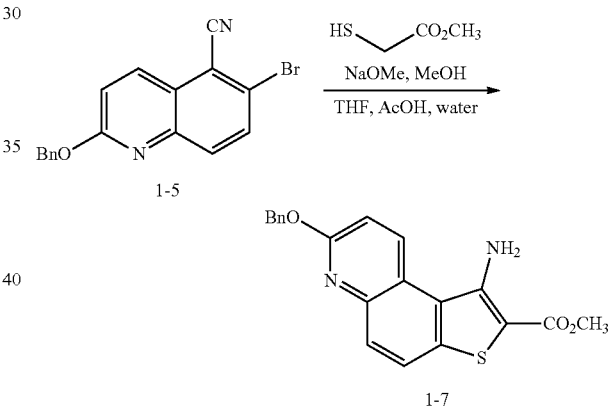

To a mixture of compound 1-5 (20 g, 59 mmol) and methyl 2-mercaptoacetate (9.9 g, 88 mmol) in THF (160 mL) was charged 25% sodium methoxide solution in methanol (17.5 mL, 77 mmol) slowly to maintain the reaction temperature of 20-25° C. The mixture was then heated to reflux for 2-4 hours and the batch was sampled for reaction completion by HPLC. The reaction mixture was cooled to 20-25° C. over 1 hour. Acetic acid (1.7 mL, 29.5 mmol) was added to quench the reaction. Then water (160 mL.) was added over 2 h. The batch was stirred at 20-25° C. for 16 hours and the product was filtered. The cake was washed with THF:water (1:2) (2×40 mL) and dried under vacuum at 30-40° C. to provide compound 1-7, 18.9 g, in 89% yield.

$^1$H NMR (300 MHz, DMSO-$d_6$) δ ppm 3.85 (s, 3H) 5.53 (s, 2H) 7.07 (br, 2H) 7.24 (d, J=9.08 Hz, 1H) 7.29-7.47 (m, 3H) 7.56 (d, J=6.97 Hz, 2H) 7.89 (d, J=8.89 Hz, 1H) 8.12 (d, J=8.89 Hz, 1H) 9.07 (d, J=9.17 Hz, 1H).

MS: M+1 Calc: 365.1. Found: 365.1.

Example 6

Version 1 Synthesis of Compound 1-9

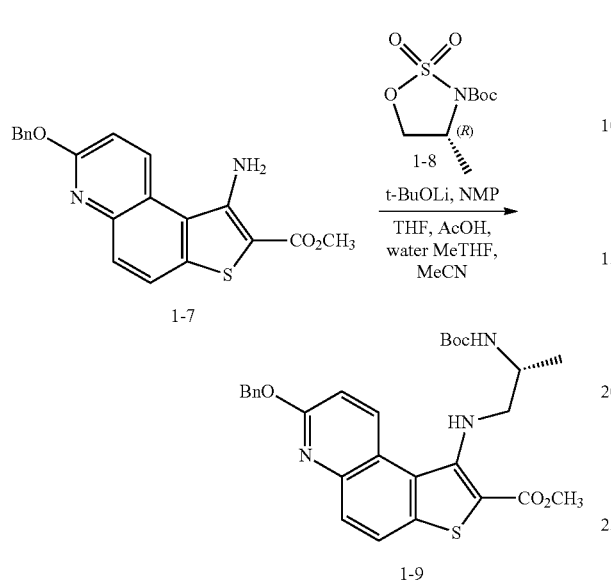

A mixture of compound 7 (100 g, 274 mmol) and compound 1-8 (73 g, 302 mmol) in NMP (400 mL) was cooled to −10–−15° C. Then, 2.2M t-BuOLi solution in THF (160 mL, 0.340 mmol) was charged over 90 min. The mixture was stirred for additional 30 min at the same temperature and was then sampled for conversion by HPLC. The reaction was quenched with acetic acid (20 mL, 340 mmol) and warmed to 20-25° C. The mixture was partitioned between 2-MeTHF (1 L) and 2% aqueous NaCl (500 mL), and the organic phase was washed with 5% aqueous NaCl (2×500 mL) and water (500 mL). The batch was heated to reflux and distilled at atmospheric pressure until the batch volume is reduced to 500 mL. The batch was then distilled at constant volume with addition of acetonitrile (1 L) and then sampled by $^1$H NMR to ensure that the solvent composition contains less than 5 mol % 2-MeTHF. Additional acetonitrile (1.5 L) was added to bring the total batch volume to 2.0 L. The batch was cooled to 60-65° C. and seeded with compound 1-8 seed (2.0 g, 4.0 mmol). The batch was held at 60-65° C. for 1 h and cooled to 20-25° C. over 6 h. The batch was heated back to 60-65° C. and held for 2 h and then cooled to 20-25° C. over 6 h. The batch was filtered, washed with acetonitrile (2×00 mL) and dried in vacuo at 35-40° C. for 16-18 to provide compound 1-9, 122.3 g, in 85% yield.

$^1$H NMR (300 MHz, DMSO-d$_6$) δ ppm 1.00 (d, J=6.51 Hz, 3H) 1.06-1.51 (m, 9H) 3.10 (t, J=6.42 Hz, 2H) 3.54-3.74 (m, 1H) 3.89 (s, 3H), 5.54 (s, 2H) 6.52 (t, J=6.56 Hz, 1H) 6.80 (d, J=8.25 Hz, 1H) 7.24 (d, J=9.08 Hz, 1H) 7.29-7.47 (m, 3H) 7.50-7.64 (m, 2H) 7.89 (d, J=8.99 Hz, 1H) 8.16 (d, J=8.89 Hz, 1H) 8.99 (d, J=9.17 Hz, 1H)

MS: M+1 Calc: 522.2. Found: 522.2.

Example 7

Version 1 Synthesis of Compound 1-10-1

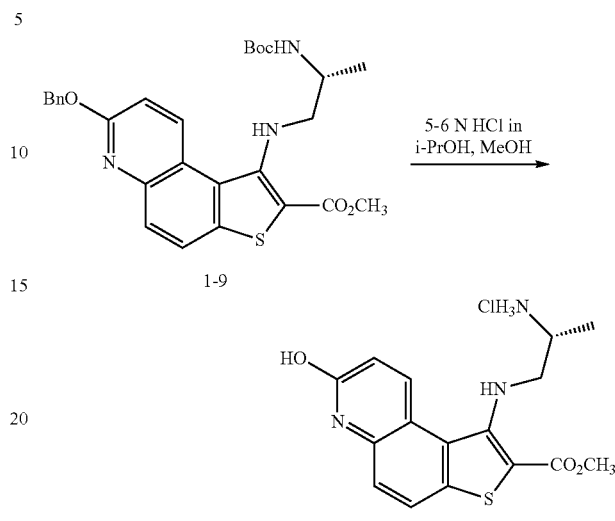

To a mixture of compound 1-9 (100 g, 192 mmol) in methanol (1.0 L) was charged 5-6 N HCl in isopropanol (128 mL, 767 mmol) at ambient temperature. The mixture was stirred for 15 min and then heated to reflux and held with stirring for 20 h. The batch was sampled for conversion by HPLC and was then cooled to 20-25° C. The mixture was filtered and the cake was washed with methanol (2×200 mL) and dried under vacuum at 35-40° C. for 16 h to afford 68.1 g of compound 1-10-1, in 97% yield.

$^1$H NMR (300 MHz, DMSO-d$_6$) δ ppm 1.21 (d, J=6.51 Hz, 3H) 2.98 (dd, J=12.75, 7.52 Hz, 1H) 3.10-3.25 (m, 1H) 3.25-3.40 (m, 1H) 3.82 (s, 3H) 6.53-6.82 (m, 1H) 7.36-7.57 (m, 1H) 7.83-8.01 (m, 1H) 8.65 (d, J=9.81 Hz, 1H).

MS: M+1 Calc: 332.1. Found: 332.1.

Example 8

Version 1 Synthesis of Compound 1-11

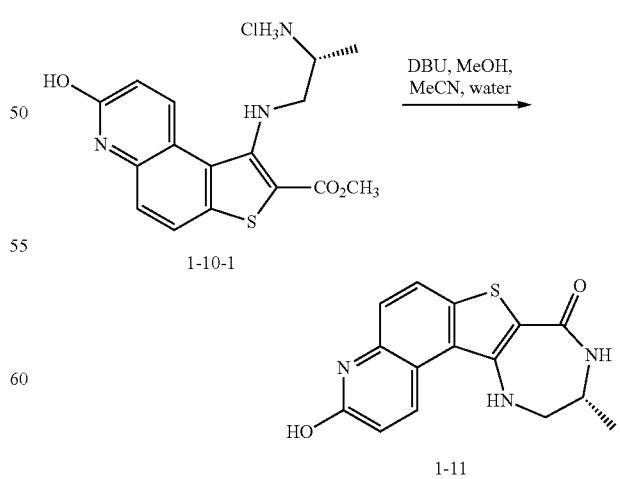

A mixture of compound 1-10-1 (4.0 g, 10.9 mmol) in methanol (100 mL) was stirred at 20-25° C. and DBU (8.20 mL, 54.4 mmol) was added dropwise at a rate sufficient to maintain the batch temp. within the same range. Then the batch was heated to 60-70° C. and stirred at this temperature for 40 h. The batch was cooled to 35-40° C. and distilled under reduced pressure until the batch volume was reduced to 16-20 mL. Then acetonitrile (90 mL) was added slowly and the batch was heated to 70-75° C. for 20 h. The mixture was cooled to 20-25° C., aged for 1 h, and was then filtered. The cake was washed with water (2 mL) and 1:1 acetonitrile-methanol (2 mL) and dried under vacuum at 40-50° C. for 30 h to afford compound 1-11, 3.0 g as a yellow solid, in 92% yield.

$^1$H NMR (300 MHz, DMSO-$d_6$) δ ppm 1.16 (d, J=6.79 Hz, 3H) 3.39 (br. s., 2H) 3.50-3.60 (m, 1H) 6.60 (d, J=9.90 Hz, 1H) 6.85 (t, J=5.27 Hz, 1H) 7.43 (d, J=8.80 Hz, 1H) 7.92 (d, J=8.71 Hz, 1H) 8.07 (d, J=4.22 Hz, 1H) 8.80 (d, J=10.00 Hz, 1H), 12.02 (br, 1H).

MS: M+1 Calc: 300.1. Found: 300.0.

Example 9

Version 2 Synthesis of Compound 1-10-2

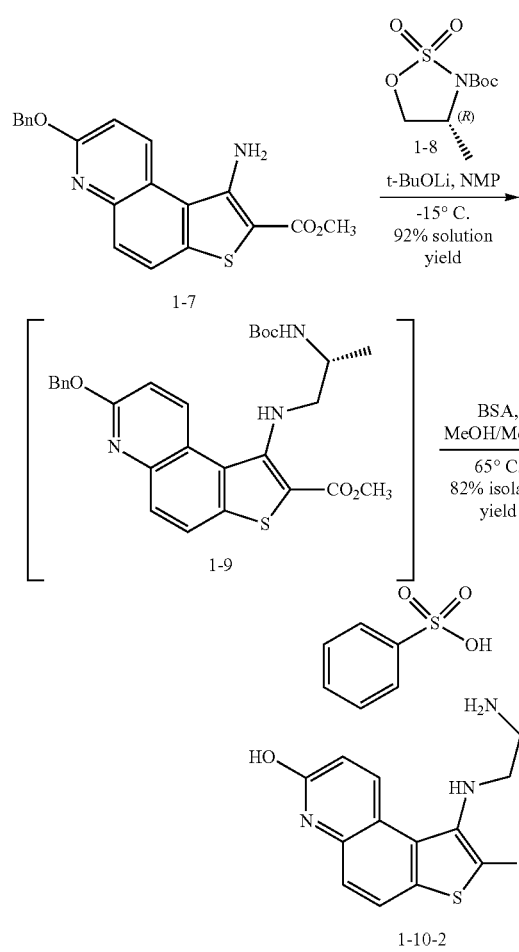

A mixture of compound 1-7 (100 g, 274 mmol) and compound 1-8 (71.6 g, 302 mmol) in NMP (400 mL) was cooled to −10-−15° C. Then, 2.2 M t-BuOLi solution in THF (156 mL, 343 mmol) was charged over 90 min maintaining a temperature between −10-−15° C. The reaction was sampled by HPLC for completion and then quenched with 1:1 v/v acetic acid-THF (38.8 mL, 343 mmol) and warmed to 0-5° C. The mixture was partitioned between 2-MeTHF (1.0 L) and 2.5% aqueous LiCl (500 mL). The aqueous phase was back extracted with 100 mL vol 2-MeTHF. The organic phases were combined and washed with 5% aqueous LiCl (500 mL Vol.) two times and once with water (500 mL). The batch was heated to reflux and distilled at atmospheric pressure until the batch volume was reduced to 500 mL. Acetonitrile (500 mL) was added and the batch was distilled at constant volume with addition of acetonitrile (1.2 L) and then sampled by NMR to ensure that the 2-MeTHF content in the solvent composition is less than 2.5 mol %. Additional acetonitrile (200 mL) was added to bring the total batch volume to 1.2 L. The batch was cooled to 65-70° C. and a solution of BSA (78 g, 494 mmol) in MeOH (200 mL) was added dropwise. Additional MeOH (200 mL) was then added dropwise as a rinse and to bring the total batch volume to 1.6 L. The reaction was stirred at 65 to 70° C. for 16 h and was then monitored by HPLC for completion of reaction. Once complete, the reaction was cooled to 20-25° C. over 2 h, held for 1 h and then filtered. The yellow filter cake was then washed with 3:2 MeCN/MeOH (2×200 mL). The final wet cake was then dried under vacuum at 40-45° C. to provide 109 g of compound 1-10-2, in 81% yield.

$^1$H NMR (300 MHz, DMSO-$d_6$) δ ppm 1.25 (d, J=6.33 Hz, 3H) 3.00-3.18 (m, 1H) 3.28 (d, J=7.34 Hz, 1H) 3.34-3.37 (m, 1H), 3.90 (s, 3H) 6.24 (t, J=6.92 Hz, 1H) 6.70 (d, J=9.90 Hz, 1H) 7.19-7.36 (m, 3H) 7.51-7.64 (m, 3H) 7.85 (br. s., 3H) 8.09 (d, J=8.89 Hz, 1H) 8.68 (d, J=9.90 Hz, 1H) 12.14 (s, 1H).

MS: M+1 Calc: 332.1. Found: 332.1.

Example 10

Version 2 synthesis of compound 1-11

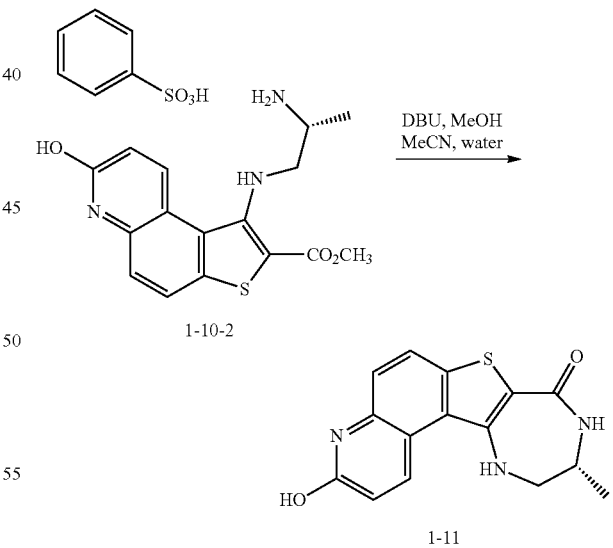

A mixture of compound 1-10-2 (1.5 kg, 3.1 mol) in methanol (30 L) was stirred at 20-30° C. and DBU (2.25 L, 15.4 mol), was added slowly, maintaining the batch temperature under 35° C. The resulting suspension was heated to 60-65° C. for 24-30 h under nitrogen. The reaction was sampled by HPLC to ensure that less than 2% starting material remains. The reaction was then cooled to 20-30° C. and filtered. The cake was washed with MeOH (7.5×L) and deliquored. The wet cake was transferred to a visually clean reactor, and then acetonitrile (30 L) and MeOH (7.5 L were added) and the batch was stirred at 20-30° C. were added while DBU (0.45 L, 3.0 mol). Heat the suspension, with overhead agitation to reflux (65-70° C.) for 18-24 h. The mixture is sampled by HPLC to ensure that less than 0.5% starting material remains. The reaction is cooled to 20-30° C. and filtered. The cake is washed with water (7.5 L), MeOH:MeCN (1:1 v/v, 7.5 L), deliquored and dried in oven under vacuum at 45-55° C. for 18-24 h to afford compound 1-11, 820 g as a yellow solid in 89% yield.

$^1$H NMR (300 MHz, DMSO-$d_6$) δ ppm 1.16 (d, J=6.79 Hz, 3H) 3.39 (br. s., 2H) 3.50-3.60 (m, 1H) 6.60 (d, J=9.90 Hz, 1H) 6.85 (t, J=5.27 Hz, 1H) 7.43 (d, J=8.80 Hz, 1H) 7.92 (d, J=8.71 Hz, 1H) 8.07 (d, J=4.22 Hz, 1H) 8.80 (d, J=10.00 Hz, 1H), 12.02 (br, 1H).

MS: M+1 Calc: 300.1. Found: 300.0.

Example 11

Synthesis of Compound I.

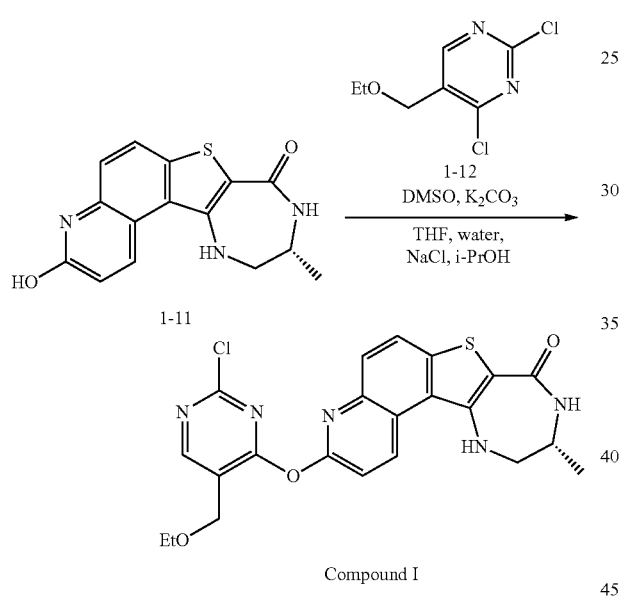

Compound I

A mixture of compound 1-11 (55 g, 184 mmol), compound 1-12 (45.7 g, 220 mmol), potassium carbonate (30.5 g, 220 mmol) and DMSO (550 mL) was stirred at ambient temperature for 15 min and then warmed to 40-45° C. for 7 h. The mixture was cooled to 20-25° C. and stirred for 10 h. The mixture was sampled by HPLC for completion of reaction. The batch was then warmed to 40-45° C. and water (550 mL) and THF were added, maintaining the batch temperature in the same range. The biphasic mixture was agitated for 15 then allowed to settle and the phases were split. The lower aqueous phase was transferred back to the vessel and was back-extracted with THF (550 mL). The combined organic phases were washed with a 10% aqueous NaCl solution (2×550 mL) and filtered to remove suspended solids. The filtrate was transferred to a clean reactor and distilled under atmospheric pressure until the batch volume was reduced to 440 mL. The batch was seeded with compound I (1.1 g, 2.3 mmol). Then the batch was distilled under atmospheric pressure with addition of isopropanol (1.1 L) to maintain the batch at constant volume. The batch was sampled by NMR to ensure that the THF content was less than 3 mol % of the solvent composition. Then the batch was agitated at 80-85° C. for 1 h, cooled to 20-25° C. over 3 h, and agitated at 20-25° C. for 16 h. The batch was filtered and the cake was washed with isopropanol (2×110 mL) and dried under vacuum at 40-45° C. for 16 h to provide 69.8 g of compound I, in 81% yield.

$^1$H NMR (300 MHz, DMSO-$d_6$) δ ppm 1.12-1.25 (m, 6H) 3.42-3.50 (m, 2H) 3.61 (q, J=6.97 Hz, 3H) 4.65 (s, 2H) 7.17 (t, J=5.18 Hz, 1H) 7.63 (d, J=9.08 Hz, 1H) 7.86 (d, J=8.89 Hz, 1H) 8.15 (d, J=4.40 Hz, 1H) 8.18 (d, J=8.90 Hz, 1H) 8.71 (s, 1H) 9.36 (d, J=9.08 Hz, 1H).

MS: M+1 Calc: 470.10/472.10. Found: 470.10/472.20.

Example 12

Alternative Synthesis of Compound I.

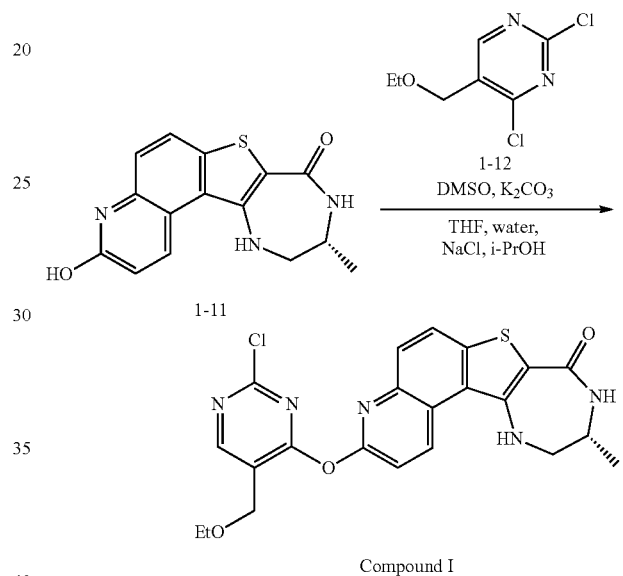

Compound I

A mixture of compound 1-11 (100 g, 334 mmol), compound 1-12 (83 g, 401 mmol), potassium carbonate (55 g, 401 mmol), DMSO (500 mL) and THF (500 mL) was stirred at ambient temperature for 15 min and then warmed to 40-45° C. for 22 h. The mixture was sampled by HPLC for completion of reaction. The mixture was cooled to 20-25° C. and filtered through a bed a Celite (10 g). The reactor was washed with 100 mL of (8:2) THF/DMSO and filtered. Finally the Celite cake was washed with 100 mL (8:2) THF/DMSO followed by 100 mL of THF. The filtrate was transferred to a clean reactor, followed by THF (700 mL). The batch was then warmed to 40-45° C. and 10% aqueous NaCl (500 mL) was added, maintaining the batch temperature in the same range. The biphasic mixture was agitated for 15 min then allowed to settle and the phases were split, leaving the upper organic phase in the reactor. Then THF (500 mL) and 10% aqueous NaCl (500 mL) were added, maintaining the batch temperature in the same range. The biphasic mixture was agitated for 15 min then allowed to settle and the phases were split, leaving the upper organic phase in the reactor. THF (500 mL) and 10% aqueous NaCl (200 mL) were added, maintaining the batch temperature in the same range. The biphasic mixture was agitated for 15 min then allowed to settle and the phases were split, leaving the upper organic phase in the reactor. The batch was then distilled under atmospheric pressure until the batch volume was reduced to 800 mL. The batch was seeded with compound I (2.0 g, 4.3 mmol). Then the batch was distilled under atmospheric pressure with addition of isopropanol (2.0 L) to maintain the batch at constant volume. The batch was sampled by GC to ensure that the THF content was less than 6 wt % of the solvent composition. Then the batch was agitated at 80-85° C. for 1 h, cooled to 20-25° C. over 3 h, and agitated at 20-25° C. for 16 h. The batch was filtered and the cake was washed with isopropanol (200 mL) and then water (200 mL), and dried under vacuum at 40-45° C. for 16 h to provide 134.7 g of the crude product, in 86% yield.

A mixture of crude compound I (75 g, 160 mmol), THF (675 mL) and water (75 mL) was heated to 55-65° C. and agitated until formation of a clear solution. The batch was cooled to 40° C. and seeded with the THF solvate form of compound I (1.5 g, 2.7 mmol). After 20 min, the batch was cooled to 20° C. over 2 h and held at 20° C. for 30 min. Then the mixture was heated to 40° C. over 30 min and held at this temperature for 30 min and then cooled to 20° C. over 2 h and held for 14 h. The batch was warmed back to 40° C. over 30 min and water (938 mL) was charged over 8 h. The batch was cooled to 20° C. over 2 h and filtered. The reactor was washed with water: THF (2:1 by vol, 150 mL) and this wash was used to rinse the cake. The cake was then washed with water (2×150 mL) and dried under vacuum at 50-55° C. to afford 75.6 g of the THF solvate, in 88% yield.

A mixture of THF solvate (29.0 g, 54.6 mmol) and acetone (290 mL) was agitated in the presence of the anhydrate form of compound I (250 mg, 0.5 mmol) and the resulting mixture was heated to 50-55° C. and agitated at this temperature for 48 h. The mixture was sampled by XRPD to assess conversion to the anhydrate form. Then the batch was cooled to 20-25° C. over 2 h and held at that temperature for 16 h. The batch was filtered and the cake was rinsed with acetone (2×60 mL). The cake was dried under vacuum at 45-55° C. to afford 24.0 g of the anhydrate form of compound I as a yellow solid, in 94% yield.

$^1$H NMR (300 MHz, DMSO-$d_6$) δ ppm 1.12-1.25 (m, 6H) 3.42-3.50 (m, 2H) 3.61 (q, J=6.97 Hz, 3H) 4.65 (s, 2H) 7.17 (t, J=5.18 Hz, 1H) 7.63 (d, J=9.08 Hz, 1H) 7.86 (d, J=8.89 Hz, 1H) 8.15 (d, J=4.40 Hz, 1H) 8.18 (d, J=8.90 Hz, 1H) 8.71 (s, 1H) 9.36 (d, J=9.08 Hz, 1H).

MS: M+1 Calc: 470.10/472.10. Found: 470.10/472.20.

Example 13

(S)-3-((2-chloro-5-(ethoxymethyl)pyrimidin-4-yl)oxy)-10-methyl-9,10,11,12-tetrahydro-8H-[1,4]diazepino[5',6':4,5]thieno[3,2-f]quinolin-8-one

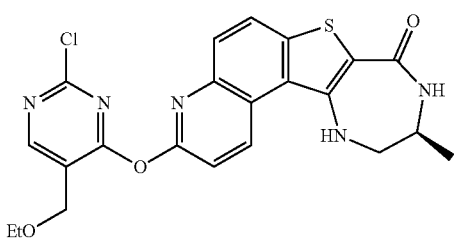 [SMILES: CCOCc1cnc(Cl)nc1Oc1ccc2c(ccc3sc4c(c32)NC[C@H](C)NC4=O)n1]

Step 1: Preparation of (S)-methyl 1-((2-aminopropyl)amino)-7-hydroxythieno[3,2-f]quinoline-2-carboxylate Benzenesulfonate

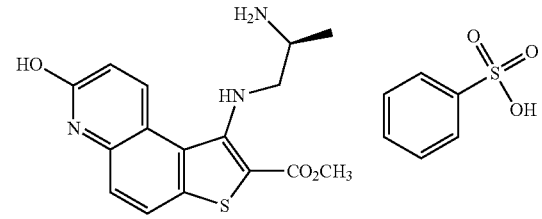 [SMILES: COC(=O)c1sc2ccc3nc(O)ccc3c2c1NC[C@H](C)N ; O=S(=O)(O)c1ccccc1]

A hazy brown mixture of methyl 1-amino-7-(benzyloxy)thieno[3,2-f]quinoline-2-carboxylate (100 g, 274 mmol), (S)-tert-butyl 4-methyl-1,2,3-oxathiazolidine-3-carboxylate 2,2-dioxide (73.0 g, 302 mmol) in anhydrous NMP (400 ml, 4127 mmol) was stirred at ambient temperature for 30 minutes, followed by cooling the mixture to −15° C. to −20° C. Then a cloudy mixture of lithium tert-butoxide (27.4 g, 343 mmol) in anhydrous THF (135 ml) was charged over 90 min while keeping the reaction mixture less than −10° C. The reaction was kept at −10° C. for additional one hour and then quenched with acetic acid (19.6 ml, 343 mmol) over 10 minutes and then warmed to 20-25° C. over 30 minutes. The mixture was partitioned between 2-MeTHF (1000 ml) and 2.5% aqueous LiCl (500 ml). The aqueous phase was back extracted with 100 ml of 2-MeTHF. The organic phases were combined and washed two times with 5% aqueous LiCl (500 ml) and once with water (500 ml). The batch was heated to reflux and distilled at ~85° C. under atmospheric pressure until the batch volume was reduced to ~500 ml, followed by distillation at constant volume with addition of acetonitrile (1200 ml). Additional acetonitrile (200 ml) was added to bring the total batch volume to ~700 ml. The batch was cooled to 60-65° C. and a solution of benzenesulfonic acid (82 g, 494 mmol) in MeOH (200 ml) was added dropwise over 30 minutes. Additional MeOH (100 ml) was then added dropwise as a rinse and to bring the total batch volume to ~1000 ml. The reaction was held at 65-70° C. for at least 16 hours then cooled to 20-25° C. over 2 hours, held for 1 h and then filtered. The yellow filter cake was then washed twice with (200 ml) 3:2 MeCN/MeOH. The final wet cake was then dried in a vacuum oven at 40° C. with a slow bleed of nitrogen for 12-16 hours to give a yellow solid (115.8 g, 86% yield); mp 283-285° C.; HPLC: Waters Ascentis Express C-18 HPLC column, 10 cm×4.6 rpm, 1 mL/min, 234 nm, gradient at 100% 0.1% $H_3PO_4$ to 100% $CH_3CN$ in 10 min, then hold at 100% $CH_3CN$ for 5 min): $t_R$=3.65 min (99.4%). $^1$H NMR (300 MHz, DMSO-$d_6$) δ ppm 1.25 (d, J=6.33 Hz, 3H) 3.02-3.19 (m, 1H) 3.22-3.44 (m, 2H) 3.90 (s, 3H) 6.25 (t, J=6.97 Hz, 1H) 6.71 (d, J=9.90 Hz, 1H) 7.25-7.40 (m, 3H) 7.51-7.66 (m, 3H) 7.85 (br s, 3H) 8.10 (d, J=8.80 Hz, 1H) 8.69 (d, J=9.90 Hz, 1H) 12.15 (s, 1H). $^{13}$C NMR (DMSO-$d_6$) δ 16.90, 47.28, 52.63, 52.85, 114.71, 114.95, 118.15, 122.45, 125.91, 126.29, 128.09, 128.58, 128.86, 134.24, 136.05, 138.54, 148.71, 151.46, 161.61, 164.53. LC/MS m/e$^+$=332. Anal. Calcd. for $C_{22}H_{23}N_3O_6S_2$: C, 53.98; H, 4.74; N, 8.58; S, 13.10. Found: C, 53.97; H, 4.92; N, 8.52; S, 12.96.

Step 2: Preparation of (S)-3-hydroxy-10-methyl-9,10,11,12-tetrahydro-8H-[1,4]diazepino[5',6':4,5]thieno[3,2-f]quinolin-8-one

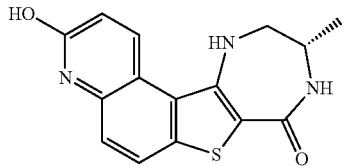 [SMILES: C[C@H]1CNc2c(sc3ccc4nc(O)ccc4c23)C(=O)N1]

To a stirred yellow slurry of (S)-methyl 1-((2-aminopropyl)amino)-7-hydroxythieno[3,2-f]quinoline-2-carboxylate benzenesulfonate (110.3 g, 225 mmol) in methanol (2200 ml, 225 mmol) at ambient temperature under nitrogen was charged 2,3,4,6,7,8,9,10-octahydropyrimido[1,2-a]azepine ("DBU", 158 ml, 1127 mmol) slowly over 5 minutes with rapid agitation (300-400 rpm) while keeping temperature less than 35° C. The mixture was then heated to reflux (65-70° C.) for 24-36 hours until the benzenesulfonate was no more than 2% area by HPLC. If not met, heat for additional 18-24 hours. The batch was cooled to 20-30° C. over one hour and filtered. The cake was washed with MeOH (550 ml) and deliquored. The wet cake was transferred to a visually clean reactor and charged with MeCN (2200 ml), MeOH (550 ml) and 2,3,4,6,7,8,9,10-octahydropyrimido[1,2-a]azepine (33 ml). The mixture was heated to reflux (65-70° C.) for 18-24 hours until the benzenesulfonate was not more than 0.5% area by HPLC. The batch was cooled to 20-30° C. and filtered. The cake was washed with water (550 ml), MeOH:MeCN (1:1 v/v, 550 vol), deliquored and dried oven under vacuum at 45-55° C. for 18-24 hours to afford a yellow solid (62.6 g, 93% yield); HPLC: Waters Ascentis Express C-18 HPLC column, 10 cm×4.6 μm, 1 mL/min, 254 nm, gradient at 100% 0.1% $H_3PO_4$ to 100% $CH_3CN$ in 10 min, then hold at 100% $CH_3CN$ for 5 min): $t_R$=2.87 min (98.9%). $^1$H NMR (300 MHz, DMSO-$d_6$) δ ppm 1.16 (d, J=6.79 Hz, 3H) 3.33 (s, 3H) 3.38 (br d, J=4.68 Hz, 2H) 3.56 (br dd, J=6.60, 3.48 Hz, 1H) 6.60 (d, J=9.90 Hz, 1H) 6.86 (t, J=5.41 Hz, 1H) 7.43 (d, J=8.71 Hz, 1H) 7.93 (d, J=8.80 Hz, 1H) 8.08 (d, J=4.22 Hz, 1H) 8.80 (d, J=10.00 Hz, 1H) 12.05 (s, 1H); $^{13}$C NMR (DMSO-$d_6$) δ 19.11, 48.50, 52.39, 115.08, 116.57, 121.35, 125.90, 128.02, 134.45, 135.97, 138.41, 143.91, 161.42, 164.50. LC/MS m/e+=300. Anal. Calcd. for $C_{15}H_{13}N_3O_2S$: C, 60.19; H, 4.38; N, 14.04; S, 10.71. Found: C, 59.60; H, 4.07; N, 13.69; S, 10.38.

Step 3: Preparation of (S)-3-((2-chloro-5-(ethoxymethyl)pyrimidin-4-yl)oxy)-10-methyl-9,10,11,12-tetrahydro-8H-[1,4]diazepino[5',6':4,5]thieno[3,2-f]quinolin-8-one (I')

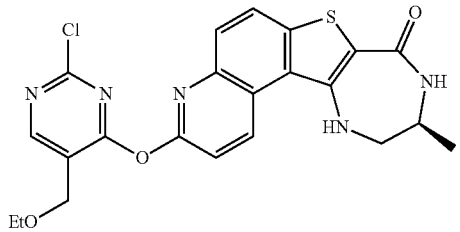 [SMILES: CCOCc1cnc(Cl)nc1Oc1ccc2c(ccc3sc4c(c32)NC[C@H](C)NC4=O)n1]

A yellow slurry mixture of (S)-3-hydroxy-10-methyl-9,10,11,12-tetrahydro-8H-[1,4]diazepino[5',6':4,5]thieno[3,2-f]quinolin-8-one (30 g, 100 mmol), 2,4-dichloro-5-(ethoxymethyl)pyrimidine (24.90 g, 120 mmol), and potassium carbonate (325 mesh) (16.96 g, 120 mmol) in DMSO (150 ml, 2114 mmol) and THF (150 ml, 1831 mmol) was stirred at ambient temperature for 5-10 minutes, followed by heating at 40-45° C. for at least 16 hours with sufficient agitation (350-400 rpm). The yellow/tan slurry mixture was then cooled to 20-25° C., and filtered over 9 g of Celite (prewetted with 15 mL of THF). The yellow filtrate (~400 ml) was transferred back to the visually clean jacketed flask along with 240 mL of THF, and was heated to 40-45° C. over 30 minutes. To the mixture was charged 150 mL of 10 wt % aqueous NaCl, stirred for 5 minutes and settled for phase split. After the bottom aqueous phase was removed, 150 mL of THF and 150 mL of 10 wt % aqueous NaCl were charged and stirred at 40-45° C. for 5 minutes. The aqueous phase was removed again. Then, 90 mL of THF and 50 mL of 10 wt % aqueous NaCl were charged, maintaining the batch temp at 40-45° C. (lower temp will make product crystallize out). The aqueous phase was removed and the remaining organic portion was distilled under atmospheric pressure at 65-70° C. to ~300 ml. The batch was seeded with 200 mg of the product and the resulting mixture was aged for one hour. Then the batch was distilled with addition of isopropanol (600 ml) at a rate sufficient to maintain a constant batch volume. The slurry was cooled from ~70° C. to 22° C. over 4 hours, hold at 22° C. for 16 hours and filtered, washed with 3×30 mL of IPA, and dried in a vacuum oven at 40-45° C. for 12-16 hours to afford compound I' as a yellow solid (41.1 g, 87% yield); HPLC: Waters Ascentis Express C-18 HPLC column, 10 cm×4.6 m, 1 mL/min, 234 nm, gradient at 100% 0.1% $H_3PO_4$ to 100% $CH_3CN$ in 10 min, then hold at 100% $CH_3CN$ for 5 min): $t_R$=6.40 min (99.0%). $^1$H NMR (300 MHz, DMSO-$d_6$) δ ppm 1.13-1.27 (m, 6H) 3.42-3.54 (m, 2H) 3.57-3.70 (m, 3H) 4.66 (s, 2H) 7.18 (br t, J=5.18 Hz, 1H) 7.64 (d, J=9.08 Hz, 1H) 7.87 (d, J=8.89 Hz, 1H) 8.12-8.23 (m, 2H) 8.72 (s, 1H) 9.37 (d, J=9.17 Hz, 1H); $^{13}$C NMR (75 MHz, DMSO-$d_6$) δ ppm 15.47, 19.12, 48.46, 52.39, 64.02, 66.28, 114.87, 115.10, 119.60, 124.30, 126.49, 126.75, 127.7, 135.77, 139.30, 145.00, 145.84, 156.32, 158.02, 160.48, 164.52, 167.37. LC/MS m/e+=470. Anal. Calcd. for $C_{22}H_{20}N_5O_3SCl$: C, 56.23; H, 4.29; N, 14.90; S, 6.82; Cl, 7.54. Found: C, 55.87; H, 4.33; N, 14.61; S, 6.60.

Enumerated Embodiments

1. A method for preparing compound I:

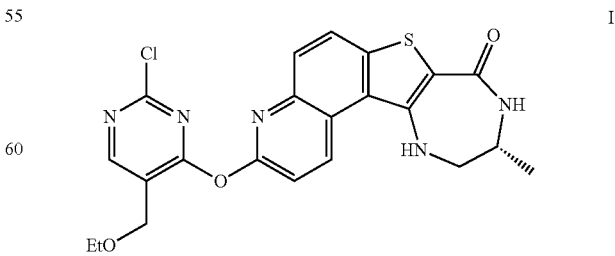

or a pharmaceutically acceptable salt thereof, comprising the steps of: reacting a compound of formula 1-11:

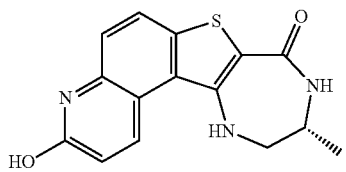

or a pharmaceutically acceptable salt thereof;
with a compound of formula 1-12,

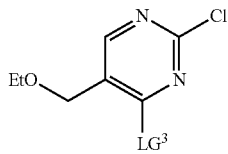

wherein LG³ is a suitable leaving group;
under suitable reaction conditions to provide compound I, or a pharmaceutically acceptable salt thereof.
2. The method according to embodiment 1, wherein LG³ is halogen.
3. The method according to embodiment 2, wherein LG³ is chloro.
4. The method according to any of embodiments 1-3, wherein the reaction conditions comprise a base.
5. The method according to embodiment 4, wherein the base is $K_2CO_3$.
6. The method according to any one of embodiments 1-5, wherein a compound of formula 1-11 is prepared by a process comprising:
reacting a compound of formula 1-10:

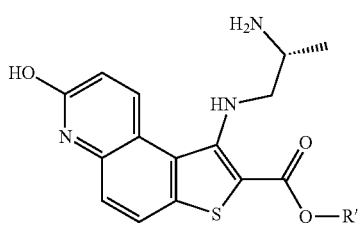

or a salt thereof, wherein
R' is hydrogen or optionally substituted $C_{1-6}$ aliphatic or aryl;
under suitable reaction conditions to provide a compound of formula 1-11, or a salt thereof.
7. The method according to embodiment 6, wherein R' is $C_{1-6}$ aliphatic.
8. The method according to embodiment 7, wherein R' is methyl.
9. The method according any one of embodiments 6-8, wherein the reaction conditions comprise a base.
10. The method according to embodiment 9, wherein the base is DBU.
11. The method according any one of embodiments 6-10, wherein a compound of formula 1-10 is prepared by a process comprising:
reacting a compound of formula 1-9:

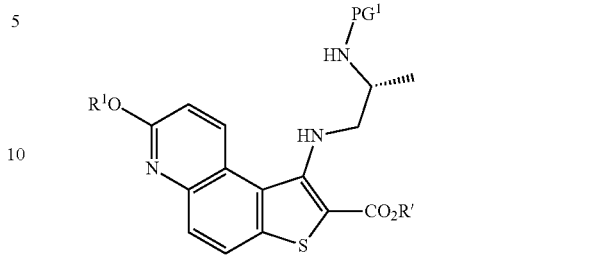

or a salt thereof, wherein
R¹ is a suitable oxygen protecting group; and
PG¹ is a suitable nitrogen protecting group;
under suitable reaction conditions to provide a compound of formula 1-10, or a salt thereof.
12. The method according to embodiment 11, wherein R' is $C_{1-6}$ aliphatic.
13. The method according to embodiment 12, wherein R' is methyl.
14. The method according to any one of embodiments 11-13, wherein PG¹ is Boc.
15. The method according to any one of embodiments 11-14, wherein R¹ is benzyl.
16. The method according to any one of embodiments 11-15, wherein the reaction conditions comprise an acid.
17. The method according to embodiment 16, wherein the acid is HCl.
18. The method according to embodiment 16, wherein the acid is BSA.
19. The method according to any one of embodiments 11-17, wherein a compound of formula 1-10 is provided as an HCl salt.
20. The method according to claim any one of embodiments 11-16 and 18, wherein a compound of formula 1-10 is provided as a BSA salt
21 The method according to any one of embodiments 11-20, wherein a compound of formula 1-9 is prepared by a process comprising:
reacting a compound of formula 1-7:

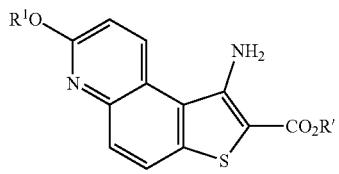

or a salt thereof;
with a compound of formula 1-8:

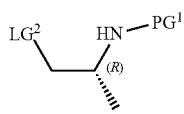

or salt thereof, wherein,
LG² is a suitable leaving group;
under suitable reaction conditions to provide a compound of formula 1-9, or a salt thereof.

22. The method according to embodiment 21, wherein R' is $C_{1-6}$ aliphatic.
23. The method according to embodiment 22, wherein R' is methyl.
24. The method according to any one of embodiments 21-23, wherein $R^1$ is benzyl.
25. The method according to any one of embodiments 21-24, wherein a compound of formula 1-8 is:

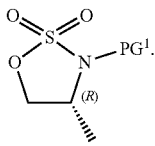

26. The method according to any one of embodiments 21-25, wherein $PG^1$ is Boc.
27. The method according to any one of embodiments 21-26, wherein the reaction conditions comprise a base.
28. The method according to embodiment 27, wherein the base is LiOtBu.
29. The method according to any one of embodiments 21-28, wherein a compound of formula 1-7 is prepared by a process comprising:
reacting a compound of formula 1-5:

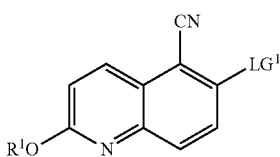

or a salt thereof, wherein:
$LG^1$ is a suitable leaving group; and
$R^1$ is a suitable oxygen protecting group;
with a compound of formula 1-6:

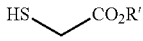

under suitable reaction conditions to provide a compound of formula 1-7.
30. The method according to embodiment 29, wherein $LG^1$ is halogen.
31. The method according to embodiment 30, wherein $LG^1$ is bromide.
32. The method according to any one of embodiments 29-31, wherein $R^1$ is benzyl.
33. The method according to any one of embodiments 29-32, wherein R' is $C_{1-6}$ aliphatic.
34. The method according to embodiment 33, wherein R' is methyl.
35. The method according any one of embodiments 29-34, wherein the reaction conditions comprise a base.
36. The method according to embodiment 35, wherein the base is NaOMe.
37. The method according to any one of embodiments 29-36, wherein a compound of formula 1-5 is prepared by a process comprising:

reacting a compound of formula 1-4:

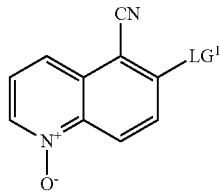

or a salt thereof;
with a compound of formula $R^1OH$ under suitable reaction conditions to provide a compound of formula 1-5, or a salt thereof.
38. The method according to embodiment 37, wherein $LG^1$ is halogen.
39. The method according to embodiment 38, wherein $LG^1$ is bromide.
40. The method according to any one of embodiments 37-39, wherein $R^1$ is benzyl.
41. The method according to any one of embodiments 37-40, wherein the reaction conditions comprise a base.
42. The method according to embodiment 41, wherein the base is DIEA.
43. The method according to any one of embodiments 36-42, wherein the reaction conditions comprise an activating compound.
44. The method according to embodiment 43, wherein the activating compound is p-toluenesulfonic anhydride.
45. The method according to any one of embodiments 37-44, wherein a compound of formula 1-4 is prepared by a process comprising:
reacting a compound of formula 1-3:

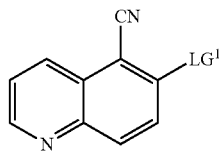

or a pharmaceutically acceptable salt thereof;
under suitable reaction conditions to provide a compound of formula 1-4, or a salt thereof.
46. The method according to embodiment 45, wherein $LG^1$ is halogen.
47. The method according to embodiment 46, wherein $LG^1$ is bromide.
48. The method according to any one of embodiments 45-47, wherein the reaction conditions comprise a peroxide reagent.
49. The method according to embodiment 48, wherein the peroxide reagent is mCPBA.
50. The method according to any one of embodiments 45-49, wherein a compound of formula 1-3 is prepared by a process comprising:

reacting a compound of formula 1-2:

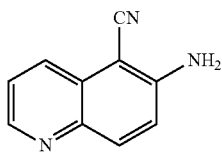

or a salt thereof;
under suitable reaction conditions to provide a compound of formula 1-3, or a salt thereof.
51. The method according to embodiment 50, wherein the reaction conditions comprise a nitrite compound.
52. The method according to embodiment 51, wherein the nitrite compound is tert-butyl nitrite.
53. The method according to any one of embodiments 50-52, wherein the reaction conditions further comprise a bromide source.
54. The method according to embodiment 53, wherein the bromide source is $CuBr_2$.
55. The method according to claims any one of embodiments 50-54, wherein the reaction conditions comprise in situ formation of a diazonium intermediate of formula 1-2a:

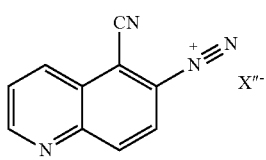

wherein X" is a counterion.
56. The method according to any one of embodiments 50-55, wherein a compound of formula 1-2 is prepared by a process comprising:
reacting a compound of formula 1-1:

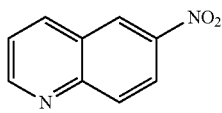

or a salt thereof;
under suitable reaction conditions to provide a compound of formula 1-2, or a pharmaceutically acceptable salt thereof.
57. The method according to embodiment 56, wherein the reaction conditions comprise a cyanating agent.
58. The method according to embodiment 57, wherein the cyanating agent is ethyl cyanoacetate.
59. The method according to any one of embodiments 56-58, wherein the reaction conditions further comprise a base.
60. The method according to embodiment 59, wherein the base is DBU.
61. The method according to claim any one of embodiments 56-60, wherein the reaction conditions further comprise an acid.
62. The method according to embodiment 61, wherein the acid is HCl.

We claim:
1. A method for preparing compound I:

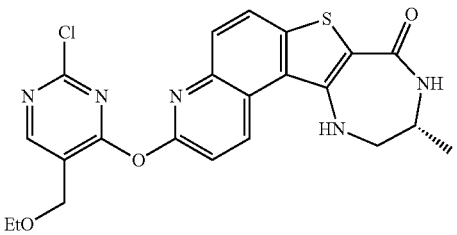

or a pharmaceutically acceptable salt thereof, comprising the steps of:
reacting a compound of formula 1-11:

or a salt thereof;
with a compound of formula 1-12,

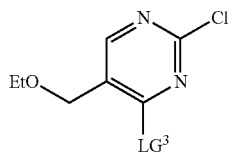

wherein $LG^3$ is a suitable leaving group;
under suitable reaction conditions to provide compound I, or a pharmaceutically acceptable salt thereof;
wherein the compound of formula 1-11 is prepared by a process comprising:
reacting a compound of formula 1-10:

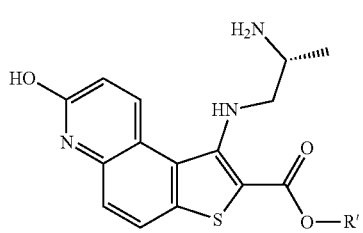

or a salt thereof, wherein
R' is hydrogen or optionally substituted $C_{1-6}$ aliphatic or aryl;
under suitable reaction conditions to provide a compound of formula 1-11, or a salt thereof.

2. The method according to claim 1, wherein a compound of formula 1-10 is prepared by a process comprising:
reacting a compound of formula 1-9:

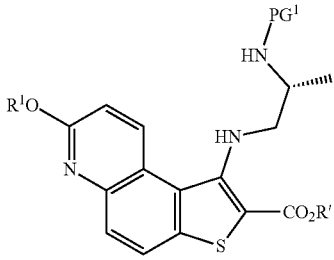

1-9 or a salt thereof, wherein
R¹ is a suitable oxygen protecting group; and
PG¹ is a suitable nitrogen protecting group;
under suitable reaction conditions to provide a compound of formula 1-10, or a salt thereof.

3. The method according to claim 2, wherein the suitable reaction conditions to provide a compound of formula 1-10, or a salt thereof, comprise an acid.

4. The method according to claim 3, wherein the acid is HCl or BSA.

5. The method according to claim 2, wherein a compound of formula 1-10 is provided as an HCl salt.

6. The method according to claim 2, wherein a compound of formula 1-10 is provided as a BSA salt.

7. The method according to claim 2, wherein a compound of formula 1-9 is prepared by a process comprising:
reacting a compound of formula 1-7:

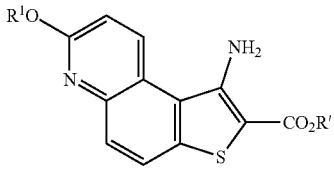

1-7 or a salt thereof;
with a compound of formula 1-8:

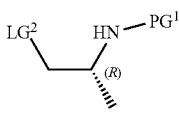

1-8 or salt thereof, wherein,
LG² is a suitable leaving group;
under suitable reaction conditions to provide a compound of formula 1-9, or a salt thereof.

8. The method according to claim 7, wherein a compound of formula 1-8 is:

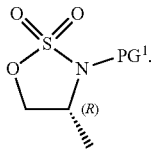

9. The method according to claim 7, wherein a compound of formula 1-7 is prepared by a process comprising:
reacting a compound of formula 1-5:

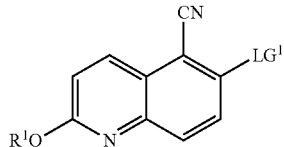

1-5 or a salt thereof, wherein:
LG¹ is a suitable leaving group; and
R¹ is a suitable oxygen protecting group;
with a compound of formula 1-6:

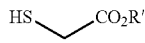

1-6 under suitable reaction conditions to provide a compound of formula 1-7.

10. The method according to claim 9, wherein a compound of formula 1-5 is prepared by a process comprising:
reacting a compound of formula 1-4:

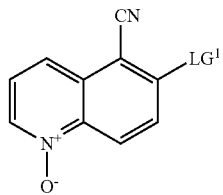

1-4 or a salt thereof;
with a compound of formula R¹OH under suitable reaction conditions to provide a compound of formula 1-5, or a salt thereof.

11. The method according to claim 10, wherein the suitable reaction conditions to provide a compound of formula 1-5, or a salt thereof, comprise an activating compound.

12. The method according to claim 10, wherein a compound of formula 1-4 is prepared by a process comprising:
reacting a compound of formula 1-3:

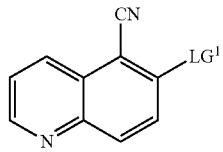

1-3 or a salt thereof;
under suitable reaction conditions to provide a compound of formula 1-4, or a salt thereof.

13. The method according to claim 12, wherein the suitable reaction conditions to provide a compound of formula 1-4, or a salt thereof, comprise a peroxide reagent.

14. The method according to claim 12, wherein a compound of formula 1-3 is prepared by a process comprising:
reacting a compound of formula 1-2:

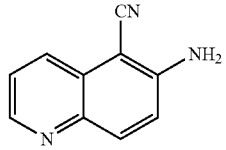

1-2 or a salt thereof;
under suitable reaction conditions to provide a compound of formula 1-3, or a salt thereof.

15. The method according to claim 14, wherein the suitable reaction conditions to provide a compound of formula 1-3, or a salt thereof, comprise a nitrite compound.

16. The method according to claim 15, wherein the suitable reaction conditions to provide a compound of formula 1-3, or a salt thereof, further comprise a bromide source.

17. The method according to claim 14, wherein the reaction conditions comprise in situ formation of a diazonium intermediate of formula 1-2a:

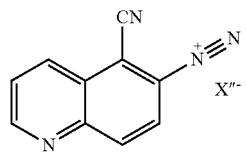

wherein X" is a counterion.

18. The method according to claim 14, wherein a compound of formula 1-2 is prepared by a process comprising: reacting a compound of formula 1-1:

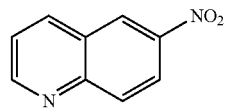

or a salt thereof;
under suitable reaction conditions to provide a compound of formula 1-2, or a thereof.

19. The method according to claim 18, wherein the suitable reaction conditions to provide a compound of formula I-2, or a salt thereof, comprise a cyanating agent.

* * * * *